US008863746B2

(12) United States Patent
Totz

(10) Patent No.: US 8,863,746 B2
(45) Date of Patent: *Oct. 21, 2014

(54) DEVICE AND METHOD FOR PLACING WITHIN A PATIENT AN ENTERAL TUBE AFTER ENDOTRACHEAL INTUBATION

(75) Inventor: Kenneth Alan Totz, Houston, TX (US)

(73) Assignee: Kim Technology Partners, LP, Houston, TX (US)

( * ) Notice: Subject to any disclaimer, the term of this patent is extended or adjusted under 35 U.S.C. 154(b) by 1496 days.

This patent is subject to a terminal disclaimer.

(21) Appl. No.: 12/352,404

(22) Filed: Jan. 12, 2009

(65) Prior Publication Data

US 2009/0125002 A1 May 14, 2009

Related U.S. Application Data

(63) Continuation-in-part of application No. 11/188,821, filed on Jul. 25, 2005, now Pat. No. 7,921,847.

(51) Int. Cl.
*A44B 1/04* (2006.01)
*A44B 11/25* (2006.01)
*A44B 17/00* (2006.01)
*A61M 16/00* (2006.01)
*A61M 31/00* (2006.01)
*A61M 37/00* (2006.01)
*A61M 29/00* (2006.01)
*A61M 25/00* (2006.01)
*A61M 16/04* (2006.01)
*A61J 15/00* (2006.01)

(52) U.S. Cl.
CPC .......... *A61M 16/04* (2013.01); *A61M 16/0488* (2013.01); *A61J 15/0003* (2013.01); *A61M 16/0415* (2014.02); *A61M 16/0418* (2014.02); *A61M 16/0479* (2014.02); *A61M 16/0486* (2014.02); *A61M 16/0434* (2013.01); *A61J 15/0073* (2013.01); *A61J 15/0023* (2013.01); *A61M 2205/32* (2013.01)
USPC .................. 128/207.15; 24/339; 128/200.26; 128/207.14; 128/207.16; 604/94.01; 604/101.01; 604/101.04; 604/264; 604/284; 604/523; 604/544; 606/192; 606/193; 606/194; 606/195; 606/196

(58) Field of Classification Search
USPC ............. 128/200.26, 207.14, 207.15, 207.16; 604/94.01, 96.01, 101.01, 101.04, 264, 604/284, 523, 544; 606/192–196; 24/339
See application file for complete search history.

(56) References Cited

U.S. PATENT DOCUMENTS 3,625,793 A 12/1971 Sheridan et al.
4,023,596 A 5/1977 Tate
(Continued)

FOREIGN PATENT DOCUMENTS

DE 19533615 4/1997
EP 0 230 790 8/1987
JP 2002-315832 10/2002

OTHER PUBLICATIONS

Response filed Oct. 1, 2010 to Final Office Action (merits) Mailed Jul. 9, 2010 in parent U.S. Appl. No. 11/188,821, 46 pages.

(Continued)

*Primary Examiner* — Patricia Bianco
*Assistant Examiner* — Brandon L Jackson
(74) *Attorney, Agent, or Firm* — Gordon G. Waggett, P.C.

(57) ABSTRACT

The present invention is directed to a novel device and method for providing a disposable endotracheal intubation device for use with an auxiliary passageway serving as a guide for the placement of an orogastric or other enterally directed device in a patient. The present invention pertains to a medical catheter device, removably attachable to an endotracheal tube, for guiding the path of an enteral tube into the esophagus of a patient. The catheter device preferably employs an adjustable clamp to fix the position of the catheter relative to the endotracheal tube. The present invention also pertains to a combination medical intubation device comprising an endotracheal tube and a catheter proximate the endotracheal tube to guide the path of an enteral tube. The present invention also pertains to a method of intubating a patient using this combination medical intubation device.

42 Claims, 34 Drawing Sheets

(56) References Cited

U.S. PATENT DOCUMENTS

| | | | |
|---|---|---|---|
| 4,090,518 A | 5/1978 | Elam | |
| 4,167,946 A | 9/1979 | Sandstrom | |
| 4,231,365 A | 11/1980 | Scarberry | |
| 4,233,984 A | 11/1980 | Walling | |
| 4,256,099 A | 3/1981 | Dryden | |
| 4,327,720 A | 5/1982 | Bronson et al. | |
| 4,351,330 A | 9/1982 | Scarberry | |
| 4,453,545 A | 6/1984 | Inoue | |
| 4,584,998 A | 4/1986 | McGrail | |
| 4,672,960 A | 6/1987 | Frankel | |
| 4,774,945 A | 10/1988 | White et al. | |
| 4,840,172 A | 6/1989 | Augustine et al. | |
| 4,840,173 A | 6/1989 | Porter, III | |
| 5,009,227 A | 4/1991 | Nieuwstad | |
| 5,038,766 A | 8/1991 | Parker | |
| 5,065,755 A | 11/1991 | Klafta | |
| 5,067,497 A | 11/1991 | Greear et al. | |
| 5,069,206 A | 12/1991 | Crosbie | |
| 5,143,062 A | 9/1992 | Peckham | |
| 5,253,643 A | 10/1993 | Price | |
| 5,287,848 A | 2/1994 | Cubb et al. | |
| 5,353,787 A | 10/1994 | Price | |
| 5,372,131 A | 12/1994 | Heinen, Jr. | |
| 5,499,625 A | 3/1996 | Frass et al. | |
| 5,520,175 A * | 5/1996 | Fry | 128/207.15 |
| 5,551,421 A | 9/1996 | Noureldin et al. | |
| 5,551,946 A | 9/1996 | Bullard | |
| 5,588,424 A | 12/1996 | Insler et al. | |
| 5,660,175 A | 8/1997 | Dayal | |
| 5,665,052 A | 9/1997 | Bullard | |
| 5,682,880 A | 11/1997 | Brain | |
| 5,694,929 A | 12/1997 | Christopher | |
| 5,806,516 A * | 9/1998 | Beattie | 128/207.17 |
| 5,827,227 A | 10/1998 | DeLago | |
| 5,878,745 A | 3/1999 | Brain | |
| 5,879,499 A * | 3/1999 | Corvi | 156/175 |
| 5,957,134 A | 9/1999 | Lee | |
| 5,964,217 A | 10/1999 | Christopher | |
| 6,142,144 A | 11/2000 | Pacey | |
| 6,298,525 B1 * | 10/2001 | Margo | 24/336 |
| 6,374,827 B1 | 4/2002 | Bowden et al. | |
| 6,439,232 B1 | 8/2002 | Brain | |
| 6,443,156 B1 | 9/2002 | Niklason et al. | |
| 6,460,540 B1 | 10/2002 | Klepper | |
| 6,461,363 B1 | 10/2002 | Gadberry et al. | |
| 6,513,527 B1 | 2/2003 | Abdel-Aziz | |
| 6,520,183 B2 | 2/2003 | Amar | |
| 6,543,446 B1 | 4/2003 | Christopher | |
| 6,543,447 B2 | 4/2003 | Pacey | |
| 6,568,388 B2 | 5/2003 | Christopher | |
| 6,626,169 B2 | 9/2003 | Gaitini | |
| 6,631,713 B1 | 10/2003 | Christopher | |
| 6,655,377 B2 | 12/2003 | Pacey | |
| 6,718,970 B2 | 4/2004 | Sniadach | |
| 6,729,325 B2 | 5/2004 | Alfery | |
| 6,843,250 B2 | 1/2005 | Efrati | |
| 6,860,264 B2 | 3/2005 | Christopher | |
| 6,923,176 B2 | 8/2005 | Ranzinger | |
| 6,986,769 B2 * | 1/2006 | Nelson et al. | 606/41 |
| 7,013,899 B2 | 3/2006 | Alfery et al. | |
| 7,040,322 B2 | 5/2006 | Fortuna | |
| RE39,508 E | 3/2007 | Parker | |
| 7,201,168 B2 | 4/2007 | McGrail et al. | |
| 7,278,420 B2 | 10/2007 | Ganesh et al. | |
| 7,305,985 B2 | 12/2007 | Brain | |
| 7,921,847 B2 * | 4/2011 | Totz | 128/207.15 |
| 8,099,837 B2 * | 1/2012 | Santin et al. | 24/297 |
| 2001/0054425 A1 | 12/2001 | Bertram | |
| 2002/0162555 A1 * | 11/2002 | West et al. | 128/206.29 |
| 2003/0051734 A1 | 3/2003 | Brain | |
| 2003/0062039 A1 | 4/2003 | Sniadach | |
| 2003/0183234 A1 | 10/2003 | Ranzinger | |
| 2004/0000314 A1 | 1/2004 | Angel | |
| 2004/0020491 A1 | 2/2004 | Fortuna | |
| 2004/0111069 A1 | 6/2004 | Schaaf et al. | |
| 2005/0039754 A1 | 2/2005 | Simon | |
| 2005/0090712 A1 | 4/2005 | Cubb | |
| 2005/0137614 A1 | 6/2005 | Porter et al. | |
| 2006/0090761 A1 | 5/2006 | Kurrus | |
| 2006/0166548 A1 | 7/2006 | Williams et al. | |
| 2007/0106117 A1 | 5/2007 | Yokota | |
| 2007/0106121 A1 | 5/2007 | Yokota et al. | |
| 2007/0106122 A1 | 5/2007 | Yokota et al. | |
| 2007/0163596 A1 | 7/2007 | Mikkaichi et al. | |
| 2007/0221229 A1 | 9/2007 | Rahaghi et al. | |
| 2007/0244546 A1 | 10/2007 | Francis | |
| 2008/0000481 A1 | 1/2008 | Ganesh et al. | |
| 2008/0060655 A1 | 3/2008 | Brain | |
| 2008/0135052 A1 | 6/2008 | Bussieres | |
| 2008/0142017 A1 | 6/2008 | Brain | |
| 2008/0146879 A1 | 6/2008 | Pacey | |
| 2008/0167603 A1 | 7/2008 | Stenzler et al. | |
| 2009/0107497 A1 | 4/2009 | Stenzler et al. | |
| 2009/0229615 A1 * | 9/2009 | Stenzler et al. | 128/207.14 |

OTHER PUBLICATIONS

Advisory Office Action Mailed Oct. 27, 2010 in parent U.S. Appl. No. 11/188,821, 6 pages.
Supplemental Response filed Nov. 5, 2010 to Final Office Action (merits) Mailed Jul. 9, 2010 in parent U.S. Appl. No. 11/188,821, 26 pages.
Related PCT Application: PCT/US2010/020082 (filed Jan. 5, 2010): PCT Notification of Transmittal of the International Search Report and the Written Opinion of the International Searching Authority, or the Declaration (Aug. 13, 2010)(2 pages).
Related PCT Application: PCT/US2010/020082 (filed Jan. 5, 2010): PCT International Search Report (Aug. 13, 2010)(4 pages).
Related PCT Application: PCT/US2010/020082 (filed Jan. 5, 2010): PCT Written Opinion of the International Searching Authority (Aug. 13, 2010)(4 pages).
Office Action (Restriction) Mailed Mar. 30, 2009 in parent U.S. Appl. No. 11/188,821, 7 pages.
Response to Office Action (Restriction) Mailed Mar. 30, 2009 in parent U.S. Appl. No. 11/188,821 (Apr. 30, 2009), 2 pages.
2nd Office Action (merits) Mailed Jul. 7, 2009 in parent U.S. Appl. No. 11/188,821, 38 pages.
Response to 2nd Office Action (merits) Mailed Jul. 7, 2009 in parent U.S. Appl. No. 11/188,821 (Oct. 7, 2009), 73 pages.
Final Office Action (merits) Mailed Jul. 9, 2010 in parent U.S. Appl. No. 11/188,821, 34 pages.
Netter, Frank H., M.D., (Sharon Colacino, Consulting Ed.), "Atlas of Human Anatomy", (1989), Plate 57, Ciba-Geigy Corporation, Summit, New Jersey.
Prior Art described in Specification paragraphs [00113]-[00114] and Fig. 1.
Adjustable Nylon Ratchet Clamps. 3-page printout from the website catalog of ElectricalBasics.com.
Hook and loop reclosable cable tie wraps. 2-page printout from the website catalog of levitonproducts.com.

* cited by examiner

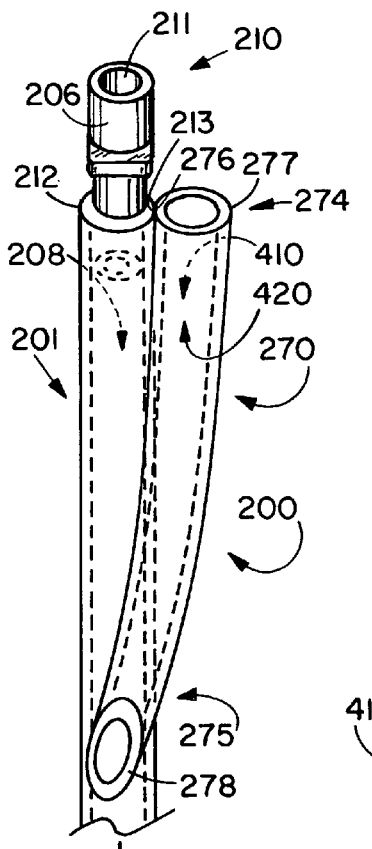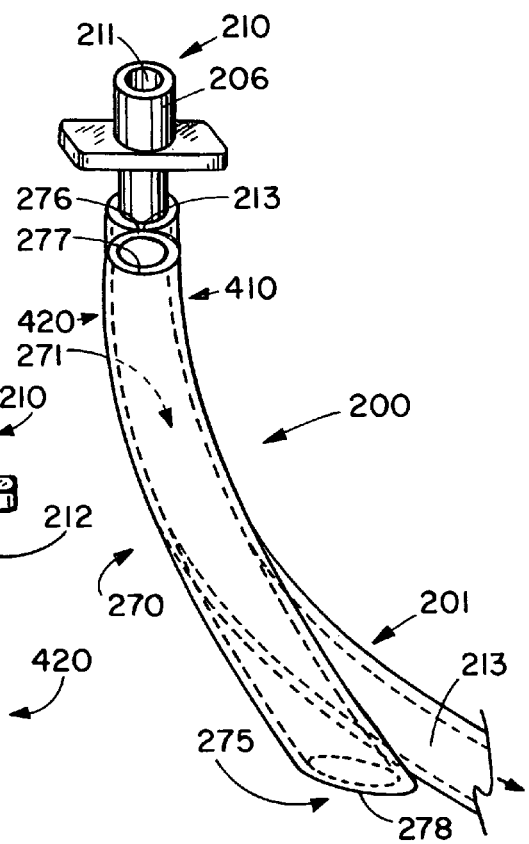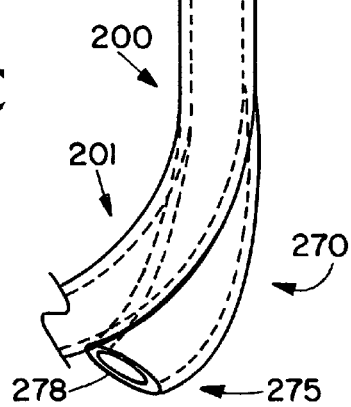
Fig. 2c
Fig. 2b
Fig. 2d

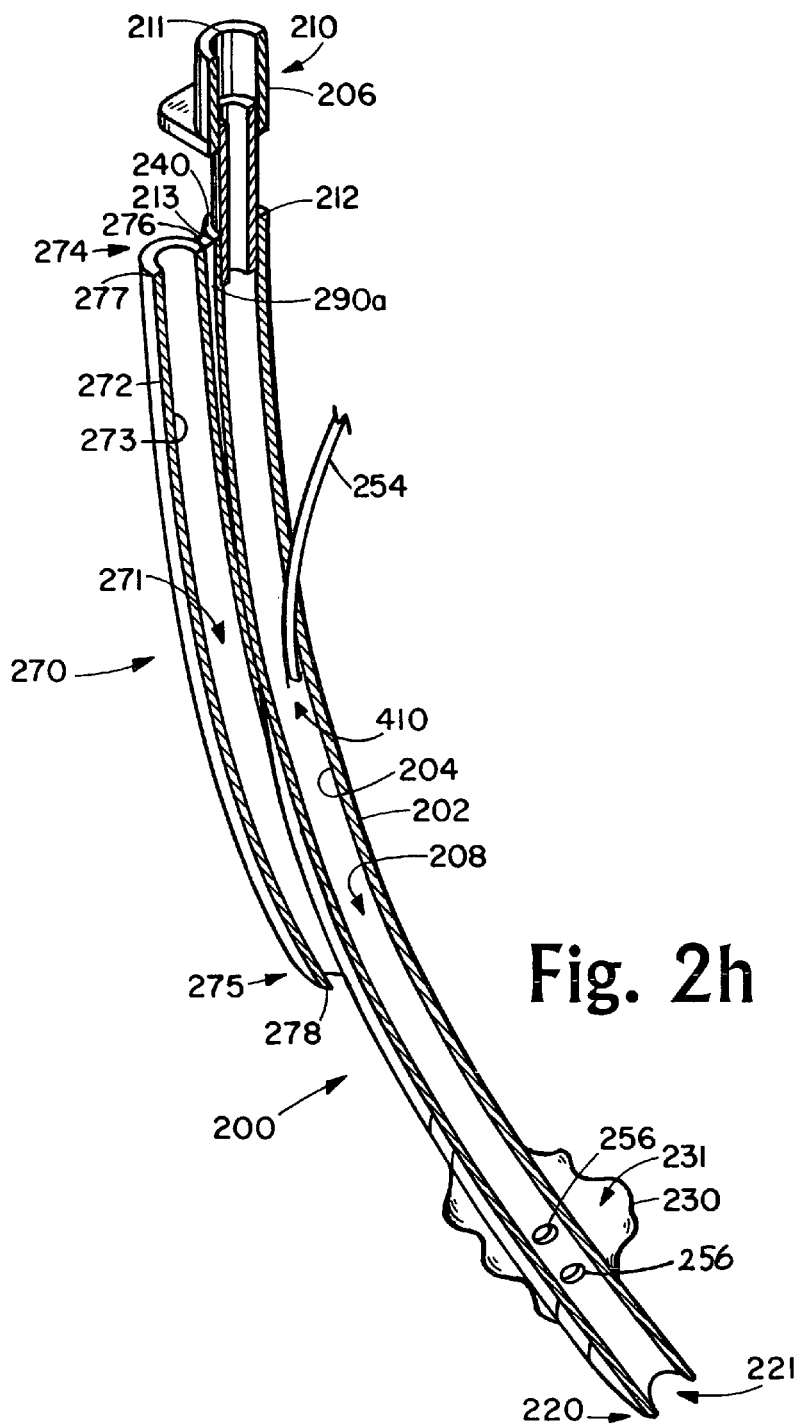

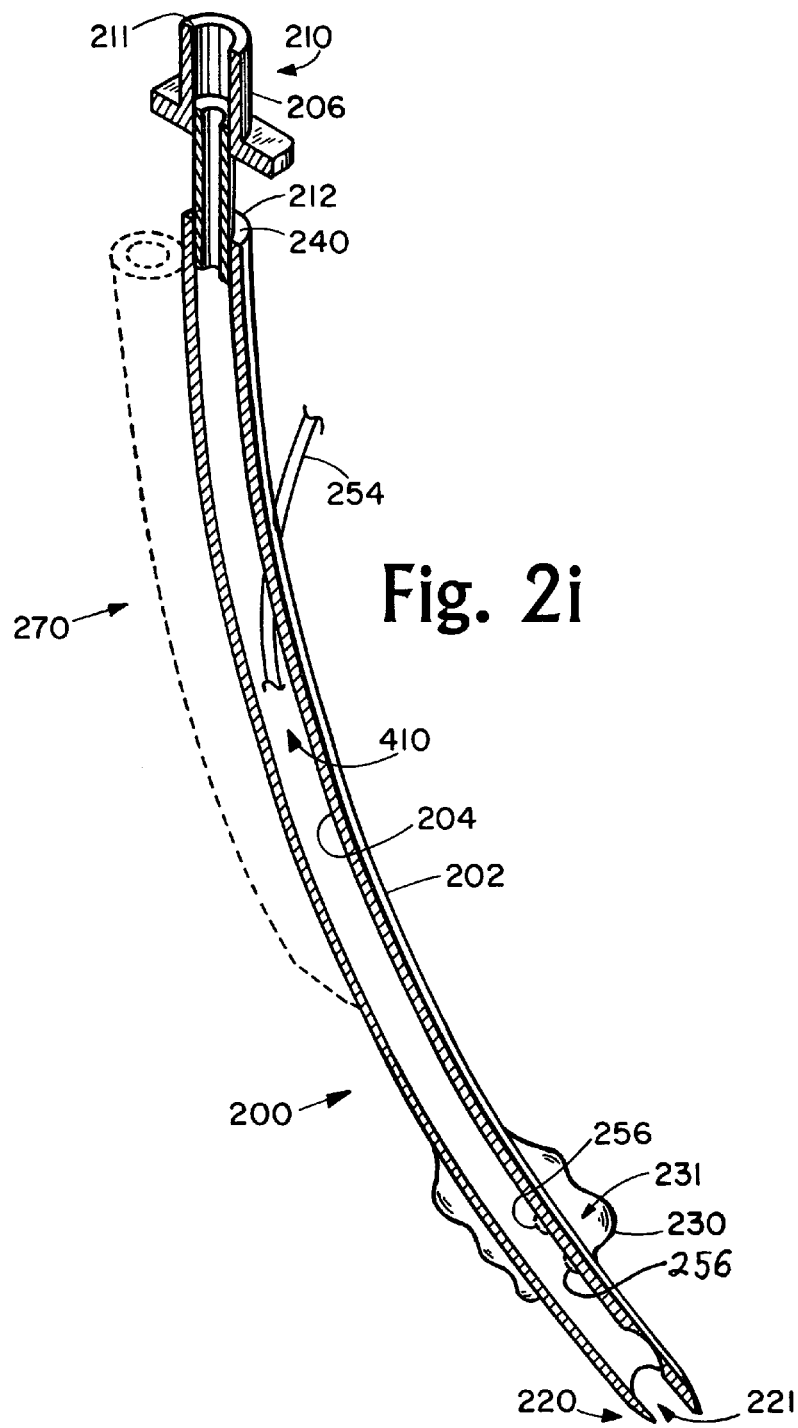

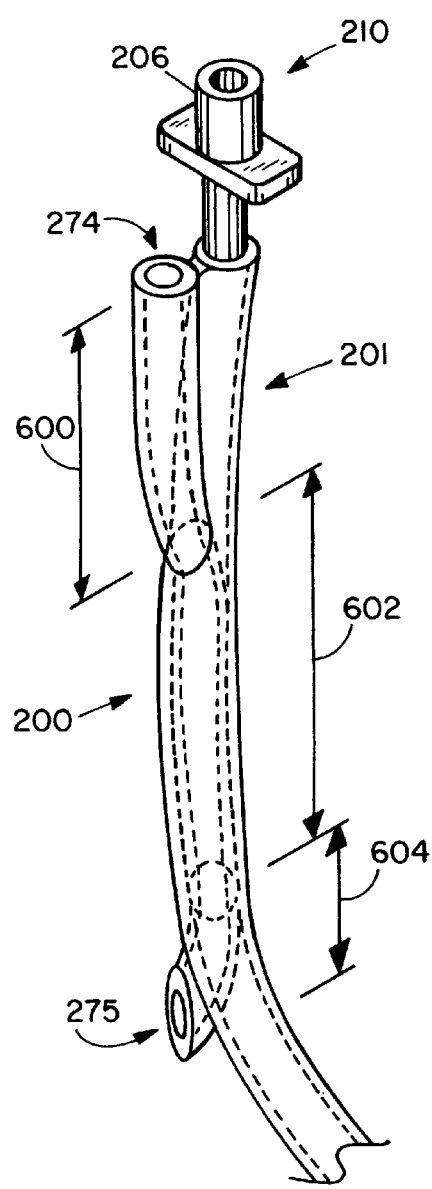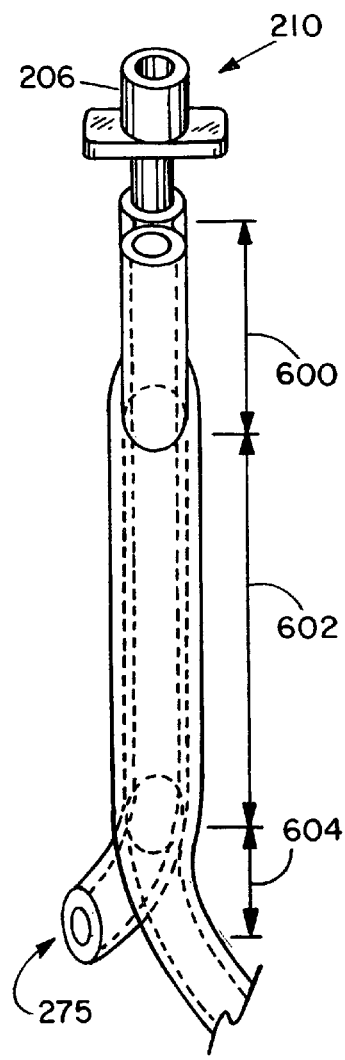
Fig. 6a
Fig. 6b

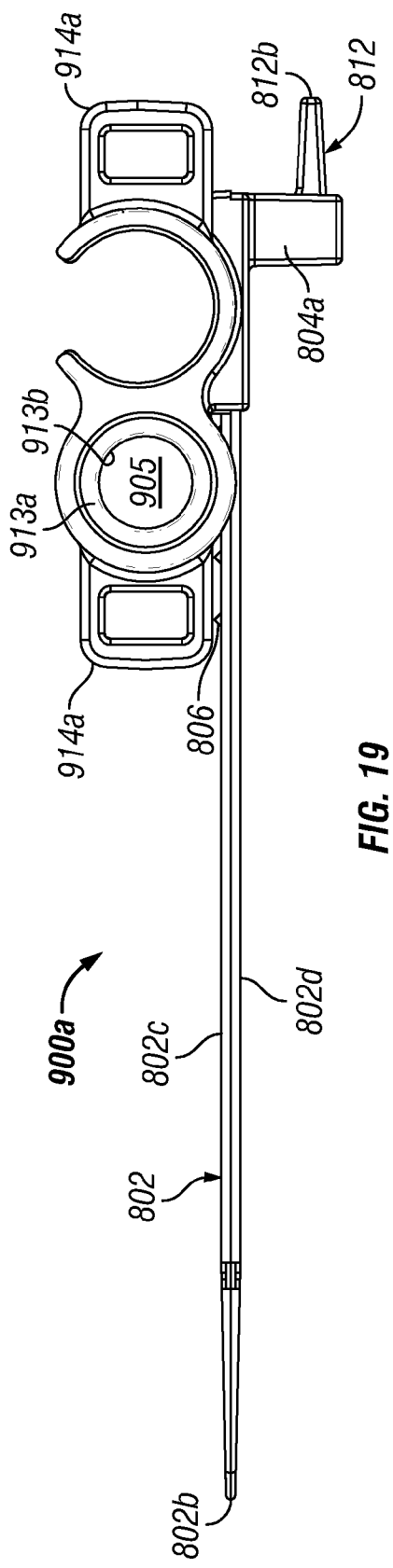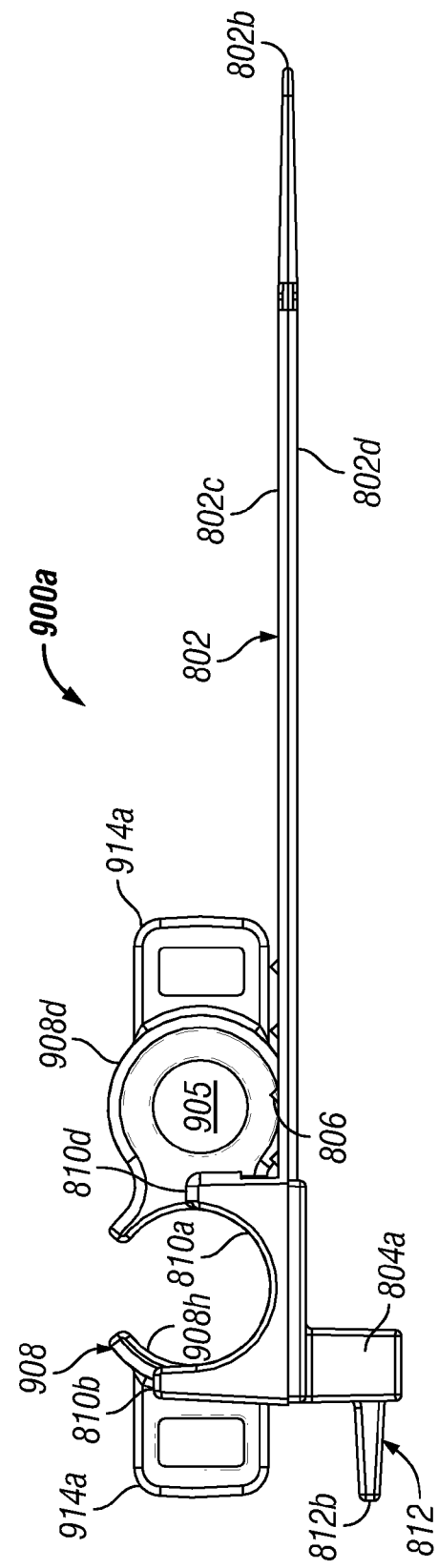
FIG. 19
FIG. 20

DEVICE AND METHOD FOR PLACING WITHIN A PATIENT AN ENTERAL TUBE AFTER ENDOTRACHEAL INTUBATION

CROSS-REFERENCE TO RELATED APPLICATIONS

This application is a continuation-in-part (CIP) and claims the benefit of priority of U.S. patent application Ser. No. 11/188,821 entitled "Improved Device and Method for Placing Within a Patient an Enteral Tube After Endotracheal Intubation", filed Jul. 25, 2005, now U.S. Pat. No. 7,921,847, the disclosure of which is considered part of and is incorporated by reference in its entirety in the disclosure of this application.

STATEMENT REGARDING FEDERALLY SPONSORED RESEARCH OR DEVELOPMENT

Not Applicable.

BACKGROUND OF THE INVENTION

The present invention is directed to a novel device and method for providing a disposable endotracheal intubation device for use in conjunction with an auxiliary passageway serving as a guide for the placement of an orogastric or other enterally directed device in a patient.

An early airway apparatus for assisting in artificial respiration of a patient comprised an arcuate, open-ended tubular member which was adapted to be inserted into the patient's trachea. The tubular member carried an external, inflatable resilient sleeve (cuff near the distal end thereof for affecting a seal with the inner wall of the trachea. Following the placement of this endotracheal tube (catheter) respiratory device (a procedure known as endotracheal intubation), it would often be necessary to additionally place within the patient an orogastric (OG) or nasogastric (NG) tube for a number of clinical functions, including, for example, suction of gastric contents, suction of aspiration secretions, suction of air from an inflated stomach, placement of contrast materials and feeding.

However, the placement of an NG tube through the patient's nasal passageway is fraught with potentially serious complications. For example, placement of an NG tube into a patient can cause pressure necrosis of the nasal vestibule, traumatize the nasal mucosa causing massive hemorrhage, puncture the cranial vault, cause toxic shock, perforate the back of the throat, and cause occlusion of facial sinus draining tracts leading to serious infections. Furthermore, passage of an NG tube into a patient many times is only possible by placing one's hand into the patient's posterior oropharynx to facilitate the further directing of the tube into the proximal esophagus.

Similarly, it is often difficult placing an OG tube in a patient due to problems navigating the OG tube past an obstructing tongue of the patient thereby warranting placement of the health practitioner's hand into the patient's posterior orpharynx to direct the tube into the proximal esophagus.

The conventional way of placing the NG and OG tubes after endotracheal intubation place the patient at iatrogenic risk of injury and the health practitioner/operator at risk of being bitten or exposed to enumerable infectious diseases from placing his or her hands into the patient's mouth.

Separate endotracheal, NG and OG tubes are known in the art, as are various devices and methods for using them in combination. A commonly used endotracheal tube utilizes a dual lumen system, where the primary lumen comprises an open-ended tubular member which, when placed into the patient, extends at its distal end into the patient's trachea, and at its opposite end, remains external to the patient. This endotracheal tube commonly employs an external, inflatable resilient sleeve or cuff near the distal end thereof for affecting a seal with the inner wall of the trachea. The sleeve is inflated via a second lumen attached proximate the endotracheal tube. Dual lumen endotracheal tubes are available under a number of brand names, including the Malhnckrodt® brand. A standard dual lumen endotracheal tube employing an inflatable cuff is shown and described in U.S. Pat. No. 3,625,793 to Sheridan. U.S. Pat. No. 4,584,998 to McGrail (owned by Mallinckrodt), discloses a multi-lumen tracheal tube wherein the standard endotracheal tube employs up to three lumens for conducting various functions associated within the patient's trachea, such as high frequency ventilation. U.S. Pat. No. 5,143,062 to Peckham discloses a standard dual lumen endotracheal tube having a third lumen for use in suctioning the patient's secretions pooled in the trachea above the tube's inflated cuff. Skoljarev—DE19533615 (Abstract) shows an endotracheal tube employing a suction catheter, the tube and catheter encased within an oropharyngeal tube protecting same from being bitten by the patient.

Numerous multi-lumen esophageal/tracheal airway devices exist that are designed to allow for blind (without use of a laryngoscope) insertion of the device into the patient. Typically, these dual lumen airway devices employ one elongated lumen having an inflation cuff similar to a standard endotracheal tube wherein the cuff is located near the distal end of the tube. The other lumen is typically shorter in length and employs an inflation cuff located on the proximal side of openings in the shorter lumen. The device is configured such that either lumen could be used for ventilation regardless of which lumen enters the trachea. The non-ventilating lumen can be used to remove gastric fluids. If the longer lumen enters the trachea, its cuff seals the trachea and the longer lumen can be used for ventilation, while the opening of the shorter lumen would be proximate the pharyngeal area of the patient where a seal can be formed to direct gastric fluids into the lumen. This prior art also discloses means of marking the endotracheal tubes with, e.g., an X-ray opaque stripe to facilitate the placement and orientation of the airway and the location of the inflatable cuffs.

For example, Fortuna, US 2004/0020491 A1, describes a combination artificial airway device and esophageal obturator that includes an esophageal cuff and a supraglottic cuff that are inflated in a sequence to provide quick isolation of the esophagus relative to the tracheal air passage. The esophageal cuff is designed to enter the esophagus and to create a seal around the esophagus with the inflatable cuff. The supraglottic cuff does not enter the trachea, but instead inflates to form a seal. Fortuna further describes that if necessary, an orogastric tube can be passed directly to the stomach through the esophageal limb. The portion of the esophageal limb passing through the supraglottic cuff is integrated internal to the supraglottic cuff. A disadvantage of this device is that the airway created is temporary and not secure, and would not be used where medical judgment calls for the use of an endotracheal tube having a cuffed end that physically enters the trachea.

Angel, US 2004/0000314 A1, describes a multi-lumen airway assembly used in a procedure that requires instrumentation to be inserted in an air passage (i.e., larynx, trachea, bronchi or bronchioles) of a patient. The multi-lumen device of Angel is designed to pass through the trachea and into the bronchii. Angel describes an airway assembly employing a reinforced, flexible first conduit, a second conduit (e.g., suction conduit), a third conduit (e.g., ventilation conduit) and an expandable member.

U.S. Pat. No. 5,499,625 to Frass et al. discloses a twin lumen, dual balloon cuff coaxial device designed for use in emergency situations and difficult airways. It can be inserted blindly into the oropharynx and usually enters the esophagus in about 90% of times, and X-ray opaque markings on the lumen assist medical personnel in ascertaining placement and positioning of the device. It is designed to provide effective lung ventilation regardless of whether esophageal or tracheal placement is accomplished. When placed in the trachea, its ventilation function is much like a traditional endotracheal tube. When placed in the esophagus, ventilation is possible through the other coaxial lumen via the use of perforations found between two inflation cuffs.

Ranzinger, US 2003/0183234 A1, describes a dual lumen, dual balloon cuff resuscitation tube. This resuscitation tube comprises a tube wall for alternative artificial endotracheal or esophageal obturator respiration, with a first lumen and a second lumen extending substantially parallel thereto, wherein a first inflatable balloon surrounding the tube wall is disposed in the region of the end of the resuscitation tube facing the body, and a second inflatable balloon surrounding the tube wall is disposed at a separation from the first inflatable balloon, an axial opening of the first lumen is disposed directly at the end of the second balloon facing the body, and the resuscitation tube is formed with one lumen in the region of the first balloon. This permits insertion of intubation aids via the first lumen such that the resuscitation tube can be used with versatility. Similarly with Frass et al., when placed in the trachea, the resuscitation tube's ventilation function is much like a traditional endotracheal tube. When placed in the esophagus, ventilation is possible through the other lumen via the use of perforations found between two inflation cuffs.

Sniadach, US 2003/0062039 A1, describes an intubation system employing an esophageal obturator, and intubation slide, a guide wire and an endotracheal airway tube.

Alfery, U.S. Pat. No. 6,729,325, discloses a perilaryngeal oral airway and supraglottic airway which is capable of acting as an entotracheal tube guide and which seats deep in a patent's hypopharynx to prevent the soft tissue of the glottis and epiglottis from obstructing the airway.

Insler et al., U.S. Pat. No. 5,588,424, describes a bronchial blocker endotracheal apparatus employing two lumen. The principal lumen serves to enter and create a cuffed seal within the trachea to ventilate one or both lungs. The second tube also enters the trachea, is permitted to pass below the first lumen's cuff and serves the function of slidably receiving an endobrochial blocker (having a cuffed catheter) that can be positioned into the right or the left bronchus and the cuff inflated to occlude the selected bronchus.

U.S. Pat. Nos. 5,353,787 and 5,253,643, both to Price, disclose an standard endotracheal tube device that is demountably attachable to an oral airway device.

White et al., U.S. Pat. No. 4,774,945, discloses a naso-intubation system employing a speech facilitator tube and valve to permit the patient to speak while intubated.

In Scarberry, U.S. Pat. No. 4,351,330, an emergency resuscitation apparatus is provided by an endotracheal tube having a tracheal obturator and a second expandable cuff for sealing against the pharyngeal tissues to provide an alternate sealing means for respiratory fluids if the blind intubation is not successful. Scarberry, U.S. Pat. No. 4,231,365, describes a dual lumen emergency internal defibrillation apparatus.

Dryden, U.S. Pat. No. 4,256,099 and Elam U.S. Pat. No. 4,090,518 also describe a dual lumen resuscitation systems.

Frankel, EPO 0 230 790 discloses an endotracheal tube that is inserted into the patient along a tracked guide located on a flexible tube such as an esophageal tube.

Klepper, U.S. Pat. No. 6,460,540 discloses an endotracheal tube sump assembly attachable to the outside of the endotracheal tube.

Bowden et al., U.S. Pat. No. 6,374,827 discloses a dual lumen tracheo-esophageal tube and ventilator for pneumatic cardiopulmonary resuscitation.

Gadberry, et al., U.S. Pat. No. 6,461,363 discloses the use of a ratchet gear and ratchet pawl system formed on engaging surfaces of finger grips on a surgical clamping tool. Adjustable ratchet clamps, such as the adjustable nylon ratchet clamps available on the worldwide web from ElectricalBasics.com, are known in the art. Hook and loop reclosable cable tie wraps are also known in the art and are offered and sold by Leviton (levitonproducts.com).

However, in contrast, none of the above prior art provide an improved device and method to safely facilitate the process of placing within a patient, an enteral tube after endotracheal intubation.

BRIEF SUMMARY OF THE INVENTION

To address the forgoing problems, the present invention teaches a combination intubation device comprising: an endotracheal tube with a substantially circular cross-section, an outside diameter, an inside diameter, a proximal end and a distal end; an inflatable cuff for achieving a seal with an inner wall of the trachea of the patient positioned generally toward the distal end of the endotracheal tube; and a catheter to guide the path of an enteral tube. In a preferred embodiment, the endotracheal tube is capable of defining an arcuate path in a first geometric plane between its proximal end and its distal end to facilitate introduction of the tube into the trachea of a patient. The endotracheal tube has a wall thickness defined as the space between said outside diameter and said inside diameter. The arcuate path, when so defined, has a concave or anterior side and a convex or posterior side substantially opposite the concave side. The endotracheal tube, when so defined in the arcuate path, has a concave or anterior side and a convex or posterior side substantially opposite said concave side.

The inflatable cuff is in fluid communication with an inflation port positioned generally toward the proximal end of the endotracheal tube. The catheter preferably has a substantially circular cross-section, an outside diameter, and an inside diameter suitable to facilitate the smooth movement of the enteral tube therethrough. The enteral tube has an outside diameter of sufficient size to permit its movement through the catheter inside diameter. The catheter has a wall thickness defined as the space between said outside diameter and said inside diameter, and a length defined by a proximal end and a distal end. The catheter preferably has a first side capable of being attached to the endotracheal tube along the length of the catheter. The length of the catheter preferably extends along only a portion of the length of the endotracheal tube. The catheter has a second side substantially opposite said catheter first side. The outside diameter of the endotracheal tube has a first edge along the concave side of the defined arcuate path and a second edge along the convex side of the defined arcuate path. The distal end of the catheter is positioned to facilitate the introduction of the enteral tube into the esophagus of the patient.

The endotracheal tube and catheter can preferably be constructed of a flexible, generally transparent material. In a preferred embodiment, the first side of the catheter is attached to the endotracheal tube along substantially the entire length of the catheter. The catheter is designed to permit entry of any variety of enteral tubes, such as, an orogastric tube. The distal end of the catheter is preferably positioned to direct the path of the enteral tube posteriorly toward the esophagus of the patient. The distal end of the catheter can also be preferably positioned to direct the path of the enteral tube into the gastrointestinal tract of the patient. The distal end of the catheter can be fashioned with a diagonal cut to facilitate the introduction of the enteral tube into the esophagus of the patient.

The positioning of the catheter relative to the endotracheal tube can take on any number of configurations, including, co-axial, helical, semi-helical, integrated, side-by-side, etc. For example, the proximal end of the catheter can be preferably positioned generally within the first plane and the distal end of the catheter positioned generally within the first plane. In another preferred embodiment, the proximal end of the catheter is positioned generally within the first plane and the distal end of the catheter is positioned generally outside of the first plane. In another preferred embodiment, the proximal end of the catheter is positioned generally outside of the first plane and the distal end of the catheter is positioned generally within the first plane. Also, the proximal end of the catheter can be positioned generally outside of the first plane and the distal end of the catheter can be positioned generally outside of the first plane.

In a preferred embodiment, the arcuate path concave or anterior side is generally pointing in a direction away from the patient's vertebra when the endotracheal tube is inserted into the patient, and the arcuate path convex or posterior side is generally pointing toward the patient's vertebra when the endotracheal tube is inserted into the patient. The outside diameter of the endotracheal tube has a first edge along the first side of the arcuate path and a second edge along the second side of the arcuate path. The proximal end of the catheter can be preferably positioned generally within the first plane, the catheter defining a substantially linear path along the second edge of the outside diameter of the endotracheal tube. In another embodiment, the proximal end of the catheter can also be positioned generally outside the first plane, the catheter defining a substantially partial-spiral path around the outside diameter of the endotracheal tube to position the distal end of the catheter in the first plane proximate the second edge of the outside diameter of the endotracheal tube. In a preferred embodiment, the substantially partial spiral path traverses approximately 90-degrees along the outside diameter of the endotracheal tube. In another embodiment, the proximal end of the catheter is side-by-side the endotracheal tube in a second plane substantially normal to the first plane; the distal end of the catheter can be side-by-side the endotracheal tube in a second plane substantially normal to the first plane.

In yet another preferred embodiment, the proximal end of the catheter is positioned generally outside said first plane, the catheter defining a substantially helical path around the outside diameter of said endotracheal tube. In yet another preferred embodiment, the proximal end of the catheter is positioned generally inside said first plane, the catheter defining a substantially helical path around the outside diameter of said endotracheal tube.

In another preferred embodiment of the present invention, the catheter of the present invention further comprises a fenestration along substantially the entire length of the catheter wall to facilitate the removal from the catheter of an enteral tube having previously been placed therethrough without the need to remove the enteral tube from the patient. The fenestration can be located along the outer diameter of the catheter substantially medially between the catheter first side and the catheter second side. In a preferred embodiment, the fenestration is a membrane-like material capable of tearing open sufficient to permit the enteral tube to be pulled substantially laterally through the membrane until the enteral tube is without the catheter. In another preferred embodiment, the fenestration comprises a slit through the entire thickness of the catheter wall thickness along the entire length of the catheter sufficient to permit the enteral tube to be pulled substantially laterally through the slit until the enteral tube is without the catheter. In one embodiment, the slit is maintained in a substantially closed position with a removable strip of tape placed over the slit on the outside diameter of the catheter. The slit preferably has a width of lesser size than the outer diameter of the enteral tube, for example, between ¼ and ½ the size of the outer diameter of the enteral tube.

The catheter can be removably attached to the endotracheal tube. For example, in a preferred embodiment, the catheter further comprises an expandable sleeve connected to the outside diameter of the catheter for attaching the catheter to the endotracheal tube, the expandable sleeve capable of snugly sliding over the outside diameter of the endotracheal tube. The expandable sleeve can further comprise a stretchable material. The sleeve can be connected along a portion of, or substantially the entire length of, the outside diameter of the catheter, and can further comprise one or more expandable sleeves. In another preferred embodiment, the expandable sleeve further comprises one or more closable and reopenable closures connected along the outside diameter of the catheter, the closures being capable of wrapping around the outside diameter of the endotracheal tube to secure the catheter to the endotracheal tube.

In another preferred embodiment, the catheter is fixably attached to the endotracheal tube using any number of methods known in the art, such as, for example and without limitation, extrusion molding, gluing, heat welding, chemical bonding, ring clips, tape, hook and loop fasteners, such as those sold under the VELCRO® brand, mating channels, mated compression fittings, fasteners, clamps and encapsulation with shrink wrap. In one embodiment, the catheter is fixably attached to the endotracheal tube so that a seam is created between the outside diameter of the catheter and the outside diameter of the endotracheal tube, the seam having a length that is adjustable.

In yet another preferred embodiment, the catheter can be removably attached to the endotracheal tube using a variety of methods known in the art. For example, the use of tape, hook and loop fasteners, such as those sold under the VELCRO® brand, mating channels, mated compression fittings, fasteners, clamps and the like can be employed to removably attach the catheter. For example, in a preferred embodiment, the catheter and the endotracheal tube contain mated linear tracks for slidably attaching (or removing) the outer diameter of the catheter to the outer diameter of the endotracheal tube. The catheter can also be slidably attached to the endotracheal tube, where the catheter has one or more cylindrical tubes fixably attached to the anterior side of the catheter, these cylindrical tube(s) being substantially co-axially aligned with each other, and the cylindrical tube(s) having a cross-sectional shape substantially similar to the cross-section of the endotracheal tube, an outside diameter, and an inside diameter suitable to facilitate the frictional movement of the endotracheal tube therethrough, a proximal end and a distal end.

The intubation device of the present invention can also be constructed in a manner that provides unitary construction. For example, the catheter and endotracheal tube can be fully integrated into unitary device. Also, the catheter can comprise a conduit located within the wall of the endotracheal tube.

The intubation device of the present invention can also preferably further comprise: a first section proximate the proximal end of the endotracheal tube wherein the proximal end of the catheter is maintained external to the endotracheal tube, a second section between the proximal and distal ends of the endotracheal tube wherein the catheter is maintained within the endotracheal tube, and a third section toward the distal end of the endotracheal tube wherein the distal end of the catheter is maintained external to the endotracheal tube. In another preferred embodiment, the intubation device of the present invention further comprises: a first section proximate the proximal end of the endotracheal tube wherein the proximal end of the catheter is maintained within the wall of the endotracheal tube, the proximal end of the catheter being flush with the outside diameter of the endotracheal tube and remaining capable of having the enteral tube pass therethrough; a second section between the proximal and distal ends of the endotracheal tube wherein the catheter is maintained within the endotracheal tube; and a third section toward the distal end of the endotracheal tube wherein the distal end of the catheter is maintained within the wall of the endotracheal tube, the distal end of the catheter being flush with the outside diameter of the endotracheal tube and remaining capable of having the enteral tube pass therethrough.

In another preferred embodiment, the intubation device of the present invention preferably further comprises an endotracheal tube axis located in the distal portion of the endotracheal tube, the endotracheal tube axis being substantially aligned with the axis of the patient's trachea when the distal end of the endotracheal tube is placed within the patient's trachea; a first catheter zone located between the proximal and distal ends of the catheter, wherein the catheter has a first catheter axis that is substantially parallel to the endotracheal tube axis; and a second catheter zone located proximate the distal end of the catheter wherein the catheter has a second catheter axis that diverges from the first catheter axis. In a preferred embodiment, the second catheter axis diverges from the first catheter axis to direct the path of the enteral tube posteriorly toward the esophagus of the patient. In another preferred embodiment, the second catheter axis diverges from the first catheter axis to form an angle between both axes to optimally align the distal end of the catheter for directing the path of the enteral tube posteriorly toward the esophagus of the patient. The angle can preferably be between about 15 degrees and 60 degrees.

In another preferred embodiment of the present invention, the intubation device further comprises a malleable stylet for use in shaping the device. In one example, the endotracheal tube (and/or the catheter) further comprises a malleable stylet for use in shaping the endotracheal tube (and/or the catheter), the stylet having a distal end and a proximal end. The stylet can employ fiber optics capable of transmitting an optical image signal from the distal end of the stylet to a display device connected to the proximal end of the stylet. In a preferred embodiment, the stylet is integrated into the endotracheal tube (and/or catheter), such as by being built into the wall of the endotracheal tube (and/or catheter). Alternatively, the stylet is insertable into and removable from the inside diameter of the endotracheal tube and/or catheter.

In another preferred embodiment, the endotracheal tube (and/or catheter) further comprises one or more strands of a flexible, memory retaining material capable of being manipulated to facilitate the defining of the arcuate path or otherwise to facilitate the shaping of the endotracheal tube and/or catheter. Additionally, the endotracheal tube of the present invention may contain a manual curvature adjustment ring to likewise facilitate the defining of the arcuate path or otherwise to facilitate the shaping of the endotracheal tube.

In another preferred embodiment of the present invention, there is disclosed a combination medical device comprising: an endotracheal tube with a substantially circular cross-section, an outside diameter, an inside diameter, a proximal end and a distal end; and a catheter to guide the path of an enteral tube. The endotracheal tube defines an arcuate path in a first plane between its proximal end and its distal end to facilitate introduction of the tube into the trachea of a patient. The endotracheal tube employs an inflatable cuff for achieving a seal with an inner wall of the trachea of the patient positioned generally toward the distal end of the endotracheal tube, the inflatable cuff being in fluid communication with an inflation port positioned generally toward the proximal end of the endotracheal tube. The catheter has a substantially circular cross-section, an outside diameter, and an inner diameter suitable to facilitate the smooth movement of the enteral tube therethrough, and a length defined by a proximal end and a distal end. The catheter is attached to the endotracheal tube along substantially the entire length of said catheter, the proximal end of the catheter being positioned generally outside the first plane, the length of the catheter extending along only a portion of the length of the endotracheal tube. In this embodiment, the catheter defines a substantially partial-spiral path around the outside diameter of the endotracheal tube to position the distal end of the catheter in the first plane, the distal end of the catheter having a diagonal cut at the end to facilitate the introduction of the enteral tube into the esophagus of the patient. The catheter of this embodiment can also comprise a fenestration along substantially the entire length of the catheter wall to facilitate the removal from the catheter of an enteral tube having previously been placed therethrough without the need to remove the enteral tube from the patient.

The endotracheal tube of the present invention can also employ markings to assist medical personnel in ascertaining placement and positioning of the device.

In yet another preferred embodiment of the present invention, there is disclosed an endotracheal intubation device comprising:

a substantially circular cross-section, an outside diameter, an inside diameter, a proximal end, a distal end, a wall thickness defined as the space between the outside diameter and the inside diameter;

the endotracheal intubation device capable of defining an arcuate path in a first geometric plane between its proximal end and its distal end to facilitate introduction of the tube into the trachea of a patient, the arcuate path, when so defined, having a concave side and a convex side substantially opposite said concave side, the endotracheal tube, when so defined in the arcuate path, having a concave side and a convex side substantially opposite said concave side, a malleable stylet for use in shaping said endotracheal intubation device;

the stylet having a distal end and a proximal end and being integrated into said wall thickness; and an inflatable cuff for achieving a seal with an inner wall of the trachea of the patient positioned generally toward the distal end of said endotracheal intubation device, the inflatable cuff being in fluid communication with an inflation port positioned generally toward the proximal end of said endotracheal tube.

In this embodiment, the stylet can further comprise one or more strands of a flexible, memory retaining material capable of being manipulated to facilitate the defining of the arcuate path. Additionally, if desired, this intubation device can employ integrated fiber optics capable of transmitting an optical image signal from the distal end to a display device.

In yet another preferred embodiment of the present invention, there is described a method of intubating a patient comprising the steps of: (a) providing an intubation device in accordance with embodiments of the present invention; (b) inserting into the oral cavity of a patient the intubation device oriented such that the distal end of the endotracheal tube enters first; (c) orienting the distal end of the endotracheal tube with the patient's trachea; (d) inserting the distal end of the endotracheal tube into the patient's trachea; (e) inflating the inflatable cuff by administering a source of air into the inflation port; and ventilating the patient through the endotracheal tube. A preferred embodiment includes the additional step of directing a desired enteral tube into the proximal end of the catheter, through the catheter, out the distal end of the catheter and into the desired location of the patient. Another preferred embodiment of this method includes the additional step of removing the intubation device without removing said enteral tube from said desired location within the patient.

When the catheter of the intubation device of the present invention includes the fenestration feature, a preferred embodiment of the present inventive method can also include the additional steps of: deflating the inflatable cuff of the endotracheal tube; maintaining the enteral tube in its desired location while withdrawing the intubation device from the patient's oral cavity; and maintaining the enteral tube in its desired location while directing the enteral tube through the fenestration.

When the catheter of the intubation device of the present invention includes an integrated, malleable stylet for use in shaping the intubation device, a preferred embodiment of the present inventive method can also include the additional step of: shaping the intubation device prior to inserting the device into the oral cavity of a patient so that the shape of the intubation device facilitates the insertion of the device into the oral cavity of the patient.

When the catheter of the intubation device of the present invention includes an integrated array of fiber optics capable of transmitting an optical image signal from the distal end of the device to a display device external to the patient, a preferred embodiment of the present inventive method can also include the additional step of: viewing the display of the fiber optics image signal on the display device while inserting the intubation device into the patient to facilitate placement of the intubation device.

In yet another preferred embodiment of the present invention there is disclosed a medical catheter device, attachable to an endotracheal tube having a proximal end and a distal end, for guiding the path of an enteral tube into the esophagus of a patient. The catheter device comprises a catheter conduit having a proximal end with a proximal end opening for receiving the enteral tube, and a distal end opposite the proximal end having a distal end opening opposite the proximal end opening. The conduit has a length defined as the distance between the proximal end and the distal end; an outer wall surface; an inner wall surface defining a catheter conduit interior space suitably sized to permit the passage of the enteral tube therethrough; and a catheter conduit wall thickness defined as the space between the outer wall surface and the inner wall surface.

The catheter conduit interior space is further defined as the space between the proximal conduit opening, the distal conduit opening and the conduit inner wall surface. The catheter conduit has a conduit proximal end axis which extends axially from and into the proximal end of the catheter conduit. The catheter conduit has a conduit distal end axis which extends axially from and into the distal end of the catheter conduit. The catheter device also comprises a proximal end clip attached to the catheter conduit proximate the proximal end of the catheter conduit for receiving and removably attaching a portion of the endotracheal tube near the proximal end of the endotracheal tube, the proximal end clip having a first proximal clip end oriented toward the catheter conduit proximal end and a second proximal clip end oriented toward the catheter conduit distal end. The proximal end clip has a proximal end clip axis which extends axially through the proximal end clip from the proximal end clip first end toward the proximal end clip second end. The catheter device also comprises a distal end clip attached to the catheter conduit proximate the distal end of the catheter conduit for receiving and removably attaching another portion of the endotracheal tube located toward the distal end of the endotracheal tube, the distal end clip having a first distal clip end oriented toward the catheter conduit proximal end and a second distal clip end oriented toward the catheter conduit distal end. The distal end clip has a distal end clip axis which extends axially through the distal end clip from the distal end clip first end toward the distal end clip second end.

The catheter conduit can be configured to be substantially tubular in shape. The catheter conduit can be configured to be substantially linear along its length or curved along its length. Preferably, the catheter conduit is a flexible. In one embodiment, the conduit proximal end axis is aligned with the conduit distal end axis. In another embodiment, the conduit proximal end axis intersects with the conduit distal end axis to form a conduit angle. The conduit angle preferably ranges between about 0 degrees and about 30 degrees. In a preferred embodiment, the conduit angle is about 10 degrees.

In one embodiment, of the catheter device, the proximal end clip comprises a c-shaped hollow proximal clip tube capable of clipping over and gripping the outside surface of the portion of the endotracheal tube near the proximal end of the endotracheal tube. The distal end clip comprises a c-shaped hollow distal clip tube capable of clipping over and gripping the outside surface of the portion of the endotracheal tube near the distal end of the endotracheal tube. In one embodiment, the proximal end clip axis is aligned with the distal end clip axis, and in another embodiment, the proximal end clip axis intersects with the distal end clip axis to form a clip angle. The clip angle preferably ranges between about 0 degrees and about 30 degrees. In one embodiment, the clip angle is preferably about 10 degrees. In another embodiment, of the catheter device, the proximal end clip axis is substantially parallel with the conduit proximal end axis. In another embodiment, the distal end clip axis is substantially parallel with the conduit distal end axis. In another embodiment, the proximal end clip axis is not substantially parallel with the conduit proximal end axis. In yet another embodiment, the distal end clip axis is not substantially parallel with the conduit distal end axis.

The proximal end clip can also serve as a bite block device to inhibit the potential collapse, caused by patient biting, of the catheter conduit or the endotracheal tube contained therein.

In yet another embodiment, the catheter device can employ an adjustable locking mechanism to lock the catheter conduit into a desired position relative to the endotracheal tube. In one such embodiment, the locking mechanism comprises an adjustable locking ratchet pawl type clamp in axial alignment with the first end of the proximal end clip and capable of receiving the endotracheal tube so that the ratchet clamp can lock the catheter device into the desired position. In another embodiment, the locking mechanism comprises an adjustable locking strap mechanism in axial alignment with the first end of the proximal end clip and capable of receiving the endotracheal tube so that the ratchet clamp can lock the catheter device into the desired position. The locking mechanism of either embodiment can also be released or unlocked.

The catheter device can also further comprise an endotracheal tube having a portion of its distal end attached to the distal end of the catheter and having a portion of its proximal end attached to the proximal end of the catheter. In one such embodiment, the endotracheal tube has a portion of its distal end attached to the catheter distal end clip and has a portion of its proximal end attached to the catheter proximal end clip.

The catheter device can further comprise a malleable stylet for use in shaping the catheter conduit, the stylet having a distal end and a proximal end. If desired, the stylet can employ fiber optics capable of transmitting an optical image signal from the distal end of the stylet to a display device connected to the proximal end of the stylet. The stylet can be is integrated into the catheter conduit such as by building it into the wall of the catheter conduit. Also a separate stylet can be inserted into and removed from the interior space of the catheter conduit.

The catheter conduit may further comprise one or more strands of a flexible, memory retaining material capable of being manipulated to facilitate shaping of the catheter conduit.

In another embodiment of the present invention there is described a combination medical device comprising:
(a) an endotracheal tube with a substantially circular cross-section, an outside diameter, an inside diameter, a proximal end and a distal end, the endotracheal tube defining an arcuate path in a first plane between its proximal end and its distal end to facilitate introduction of the tube into the trachea of a patient, the endotracheal tube also having an inflatable cuff for achieving a seal with an inner wall of the trachea of the patient positioned generally toward the distal end of the endotracheal tube, the inflatable cuff being in fluid communication with an inflation port positioned generally toward the proximal end of the endotracheal tube, and
(b) a catheter device, attachable to the endotracheal tube having a proximal end and a distal end, for guiding the path of an enteral tube into the esophagus of a patient, the catheter device comprising:
  i. a catheter conduit comprising a proximal end with a proximal end opening for receiving the enteral tube, and a distal end opposite the proximal end having a distal end opening opposite the proximal end opening; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit;
  ii. a proximal end clip attached to the catheter conduit proximate the proximal end of the catheter conduit for receiving and removably attaching a portion of the endotracheal tube near the proximal end of the endotracheal tube, the proximal end clip having a first proximal clip end oriented toward the catheter conduit proximal end and a second proximal clip end oriented toward the catheter conduit distal end; wherein the proximal end clip has a proximal end clip axis which extends axially through the proximal end clip from the proximal end clip first end toward the proximal end clip second end; and
  iii. a distal end clip attached to the catheter conduit proximate the distal end of the catheter conduit for receiving and removably attaching another portion of the endotracheal tube located toward the distal end of the endotracheal tube, the distal end clip having a first distal clip end oriented toward the catheter conduit proximal end and a second distal clip end oriented toward the catheter conduit distal end; wherein the distal end clip has a distal end clip axis which extends axially through the distal end clip from the distal end clip first end toward the distal end clip second end.

There is also described and disclosed herein a method of intubating a patient comprising the steps of:
(a) providing a combination intubation device as described and disclosed herein;
(b) inserting into the oral cavity of a patient the intubation device oriented such that the distal end of the endotracheal tube enters first;
(c) orienting the distal end of the endotracheal tube with the patient's trachea;
(d) inserting the distal end of the endotracheal tube into the patient's trachea;
(e) inflating the inflatable cuff by administering a source of air into the inflation port; and
(f) ventilating the patient through the endotracheal tube.

Additionally, this method can comprise the additional step of:
(g) directing a desired enteral tube into the proximal end of the catheter, through the catheter, out the distal end of the catheter and into the desired location of the patient.

In carrying out this method, any endotracheal tube can be used. Typically, most endotracheal tubes on the market will have a substantially circular cross-section, an outside diameter, an inside diameter, a proximal end and a distal end. The endotracheal tube can further define an arcuate path in a first plane between its proximal end and its distal end to facilitate introduction of the tube into the trachea of a patient, the endotracheal tube also having an inflatable cuff for achieving a seal with an inner wall of the trachea of the patient positioned generally toward the distal end of the endotracheal tube, the inflatable cuff being in fluid communication with an inflation port positioned generally toward the proximal end of the endotracheal tube, and a catheter device, attachable to the endotracheal tube having a proximal end and a distal end, for guiding the path of an enteral tube into the esophagus of a patient.

The catheter device used in this method, can include those such as described herein, for example: a catheter conduit comprising a proximal end with a proximal end opening for receiving the enteral tube, and a distal end opposite the proximal end having a distal end opening opposite the proximal end opening; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit; a proximal end clip attached to the catheter conduit proximate the proximal end of the catheter conduit for receiving and removably attaching a portion of the endotracheal tube near the proximal end of the endotracheal tube, the proximal end clip having a first proximal clip end oriented toward the catheter conduit proximal end and a second proximal clip end oriented toward the catheter conduit distal end; wherein the proximal end clip has a proximal end clip axis which extends axially through the proximal end clip from the proximal end clip first end toward the proximal end clip second end; and a distal end clip attached to the catheter conduit proximate the distal end of the catheter conduit for receiving and removably attaching another portion of the endotracheal tube located toward the distal end of the endotracheal tube, the distal end clip having a first distal clip end oriented toward the catheter conduit proximal end and a second distal clip end oriented toward the catheter conduit distal end; wherein the distal end clip has a distal end clip axis which extends axially through the distal end clip from the distal end clip first end toward the distal end clip second end. The proximal end clip can also further comprise a locking mechanism such as those described herein for securing or locking the catheter device relative to the endotracheal tube.

BRIEF DESCRIPTION OF THE SEVERAL VIEWS OF THE DRAWINGS

FIG. 2b illustrates a substantially right side perspective view of the intubation device of FIG. 2a (rotated partially counterclockwise about the longitudinal axis of the device) according to a preferred embodiment of the present invention.

FIG. 2c illustrates a substantially underside (posterior) perspective view of the intubation device of FIG. 2a (rotated ninety degrees counterclockwise about the longitudinal axis of the device shown in FIG. 2b) according to a preferred embodiment of the present invention.

FIG. 2d illustrates a substantially left side perspective view of the intubation device of FIG. 2a (rotated ninety degrees counterclockwise about the longitudinal axis of the device shown in FIG. 2c) according to a preferred embodiment of the present invention.

FIG. 2h illustrates a geometric (coronal) plane view of the intubation device taken along the coronal cutting plane line 2h-2h of FIG. 2a.

FIG. 2i illustrates a geometric (saggital) plane view taken along the saggital cutting plane line 2i-2i of FIG. 2a.

FIG. 3a is a cross sectional view of one preferred embodiment of the present invention taken across line 3a-h-3a-h of FIG. 2a.

FIG. 3b is a cross sectional view of one preferred embodiment of the present invention taken across line 3a-h-3a-h of FIG. 2a.

FIG. 3c is a cross sectional view of one preferred embodiment of the present invention taken across line 3a-h-3a-h of FIG. 2a.

FIG. 3e is a cross sectional view of one preferred embodiment of the present invention taken across line 3a-h-3a-h of FIG. 2a.

FIG. 3f a cross sectional view of is one preferred embodiment of the present invention taken across line 3a-h-3a-h of FIG. 2a.

FIG. 3g is a cross sectional view of one preferred embodiment of the present invention taken across line 3a-h-3a-h of FIG. 2a.

FIG. 3h is a cross sectional view of one preferred embodiment of the present invention taken across line 3a-h-3a-h of FIG. 2a.

FIG. 6a illustrates a perspective top side (anterior) view of an intubation device according to another preferred embodiment of the present invention.

FIG. 6b illustrates a substantially right side perspective view of the intubation device of FIG. 6a (rotated partially counterclockwise about the longitudinal axis of the device) according to a preferred embodiment of the present invention.

FIG. 17A-1 illustrates a close-up of cross sectional detail 17A-1 of FIG. 17A.

FIG. 19 illustrates a distal end view of the catheter shown in FIG. 17.

FIG. 20 illustrates a proximal end view of the catheter shown in FIG. 17.

DETAILED DESCRIPTION OF THE INVENTION

Figure 1:
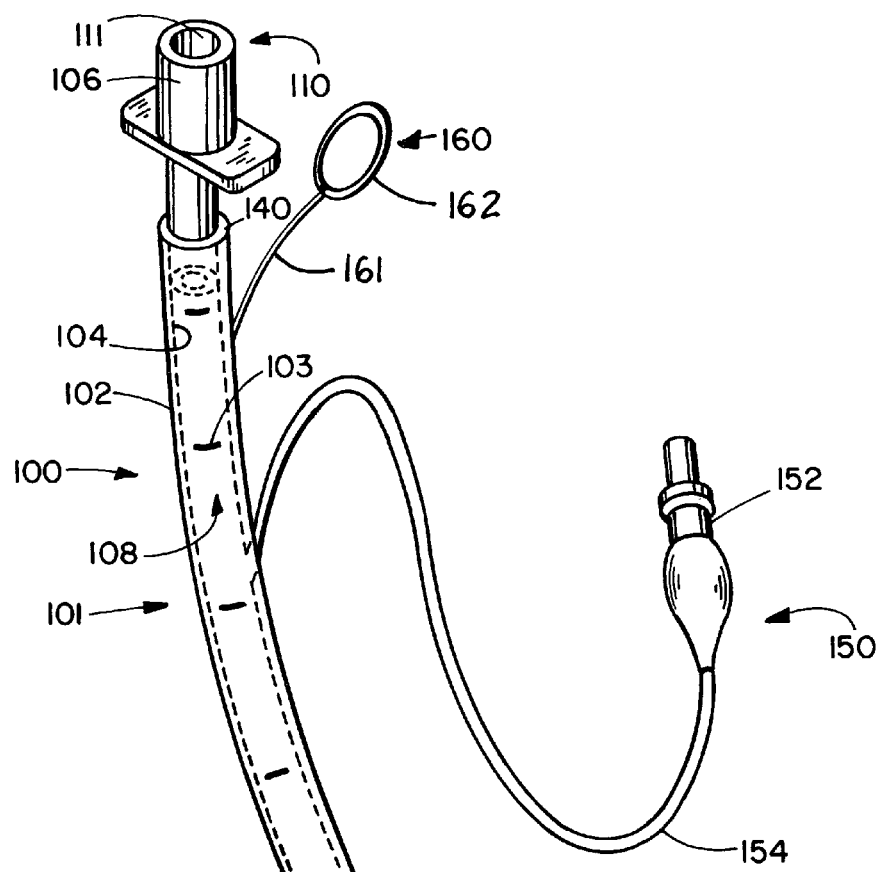
FIG. 1 shows a perspective view of a prior art endotracheal tube.
Figure 1:
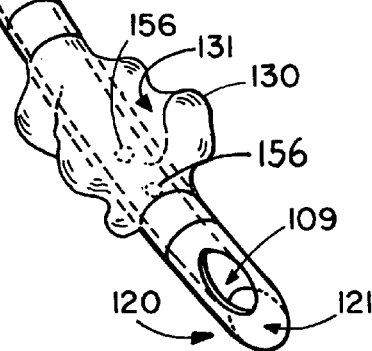

Referring now to FIG. 1, there is shown a representative endotracheal tube 100 known in the prior art having a lumen 101 having a substantially circular cross-section, an outside wall 102 having an outside wall diameter, an inside wall 104 having an inside wall diameter, a proximal end 110 and a distal end 120. The endotracheal tube 100 employs at its proximal end 110 a connector device 106 for connecting to a means of ventilation (not shown) such as ventilation source, bag valve and the like for providing a source of air to the patient's lungs through the internal conduit 108 within the lumen 101 of the endotracheal tube 100. The tube 100 has a proximal opening 111. At the distal end 120 of the endotracheal tube 100 the tube is typically bevel-shaped to facilitate introduction into the patient's trachea. Also shown in the distal region of the tube 100 is the distal opening 121 and a "Murphy's eye" suction opening 109 for suctioning fluids from below the cuff. The proximal opening 111 and the distal opening 121 are in fluid communication with each other. An inflatable balloon cuff 130 for achieving a seal with an inner wall of the trachea of the patient is positioned generally toward the distal end 120 of the endotracheal tube 100. The endotracheal tube lumen 101 has a wall thickness 140 defined as the space between the outside diameter 102 and the inside diameter 104. The inflatable cuff 130 is in fluid communication with an inflation port assembly 150 positioned generally toward the proximal end 110 of the endotracheal tube 100.

The inflation port assembly 150 comprises a pilot balloon and valve 152 for use in providing air to or releasing air from the inflatable cuff 130 via cuff inflation tube 154 and its opening 156 into the cuff interior 131. The pilot balloon and valve 152 are in fluid communication with the inflation tube 154 and the cuff interior 131. The cuff 130 is attached to the exterior of the lumen 101 in sealed fashion so that when air enters the interior space 131 of the cuff 130 through opening 156, the cuff will inflate until it is in sealed contact with the patient's tracheal walls. The endotracheal tube 100 can also include a manual curvature adjustment ring device 160 such as used in the Mallinckrodt® brand "endotrol tube". This ring structure 160 includes a wire 161 attached to a pull ring 162, wherein the wire 161 is, e.g., embedded within the wall 140 of the endotracheal tube 100 such that pulling on the ring 162 will cause the tube 100 to bend in a manner that facilitates insertion of the tube lumen 101 into the patient's trachea. The lumen 101 can be marked with visible and/or X-ray opaque (or radiopaque) stripes or markings 103 (generally shown), or other suitable means to facilitate the placement and orientation of the airway 100 and the location of the inflatable cuff 130 within the patient.

Referring now to FIGS. 2a-2g, there are shown novel dual lumen intubation devices 200 having an endotracheal lumen 201 with substantially circular cross-section, an outside wall 202 having an outside wall diameter, an inside wall 204 having an inside wall diameter, a proximal end 210 and a distal end 220. The endotracheal lumen component 201 of the intubation device 200 employs at its proximal end 210 a connector device 206 for connecting to a means of ventilation (not shown) such as ventilation source, ambu bag, bag valve and the like for providing a source of air to the patient's lungs through the internal conduit 208 within the endotracheal lumen 201 of the intubation device tube 200. The endotracheal lumen 201 has a proximal opening 211. At the distal end 220 of the endotracheal lumen 201 the lumen is typically bevel-shaped to facilitate introduction into the patient's trachea. Also shown in the distal region of the endotracheal lumen 201 is the distal opening 221 and a "Murphy's eye" suction opening 209 for suctioning fluids from below the cuff 230.

The proximal opening 211 and the distal opening 221 are in fluid communication with each other. An inflatable balloon cuff 230 for achieving a seal with an inner wall of the trachea of the patient (not shown) is positioned generally toward the distal end 220 of the endotracheal lumen 201. The endotracheal lumen 201 has a wall thickness 240 defined as the space between the outside diameter 202 and the inside diameter 204. The inflatable cuff 230 is in fluid communication with an inflation port assembly 250 positioned generally toward the proximal end 210 of the endotracheal lumen 201. The inflation port assembly 250 comprises, for example, a pilot balloon and valve 252 for use in providing air to or releasing air from the inflatable cuff 230 via cuff inflation tube 254 and its opening 256 into the interior space 231 of the cuff 230. The pilot balloon and valve 252 are in fluid communication with the inflation tube 254 and the cuff interior 231. The cuff 230 is attached to the exterior of the endotracheal lumen 201 in sealed fashion so that when air enters the interior space 231 of the cuff 230 through opening 256, the cuff will inflate until it is in sealed contact with the walls of the patient's trachea. The endotracheal lumen 201 can also include a manual curvature adjustment ring (not shown) such as used in the Mallinckrodt® brand "endotral tube" (see element 160 of FIG. 1 and associated text).

Figure 2A:
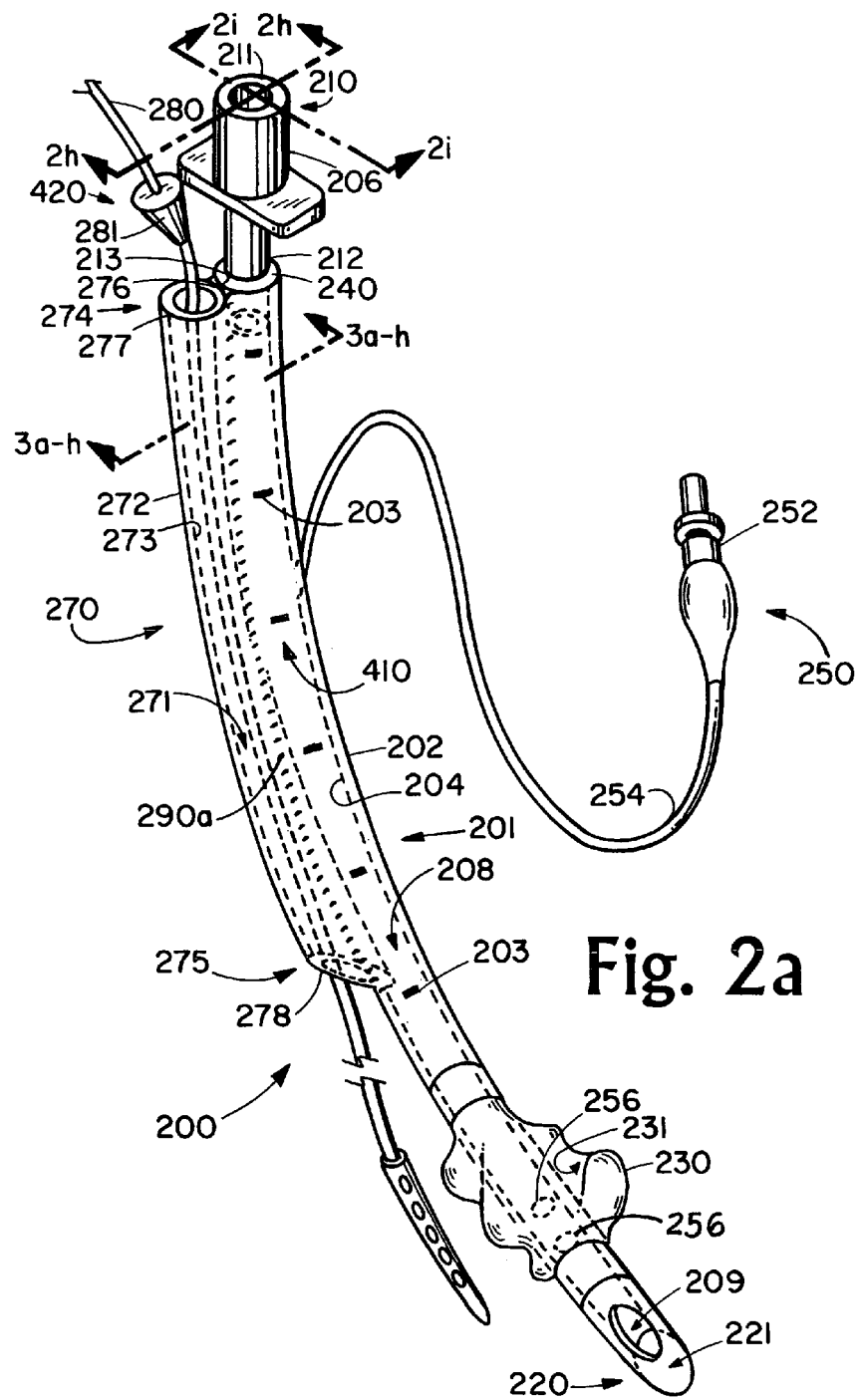
FIG. 2a illustrates a perspective top side (anterior) view of an intubation device according to a preferred embodiment of the present invention.
Figure 4:
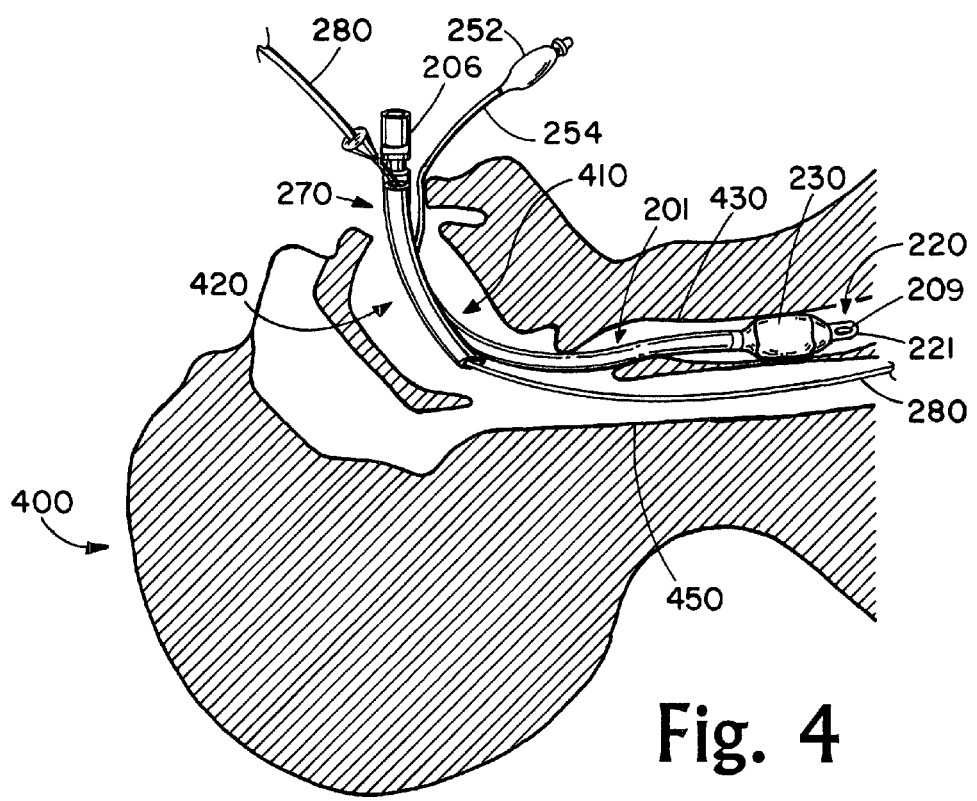
FIG. 4 is a side elevational, saggital view of a patient with an endotracheal intubation employing one preferred embodiment of the present intubation invention shown in perspective view.

FIG. 4 is a side cross sectional (saggital) view of a patient with an endotracheal intubation employing one preferred embodiment of the present intubation invention. Referring to FIG. 4, in conjunction with FIGS. 2a-2i, the endotracheal lumen 201 is capable of defining an arcuate path in a first geometric plane (or saggital plane) between its proximal end 210 and its distal end 220 to facilitate introduction of the endotracheal lumen 201 into the trachea 430 of a patient. The first geometric or saggital plane is depicted in FIG. 2i as the saggital cutting plane line of the lumen 201 taken from line 2i-2i of FIG. 2a. The arcuate path, when so defined, has a concave or anterior side 410 and a convex or posterior side 420 substantially opposite the concave side. The endotracheal lumen 201, when so defined in the arcuate path, has a concave or anterior side 410 and a convex or side 420 substantially opposite the concave side. Referring to FIG. 2h, there is shown a second geometric plane (or coronal plane) taken along the coronal cutting plane of the lumen 201 (line 2h-2h of FIG. 2a).

Attached (permanently, semipermanently, or removably) to the endotracheal lumen 201 is catheter 270 to guide the path of an enteral tube 280, such as the Bard® Nasogastric Sump Tube, into the esophagus 450 of the patient 400. The enteral tube 280 can be marked with visible and/or X-ray opaque (or radiopaque) stripes or markings (not shown), or other suitable means to facilitate the placement and orientation of the enteral tube 280 within the patient. The enteral tube 280 can employ as an option a locking device 281 to hold the enteral tube 280 in place relative to the catheter 270. The catheter 270 preferably has a substantially circular cross-section, an outside wall 272 defining an outside diameter, and an inside wall 273 defining an inside diameter suitable to facilitate the smooth movement of the enteral tube 280 therethrough.

The enteral tube 280 has an outside diameter of sufficient size to permit its movement through the catheter inside diameter 271. The catheter 270 has a wall thickness defined as the space between the outside diameter 272 and the inside diameter 273, and a length defined by a proximal end 274 and a distal end 275. The catheter 270 preferably has a first side 276 capable of being attached to the endotracheal lumen 201 along the length of the catheter 270. The length of the catheter 270 preferably extends along only a portion of the length of the endotracheal lumen 201. The catheter 270 has a second side 277 substantially opposite the catheter first side 276. The outside diameter of the endotracheal lumen 201 has a first edge 212 and a second edge 213. The distal end 275 of the catheter 270 is positioned to facilitate the introduction of the enteral tube 280 into the esophagus of the patient.

The endotracheal lumen 201 and/or the catheter 270 can be marked with visible and/or X-ray opaque (or radiopaque) stripes or markings 203 (generally shown), or other suitable means to facilitate the placement and orientation of the intubation device 200 and the location of the inflatable cuff 230 within the patient.

The endotracheal lumen 201 and catheter 270 can preferably be constructed of a flexible, generally transparent material. In a preferred embodiment, the first side 276 of the catheter 270 is attached to the endotracheal lumen 201 tube along substantially the entire length of the catheter 270. The catheter 270 is designed to permit entry of any variety of enteral tubes 280, such as, an orogastric tube. The distal end 275 of the catheter 270 is preferably positioned to direct the path of the enteral tube 280 posteriorly toward the esophagus 450 of the patient 400. The distal end 275 of the catheter 270 can also be preferably positioned to direct the path of the enteral tube 280 into the gastrointestinal tract of the patient (not shown). The distal end 275 of the catheter 270 can be fashioned with a diagonal cut 278 to facilitate the introduction of the enteral tube 280 into the esophagus of the patient.

The positioning of the catheter 270 relative to the endotracheal lumen 201 can take on any number of configurations, including, co-axial, helical, semi-helical, integrated, side-by-side, etc.

For example, in a preferred embodiment of the present invention, the proximal end of the catheter 274 is positioned generally outside of the first or saggital plane in the second or coronal plane and the distal end of the catheter 275 is positioned generally within the first or saggital plane such as depicted generally in FIGS. 2a-2d.

Figure 2E:
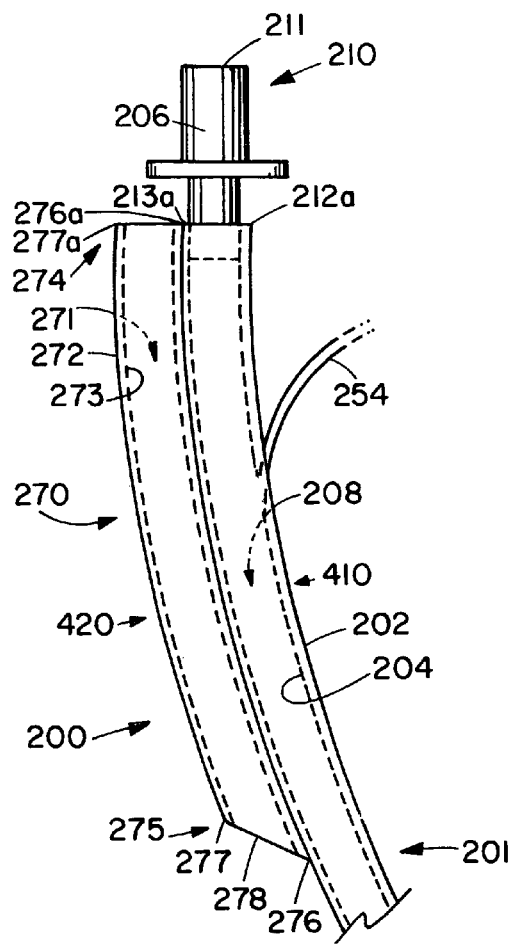
FIG. 2e illustrates a side view of an intubation device using a top-to-bottom catheter configuration according to a preferred embodiment of the present invention.

Referring to FIG. 2e, in another preferred embodiment, the proximal end of the catheter 274 can be preferably positioned generally within the first or saggital plane of the lumen 201 and the distal end of the catheter 275 also positioned generally within the first or saggital plane, such that both the catheter 274 and the lumen 201 are substantially top-to-bottom, lying within the same sattigal plane.

Figure 2F:
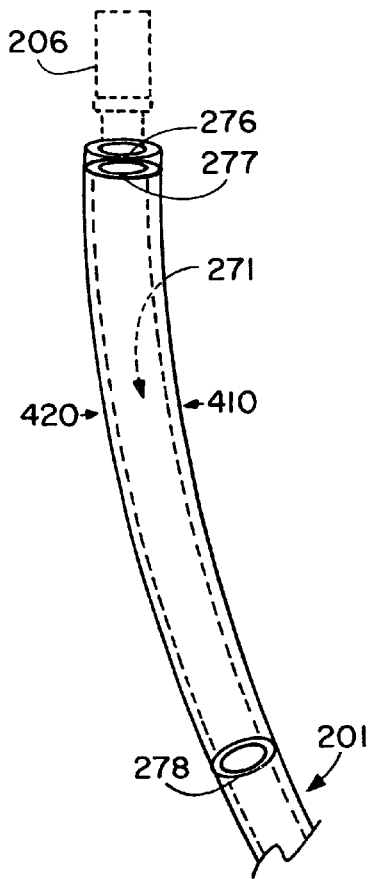
FIG. 2f illustrates a side view of an intubation device using a side-by-side catheter configuration according to a preferred embodiment of the present invention.
Figure 2G:
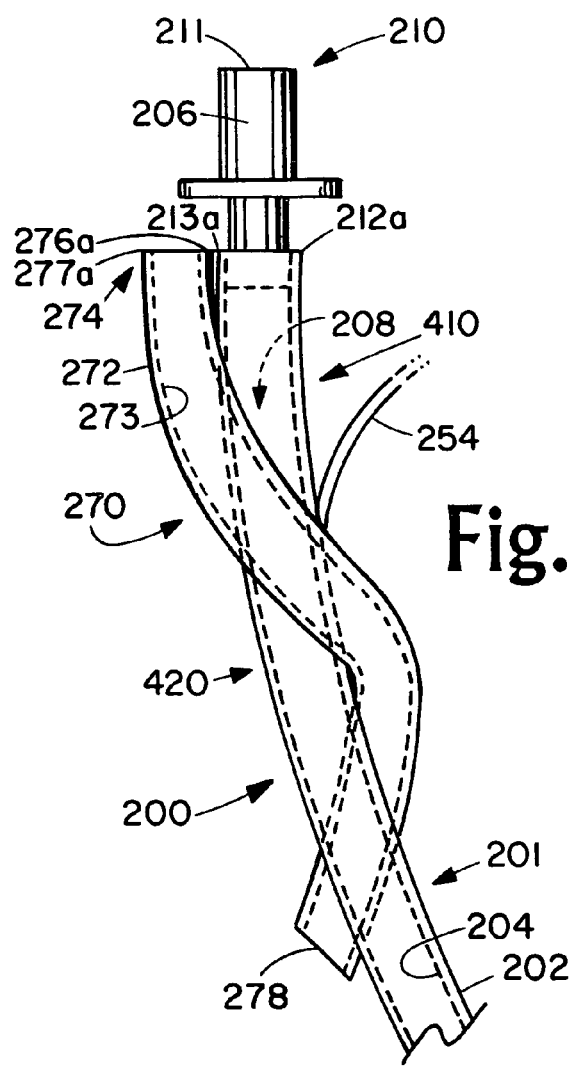
FIG. 2g illustrates a side view of an intubation device using a helical catheter configuration according to a preferred embodiment of the present invention.

In another preferred embodiment, the proximal end of the catheter 274 is positioned generally within the first or saggital plane of the lumen 201 and the distal end of the catheter 275 is positioned generally outside of the first or saggital plane in the second or coronal plane of the lumen 201, such as depicted in FIG. 2g.

Also, the proximal end of the catheter 274 can be positioned generally outside of the first or saggital plane in the second or coronal plane and the distal end of the catheter 275 can be positioned generally outside of the first or saggital plane in the second or coronal plane such as depicted in FIGS. 2e and 2g. The catheter 270 preferably has a first side 276a capable of being attached to the endotracheal lumen 201 along the length of the catheter 270. The length of the catheter 270 preferably extends along only a portion of the length of the endotracheal lumen 201. The catheter 270 has a second side 277a substantially opposite the catheter first side 276a The outside diameter of the endotracheal lumen 201 has a first edge 212a along the concave side of the defined arcuate path and a second edge 213a along the convex side of the defined arcuate path.

Furthermore, the catheter 270 could have a helical configuration relative to the endotracheal lumen 201 such as shown, for example, in FIG. 2g.

Referring to FIGS. 3a-3h, there are depicted some examples of the possible attachment relationships between the catheter 270 and the lumen 201. For example, the catheter and lumen can be attached by a zone of attachment or seam 290a, 290b, 290d, 290e, 290f, 290g that can be created by, e.g., heat welding, gluing, molding, or other means of attachment. The seam can be permanent, or can be designed to be temporary or adjustable in length. For example, the seam 290 could comprise a width of webbed material that could be cut or torn without destroying the integrity of interior spaces 271 and 208 of the catheter and lumen, respectively. A mated channel assembly 291, 292 (FIG. 3g) could also be employed to attach the catheter to the lumen. Additionally, the catheter and lumen could be attached using a clip assembly 293 comprising one or more C-shaped fingers 294, 295 that could snap over the outer diameter of the catheter and lumen (FIG. 3c), and if desired, the clip assembly 293 could be an integral part of lumen 201. Additionally, the cross-sectional profile of the intubation device could be substantially oval in shape as depicted in FIGS. 3b and 3d-f.

Referring again to FIG. 4 in conjunction with FIGS. 2a-2i, in a preferred embodiment, the arcuate path concave or anterior side 410 is generally pointing in a direction away from the patient's vertebra (not shown) when the intubation device 200 is inserted into the patient 400, and the arcuate path convex or posterior side 420 is generally pointing toward the patient's vertebra (not shown) when the intubation device 200 is inserted into the patient 400. The outside diameter 202 of the endotracheal lumen 201 has a first edge 212 along the first side of the arcuate path and a second edge 213 along the second side of the arcuate path. In one preferred embodiment, the proximal end of the catheter 274 can be preferably positioned generally within the first or saggital plane (one under the other) with the endotracheal tube 201), the catheter defining a substantially linear path along the second edge 213 of the outside diameter of the endotracheal tube 201 (e.g., FIG. 2e, 213a, 212a).

In another embodiment, the proximal end 274 of the catheter 270 can be positioned generally outside the first or saggital plane in the second or coronal plane (side-by-side with the endotracheal tube 201) (e.g., FIGS. 2a-2d), the catheter 270 defining a substantially partial-spiral path around the outside diameter 202 of the endotracheal tube 201 to position the distal end 275 of the catheter 270 in the first or saggital plane proximate the second edge 213 of the outside diameter 202 of the endotracheal tube 201. In a preferred embodiment, the substantially partial spiral path traverses approximately 90-degrees along the outside diameter of the endotracheal tube.

In another embodiment, the proximal end 274 of the catheter 270 is side-by-side the endotracheal tube 201 in a second plane substantially normal to the first plane; the distal end 275 of the catheter 270 can be side-by-side the endotracheal tube in the second plane substantially normal to the first plane (e.g., FIG. 2f).

In yet another preferred embodiment, the proximal end 274 of the catheter 270 is positioned generally outside the first plane, the catheter defining a substantially helical path around the outside diameter of the endotracheal tube 201.

In yet another preferred embodiment, the proximal end 274 of the catheter 270 is positioned generally inside the first plane, the catheter 270 defining a substantially helical path around the outside diameter 202 of the endotracheal tube 201 (e.g., FIG. 2g).

Figure 3A:
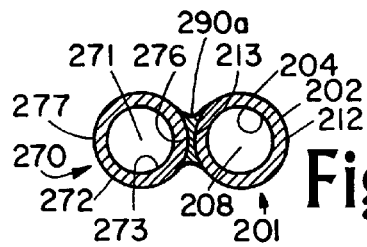
Figure 3B:
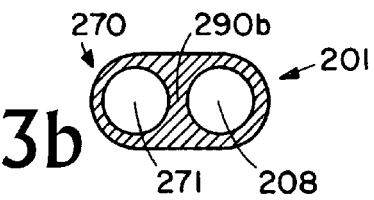
Figure 3C:
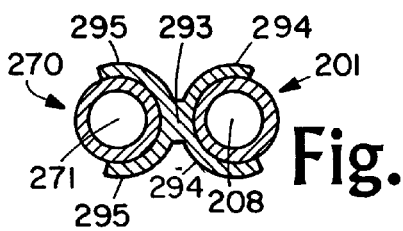
Figure 3D:
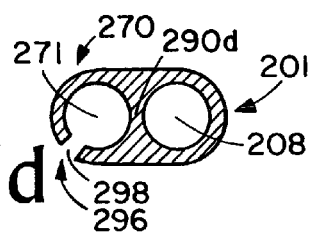
FIG. 3d is a cross sectional view of one preferred embodiment of the present invention taken across line 3a-h-3a-h of FIG. 2a or line 3d-3d of FIG. 8.
Figure 3E:
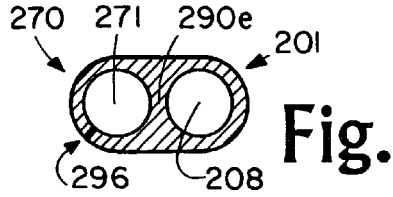
Figure 3F:
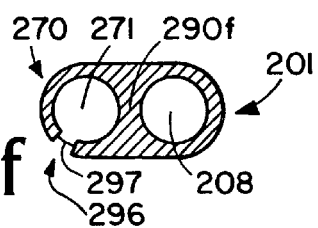
Figure 3G:
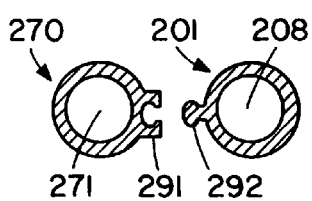
Figure 3H:
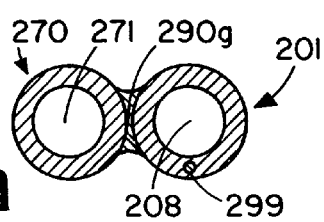

Referring also to FIG. 2a, FIGS. 3d-3f, and FIG. 8 in another preferred embodiment of the present invention, the catheter 270 of the present invention may further comprise a fenestration 296 along substantially the entire length of the catheter wall 272, 273 to facilitate the removal from the catheter of an enteral tube 280 having previously been placed therethrough without the need to remove the enteral tube from the patient 400. The fenestration 296 can be located along the outer diameter 272 of the catheter substantially medially between the catheter first side 276 and the catheter second side 277. In a preferred embodiment, the fenestration 296 is a membrane-like material 297 capable of tearing open sufficient to permit the enteral tube to be pulled substantially laterally through the membrane until the enteral tube 280 is without the catheter 270 (FIG. 3f).

In another preferred embodiment, the fenestration 296 comprises a slit 298 (e.g., FIG. 3d) through the entire thickness of the catheter wall thickness 272, 273 along the entire length of the catheter 270 sufficient to permit the enteral tube 280 to be pulled substantially laterally through the slit 298 until the enteral tube 280 is without the catheter 270. In one embodiment, the slit 298 is maintained in a substantially closed position with a removable strip of tape (not shown) placed over the slit 298 on the outside diameter 272 of the catheter 270. The slit 298 preferably has a width of lesser size than the outer diameter of the enteral tube 280, for example, between ¼ and ½ the size of the outer diameter of the enteral tube 280. In another embodiment, where the walls of the catheter 270 are substantially flexible, the slit width can be approximately zero (i.e., the walls on either side of the slit are touching each other) as shown in FIG. 3e.

The catheter 270 can be removably attached to the endotracheal tube 201. For example, referring now to FIG. 5a, in a preferred embodiment, the catheter 270 further comprises an expandable sleeve 500 connected to the outside diameter 272 of the catheter 270 for attaching the catheter to the endotracheal tube 201, the expandable sleeve 500 capable of snugly sliding over the outside diameter of the endotracheal tube. The expandable sleeve 500 can further comprise a stretchable material. The sleeve 500 can be connected along a portion of, or substantially the entire length of, the outside diameter 272 of the catheter 270, and can further comprise one or more expandable sleeves.

Figure 5A:
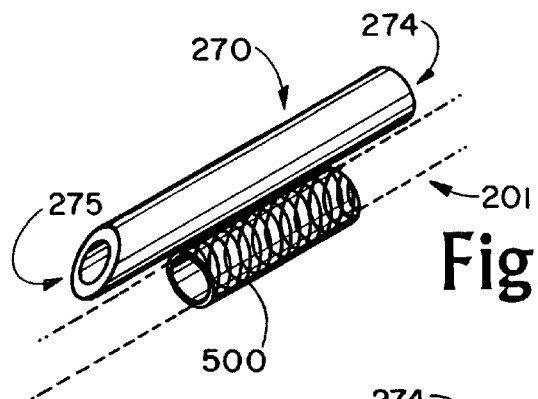
FIG. 5a shows a perspective view of a catheter according to a preferred embodiment of the present intubation invention.
Figure 5B:
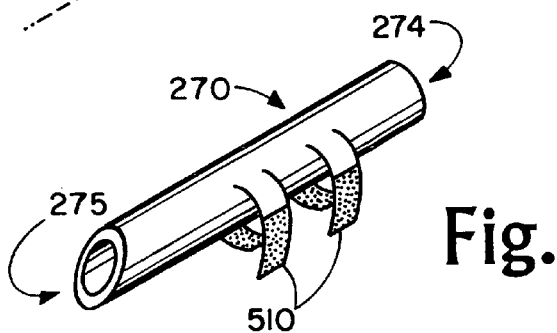
FIG. 5b shows a perspective view of a catheter according to a preferred embodiment of the present intubation invention.

In another preferred embodiment depicted generally in FIG. 5b, the expandable sleeve 500 further comprises one or more closable and reopenable closures 510 connected along the outside diameter 272 of the catheter 270, the closures 510 being capable of wrapping around the outside diameter of the endotracheal tube 201 to secure the catheter 270 to the endotracheal tube 201 or otherwise securing the catheter to the endotracheal tube.

In another preferred embodiment, the catheter 270 is fixably attached to the endotracheal tube using any number of methods known in the art, such as, for example and without limitation, extrusion molding, gluing, heat welding, chemical bonding, ring clips, tape, hook and loop fasteners, such as those sold under the VELCRO® brande, mating channels (e.g., FIG. 3g, 291, 292), mated compression fittings, fasteners, clamps (e.g., FIG. 3c) and encapsulation with shrink wrap. In one embodiment, the catheter is fixably attached to the endotracheal tube so that a seam 290 is created between the outside diameter of the catheter and the outside diameter of the endotracheal tube, the seam having a length that is adjustable.

In yet another preferred embodiment, the catheter 270 can be removably attached to the endotracheal tube 201 using a variety of methods known in the art. For example, the use of tape, hook and loop fasteners, such as those sold under the VELCRO® brand, mating channels, mated compression fittings, fasteners, clamps and the like can be employed to removably attach the catheter. For example, in a preferred embodiment, the catheter 270 and the endotracheal tube 201 contain mated linear tracks (e.g., FIG. 3g, 291, 292) for slidably attaching (or removing) the outer diameter of the catheter to the outer diameter of the endotracheal tube.

Figure 5C:
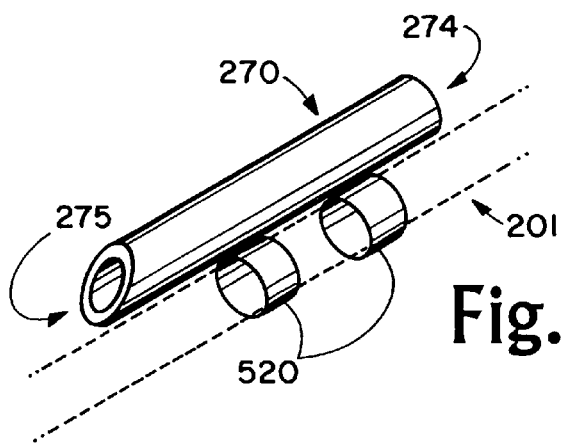
FIG. 5c shows a perspective view of a catheter according to a preferred embodiment of the present intubation invention.

Referring to FIG. 5c, the catheter 270 can also be slidably attached to the endotracheal tube, where the catheter has one or more cylindrical tubes 520 fixably attached to the anterior side of the catheter, these cylindrical tube(s) 520 being substantially co-axially aligned with each other, and the cylindrical tube(s) having a cross-sectional shape substantially similar to the cross-sectional shape of the endotracheal tube 201, an outside diameter, and an inside diameter suitable to facilitate the frictional movement of the endotracheal tube therethrough, a proximal end and a distal end. In this embodiment, the frictional fit of the endotracheal tube 201 could be accomplished in many ways known in the art, including, by way of example, rough mating surfaces; channel locks; clipping mechanisms to name a few.

The intubation device of the present invention can also be constructed in a manner that provides unitary construction. For example, the catheter and endotracheal tube can be fully integrated into unitary device (e.g., FIGS. 3b, 3d, 3e and 3f). Also, the catheter can comprise a conduit located within the wall of the endotracheal tube.

Referring to FIGS. 6a and 6b, the intubation device 200 of the present invention can also preferably further comprise: a first section 600 proximate the proximal end 210 of the endotracheal tube 201 wherein the proximal end of the catheter 274 is maintained external to the endotracheal tube 201, a second section 602 between the proximal and distal ends of the endotracheal tube wherein the catheter is maintained within the endotracheal tube, and a third section 604 toward the distal end of the endotracheal tube wherein the distal end of the catheter 275 is maintained external to the endotracheal tube 201.

In another preferred embodiment, the intubation device 200 of the present invention can be of a substantial unibody wall construction, such as depicted in, for example, FIG. 3b. In this embodiment, the device 200 comprises a first section proximate the proximal end of the endotracheal tube wherein the proximal end of the catheter is maintained within the wall of the endotracheal tube, the proximal end of the catheter being flush with the outside diameter of the endotracheal tube and remaining capable of having the enteral tube pass therethrough; a second section between the proximal and distal ends of the endotracheal tube wherein the catheter is maintained within the endotracheal tube; and a third section toward the distal end of the endotracheal tube wherein the distal end of the catheter is maintained within the wall of the endotracheal tube, the distal end of the catheter being flush with the outside diameter of the endotracheal tube and remaining capable of having the enteral tube pass therethrough.

Figure 7:
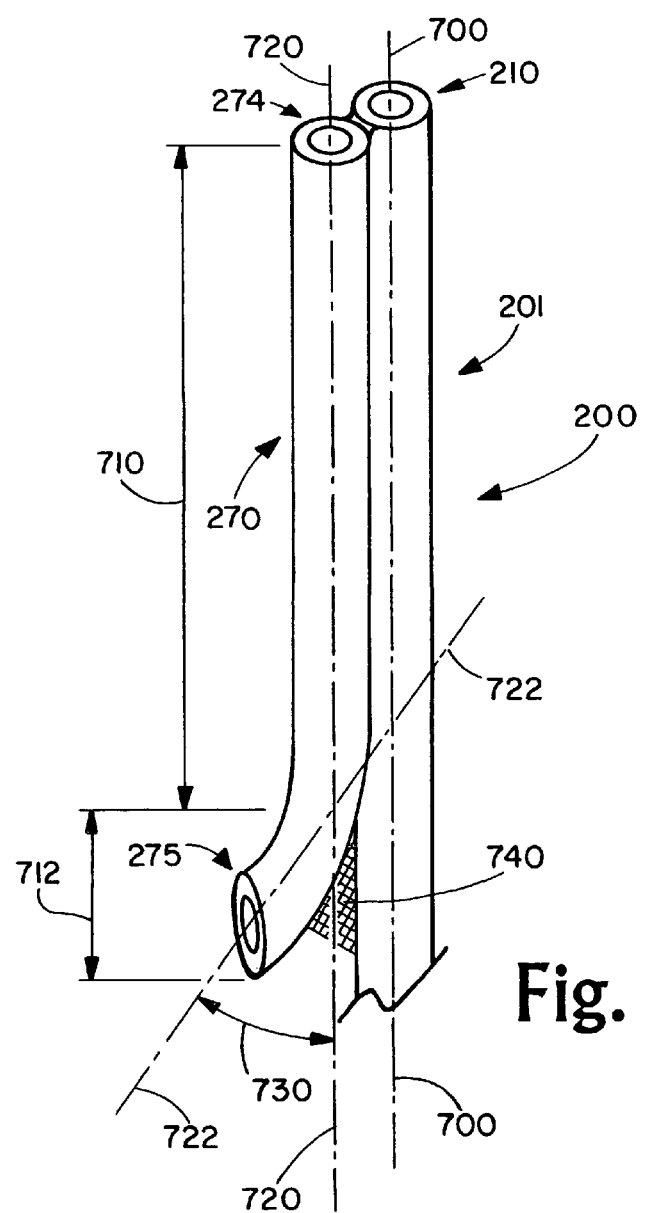
FIG. 7 illustrates a perspective top side (anterior) view of an intubation device according to another preferred embodiment of the present invention.
Figure 8:
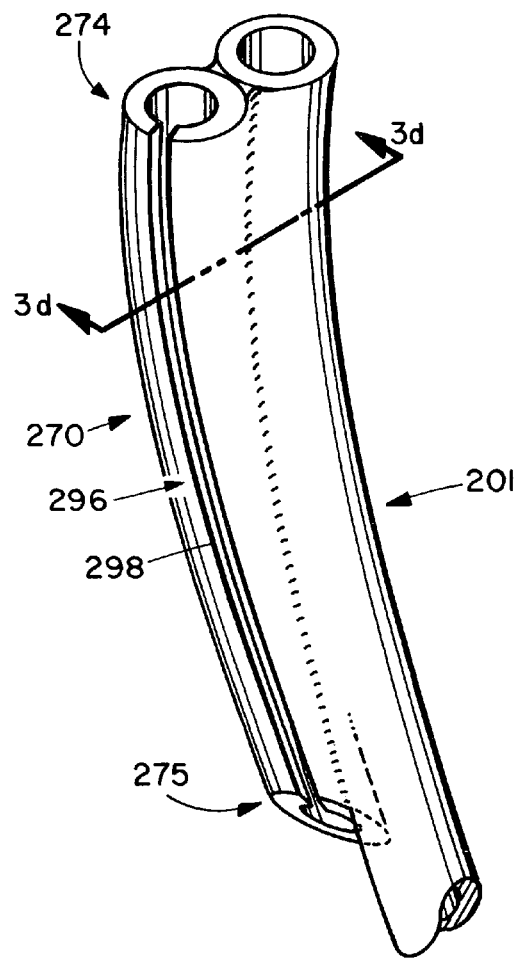
FIG. 8 illustrates a perspective top side (anterior) view of an intubation device according to another preferred embodiment of the present invention.

Referring now to FIG. 7, in another preferred embodiment, the intubation device 200 of the present invention preferably further comprises an endotracheal tube axis 700 located in the distal portion of the endotracheal tube, the endotracheal tube axis being substantially aligned with the axis of the patient's trachea when the distal end of the endotracheal tube is placed within the patient's trachea; a first catheter zone 710 located between the proximal and distal ends of the catheter, wherein the catheter has a first catheter axis 720 that is substantially parallel to the endotracheal tube axis 700; and a second catheter zone 712 located proximate the distal end 275 of the catheter 270 wherein the catheter has a second catheter axis 722 that diverges from the first catheter axis 720. In a preferred embodiment, the second catheter axis 722 diverges from the first catheter axis 720 to direct the path of the enteral tube (280 not shown) posteriorly toward the esophagus of the patient. In another preferred embodiment, the second catheter axis 722 diverges from the first catheter axis 720 to form an angle 730 between both axes (720, 722) to optimally align the distal end 275 of the catheter 270 for directing the path of the enteral tube posteriorly toward the esophagus of the patient. The angle 730 can preferably be between about 15 degrees and 60 degrees. The angle 730 can be fixed or adjustable. For example, the angle could be preconfigured in the shape of the distal end 275 of the catheter 270. Also, the angle 730 could be set by using a wedge-like (or other suitably shaped) device 740 to create or adjust the angle 730.

In another preferred embodiment of the present invention, the intubation device further comprises a malleable stylet for use in shaping the device. In one example, the endotracheal tube (and/or the catheter) further comprises a malleable stylet for use in shaping the endotracheal tube (and/or the catheter), the stylet having a distal end and a proximal end. The stylet can employ fiber optics capable of transmitting an optical image signal from the distal end of the stylet to a display device connected to the proximal end of the stylet. In a preferred embodiment, the stylet is integrated into the endotracheal tube (and/or catheter), such as by being built into the wall of the endotracheal tube (and/or catheter) (e.g., FIG. 3h, 299). Alternatively, the stylet is insertable into and removable from the inside diameter of the endotracheal tube and/or catheter.

In another preferred embodiment, the endotracheal tube (and/or catheter) further comprises one or more strands of a flexible, memory retaining material capable of being manipulated to facilitate the defining of the arcuate path or otherwise to facilitate the shaping of the endotracheal tube and/or catheter.

Additionally, the endotracheal tube of the present invention may contain a manual curvature adjustment ring 160 to likewise facilitate the defining of the arcuate path or otherwise to facilitate the shaping of the endotracheal tube 201.

In another preferred embodiment of the present invention, there is disclosed a combination medical device comprising: an endotracheal tube with a substantially circular cross-section, an outside diameter, an inside diameter, a proximal end and a distal end; and a catheter to guide the path of an enteral tube. The endotracheal tube defines an arcuate path in a first plane between its proximal end and its distal end to facilitate introduction of the tube into the trachea of a patient. The endotracheal tube employs an inflatable cuff for achieving a seal with an inner wall of the trachea of the patient positioned generally toward the distal end of the endotracheal tube, the inflatable cuff being in fluid communication with an inflation port positioned generally toward the proximal end of the endotracheal tube. The catheter has a substantially circular cross-section, an outside diameter, and an inner diameter suitable to facilitate the smooth movement of the enteral tube therethrough, and a length defined by a proximal end and a distal end. The catheter is attached to the endotracheal tube along substantially the entire length of said catheter, the proximal end of the catheter being positioned generally outside the first plane, the length of the catheter extending along only a portion of the length of the endotracheal tube. In this embodiment, the catheter defines a substantially partial-spiral path around the outside diameter of the endotracheal tube to position the distal end of the catheter in the first plane, the distal end of the catheter having a diagonal cut at the end to facilitate the introduction of the enteral tube into the esophagus of the patient. The catheter of this embodiment can also comprise a fenestration along substantially the entire length of the catheter wall to facilitate the removal from the catheter of an enteral tube having previously been placed therethrough without the need to remove the enteral tube from the patient.

The endotracheal tube of the present invention can also employ markings to assist medical personnel in ascertaining placement and positioning of the device.

In yet another preferred embodiment of the present invention, there is disclosed an endotracheal intubation device comprising:
a substantially circular cross-section, an outside diameter, an inside diameter, a proximal end, a distal end, a wall thickness defined as the space between the outside diameter and the inside diameter;
  the endotracheal intubation device capable of defining an arcuate path in a first geometric plane between its proximal end and its distal end to facilitate introduction of the tube into the trachea of a patient,
  the arcuate path, when so defined, having a concave side and a convex side substantially opposite said concave side,
  the endotracheal tube, when so defined in the arcuate path, having a concave side and a convex side substantially opposite said concave side,
a malleable stylet for use in shaping said endotracheal intubation device;
  the stylet having a distal end and a proximal end and being integrated into said wall thickness; and
an inflatable cuff for achieving a seal with an inner wall of the trachea of the patient positioned generally toward the distal end of said endotracheal intubation device,
  the inflatable cuff being in fluid communication with an inflation port positioned generally toward the proximal end of said endotracheal tube.
In this embodiment, the stylet can further comprise one or more strands of a flexible, memory retaining material capable of being manipulated to facilitate the defining of the arcuate path. Additionally, if desired, this intubation device can employ integrated fiber optics capable of transmitting an optical image signal from the distal end to a display device.

In yet another preferred embodiment of the present invention, there is described a method of intubating a patient comprising the steps of: (a) providing an intubation device in accordance with embodiments of the present invention; (b) inserting into the oral cavity of a patient the intubation device oriented such that the distal end of the endotracheal tube enters first; (c) orienting the distal end of the endotracheal tube with the patient's trachea; (d) inserting the distal end of the endotracheal tube into the patient's trachea; (e) inflating the inflatable cuff by administering a source of air into the inflation port; and ventilating the patient through the endotracheal tube. A preferred embodiment includes the additional step of directing a desired enteral tube into the proximal end of the catheter, through the catheter, out the distal end of the catheter and into the desired location of the patient. Another preferred embodiment of this method includes the additional step of removing the intubation device without removing said enteral tube from said desired location within the patient.

When the catheter of the intubation device of the present invention includes the fenestration feature, a preferred embodiment of the present inventive method can also include the additional steps of: deflating the inflatable cuff of the endotracheal tube; maintaining the enteral tube in its desired location while withdrawing the intubation device from the patient's oral cavity; and maintaining the enteral tube in its desired location while directing the enteral tube through the fenestration.

When the catheter of the intubation device of the present invention includes an integrated, malleable stylet for use in shaping the intubation device, a preferred embodiment of the present inventive method can also include the additional step of: shaping the intubation device prior to inserting the device into the oral cavity of a patient so that the shape of the intubation device facilitates the insertion of the device into the oral cavity of the patient.

When the catheter of the intubation device of the present invention includes an integrated array of fiber optics capable of transmitting an optical image signal from the distal end of the device to a display device external to the patient, a preferred embodiment of the present inventive method can also include the additional step of: viewing the display of the fiber optics image signal on the display device while inserting the intubation device into the patient to facilitate placement of the intubation device.

The conduits may individually include reinforcement that inhibits collapse of the conduit. However, the coupling of the primary tracheal conduit with the auxiliary gastric conduit serves also to reinforce the coupled conduits to prevent collapse from, e.g., patient biting.

Further to disclosure set out in connection with FIGS. 2-8 and the embodiments disclosed in connection with FIG. 3c, and FIGS. 5a-c, all of which are incorporated herein by reference, referring now to FIGS. 9A-15 there is shown a preferred embodiment of an attachable catheter device 900 that can be removably attached to an endotracheal tube 100 such as the endotracheal tube 100 shown in FIG. 1. In this embodiment, the lumen 101 of the endotracheal tube (not shown to scale) is removably attachable to the catheter 900 by the use of a clip assembly comprising one or more clips, such as a distal end c-shaped clip 906, and a proximal end c-shaped clip 908. The clip assembly can also employ a locking device, such as an adjustable locking ratchet connector clamp 916 to secure the positioning of the lumen 101 relative to the catheter 900.

Referring to FIGS. 9A-15, the attachable catheter device 900 comprises a catheter conduit 912 having a proximal end 902, a distal end 904 opposite the proximal end, and a conduit wall member 913a defining an internal catheter inside space or conduit space 905 between such proximal end 902 and distal end 904. The catheter conduit 912 (like with catheter 270 described above in reference to FIGS. 2-8), preferably has a substantially circular cross-section (but oval and other cross-sectional configurations would be possible), where the conduit wall member 913a comprises an outside wall defining an outside diameter, and an inside wall 913b defining an inside diameter suitable to facilitate the smooth movement of the enteral tube 280 therethrough. The catheter conduit 912 has a wall thickness defined as the space between the outside wall 913c diameter and the inside wall 913b diameter, and a length defined by the distance between the catheter proximal end 902 and the catheter distal end 904. The catheter conduit 912 has a catheter conduit proximal end axis 934 located in the proximal portion of the catheter conduit 912, and a catheter conduit distal end axis 932 located in the distal portion of the catheter conduit 912 wherein the catheter conduit 912 can be shaped or configured so that the catheter conduit distal end axis 932 can diverge from the catheter conduit proximal end axis 934.

In this embodiment, the catheter 900 has attached at its distal end a distal end flexible c-shaped clip 906 capable of receiving, preferably in snug relationship, a section of the outer diameter of lumen 101. The distal end flexible c-shaped clip 906 is mounted on the catheter conduit 912 by a suitable distal end c-shaped clip mount 906d. The distal end c-shaped clip has a distal end flexible c-shaped clip upper edge 906a, distal end flexible c-shaped clip upper edge first end 906c, distal end flexible c-shaped clip upper edge second end 906b, distal end flexible c-shaped clip lower edge 906e, distal end flexible c-shaped clip lower edge first end 906g, distal end flexible c-shaped clip lower edge second end 906f, and distal end flexible c-shaped clip interior gripping surface 906h. In this embodiment, the c-shape of the distal end c-shaped clip forms a substantially cylindrical space for the gripping surface 906h to receive and grip a substantially cylindrical portion of lumen 101 wherein such gripping space has a distal clip axis 940 substantially parallel to the catheter distal end axis 932. The distal end c-shaped clip also has a clip distal end opening 906j and a clip proximal end opening 906k. The distal end c-shaped clip can be made of a plastic/polymeric (or other suitable) material providing sufficient flexibility to permit the insertion of the outer diameter surface of the lumen 101 into the distal end flexible c-shaped clip (to permit the opening/gap/fenestration 906i between distal end c-shaped clip upper edge 906a and distal end c-shaped clip lower edge to widen). The plastic material of the distal end flexible c-shaped clip also preferably has sufficient memory to permit the interior gripping surface 906h of the distal end c-shaped clip 906 to snugly grip the outside of lumen 101. It is understood that where a lumen design may have a differently-shaped exterior surface, such as square-like, oval, or hexagonal-like, etc., the shape of the distal end c-shaped clip 906 could be shaped accordingly to received the lumen in snug relationship. It is also understood that the distal end c-shaped clip can take on any number of configurations and shapes that are capable of receiving and holding or gripping a portion of the outside surface of a lumen 101. Also, the interior gripping surface 906h could be configured with a variety of surface features, such as ribs, bumps, roughening, or other features that serve to assist in the gripping of the lumen 101.

In this embodiment, the catheter 900 has attached at its proximal end a proximal end flexible c-shaped clip 908 also capable of receiving another section of the outer diameter of lumen 101. The proximal end flexible c-shaped clip 908 is mounted on the catheter conduit 912 by a suitable proximal end c-shaped clip mount 908d. The proximal end c-shaped clip 908 has a proximal end flexible c-shaped clip upper edge 908a, proximal end flexible c-shaped clip upper edge first end 908c, proximal end flexible c-shaped clip upper edge second end 908b, proximal end flexible c-shaped clip lower edge 908e, proximal end flexible c-shaped clip lower edge first end 908g, proximal end flexible c-shaped clip lower edge second end 908f, and proximal end flexible c-shaped clip interior wall gripping surface 908h. In this embodiment, the c-shape forms a substantially cylindrical space for the gripping surface 908h to receive and grip a substantially cylindrical portion of lumen 101 wherein such gripping space has a proximal clip axis 938 substantially parallel to the catheter proximal end axis 934. The proximal end c-shaped clip also has a clip distal end opening 908j and a clip proximal end opening 908k. The proximal end c-shaped clip 908 can be made of a plastic/polymeric (or other suitable) material providing sufficient flexibility to permit the insertion of the outer diameter surface of the lumen 101 into the proximal end flexible c-shaped clip (to permit the opening/gap/fenestration 908i between distal end c-shaped clip upper edge 906a and distal end c-shaped clip lower edge to widen). The plastic material of the distal end flexible c-shaped clip also preferably has sufficient memory to permit the interior gripping surface 906h of the distal end c-shaped clip 906 to snugly grip the outside of lumen 101.

The catheter conduit proximal end c-shaped clip 908 can also serve as a bite block device to inhibit the potential collapse of the catheter conduit 912 or the endotracheal lumen 101 contained therein from, e.g., patient biting. The catheter conduit proximal end c-shaped clip 908 may include reinforcement that inhibits collapse of the catheter conduit 912 and the endotracheal tube lumen 101 contained therein and may also serve to reinforce these areas.

Once the catheter device is inserted into and positioned within the patient's oral cavity, it is desirable to secure the catheter device in place to prevent the patient from, e.g., ejecting the device. As such, the attachable catheter conduit 900 can also comprise one or more loops 914 for securing the ends of an adjustable strap (not shown). For example, one end of the strap can be attached to a/the loop 914, the strap can then be directed around the back of the patient's neck, and the opposite end of the strap can then be secured to a/the/another loop 914. The tightness of the strap (not shown) can then be adjusted to secure the positioning of the catheter device within the patient.

The attachable catheter conduit 900 can also comprise at its proximal end 902 a locking mechanism to lock the catheter conduit 912 into a locked position relative to the lumen 101. The locking mechanism can comprise, for example, an adjustable locking ratchet pawl type connector/clamp 916 (see, e.g., FIGS. 12-13) having a generally cylindrical shape having a ratchet axis 915. The ratchet clamp 916 has a ratchet clamp proximal end 917, and a ratchet clamp distal end 919. In the present embodiment, the ratchet clamp 916 also has an attachment tab 921 (having end 921a) on its distal end 919 for attaching the distal end 919 of the ratchet clamp 916 axially (along axis 938) to the proximal end 902 of the proximal end c-shaped clip 908 such that axes 938 and 915 are aligned. The ratchet clamp employs ratchet pawl 918 located at the end of ratchet pawl arm 918a and being separated from the outer surface of the ratchet clamp by pawl gap 918b. The ratchet clamp 916 employs a series of saw-toothed ratchet gears 920 for engaging the ratchet pawl 918. When the ratchet pawl clamp is in its loosened or unclamped position, the gears 920 are not engaged with the pawl 918. In the unclamped position, the clamp body has a pawl fenestration 920c defined as the gap between two parallel ratchet pawl ramps 920a, 920b. The ratchet pawl cylinder forms an internal space or conduit 923 defined by the interior gripping surfaces 926, 928 of the ratchet clamp 916 and also has a hinge area 930 located opposition the ramps 920a, 920b. The ratchet clamp cylinder is of sufficient diameter so that it is capable of receiving the outer diameter of the lumen 101. The ratchet pawl clamp 916 is constructed of a material sufficiently flexible to permit expansion of the internal space 923 to permit placement therein of a portion of the outer lumen 101 of an endotracheal tube 100. The ratchet pawl clamp 916 employs two finger grips, one finger grip 922 located as part of the pawl arm 918a and the other finger grip 924 located proximate the pawl gears 920 so that when the two finger grips 922, 924 are urged toward each other, the pawl ramps 920a, 920b engage each other and move the pawl gears 920 into locking engagement with the pawl 918 until the desired tightness is achieved. When the pawl finger grips 922, 924 are urged apart from each other, then pawl 918 becomes disengaged from the pawl teeth 920, and the endotracheal tube lumen is released from the interior gripping surfaces 926, 928 of the ratchet clamp.

The ratchet attachment tab 921 can be attached to a mated notch (not shown) in the surface 908h of the proximal end of proximal c-shaped clip 908 by gluing or other conventional means, including unitary construction techniques such as injection molding, other integrated manufacturing techniques and the like. When the ratchet clamp 916 is attached to the proximal c-shaped clip 908, it is preferred to permit a ratchet connector distal end gap 919a to exist so that the movement of the ratchet can move independently from the c-shaped clamp.

The basic mechanism of operation of adjustable ratchet clamps is known in the art. For example, Gadberry, et al., U.S. Pat. No. 6,461,363 discloses the use of a ratchet gear and ratchet pawl system formed on engaging surfaces of finger grips on a surgical clamping tool. Adjustable ratchet clamps, such as the adjustable nylon ratchet clamps available and depicted on the worldwide web from ElectricalBasics.com show the basic structure of an adjustable ratchet clamp. Although the ElectricalBasics.com clamps are depicted as having a planar adhesive mounting system (for example to mount the clamp on a flat surface for use in securing one or more cables), such basic structure could be modified to permit mounting of a clamp of this type onto the catheter device 900.

Figure 12:
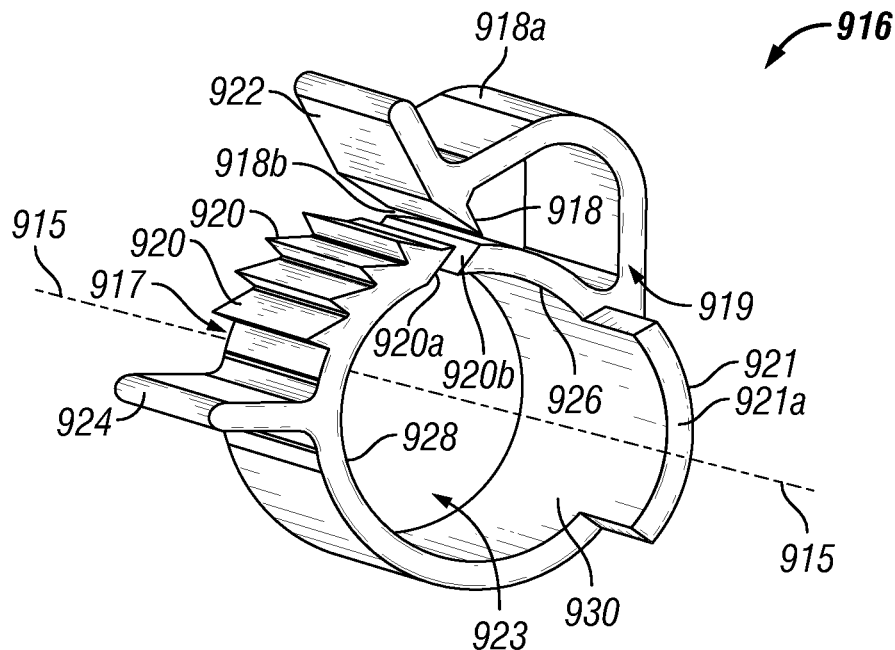
FIG. 12 illustrates a perspective, distal end view of the adjustable locking ratchet clamp employed in the catheter of FIG. 9A.
Figure 13:
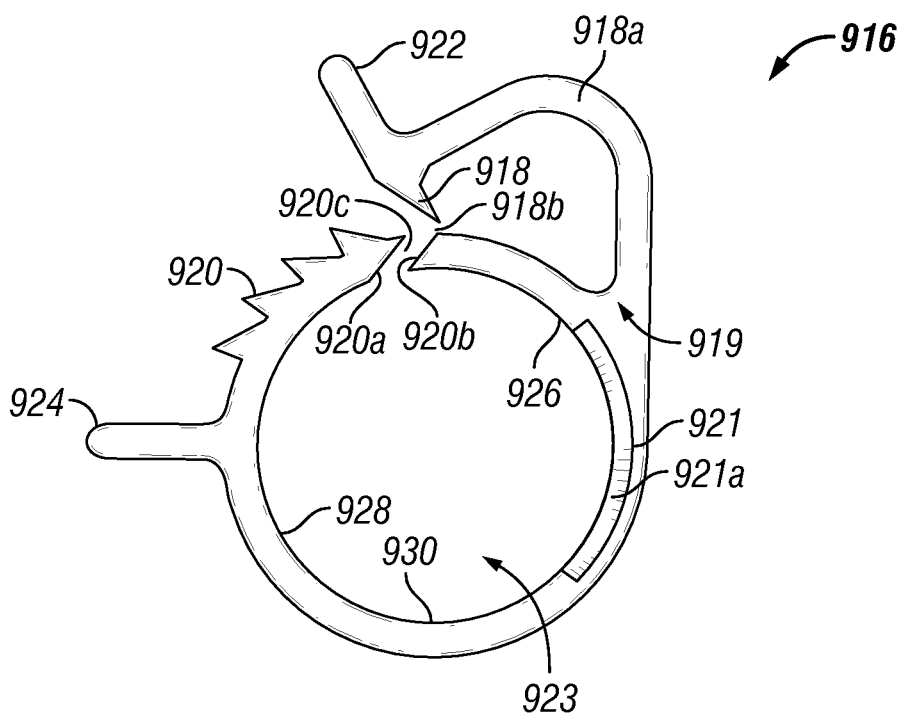
FIG. 13 illustrates a distal end view of the adjustable locking ratchet clamp of FIG. 12.
Figure 14:
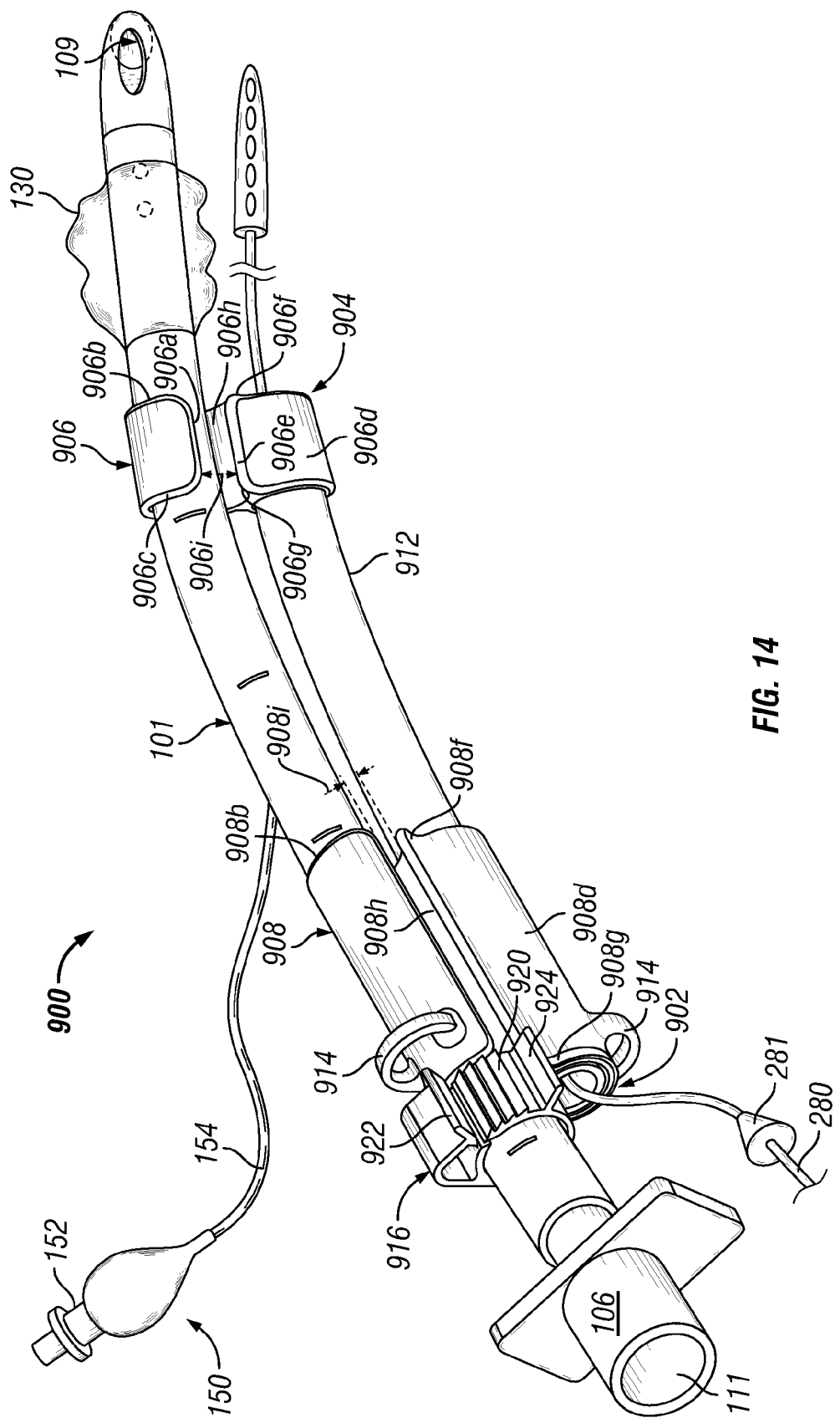
FIG. 14 illustrates a perspective top side (anterior) view of the catheter shown in FIG. 9A, housing an endotracheal tube (not shown to scale).
Figure 15:
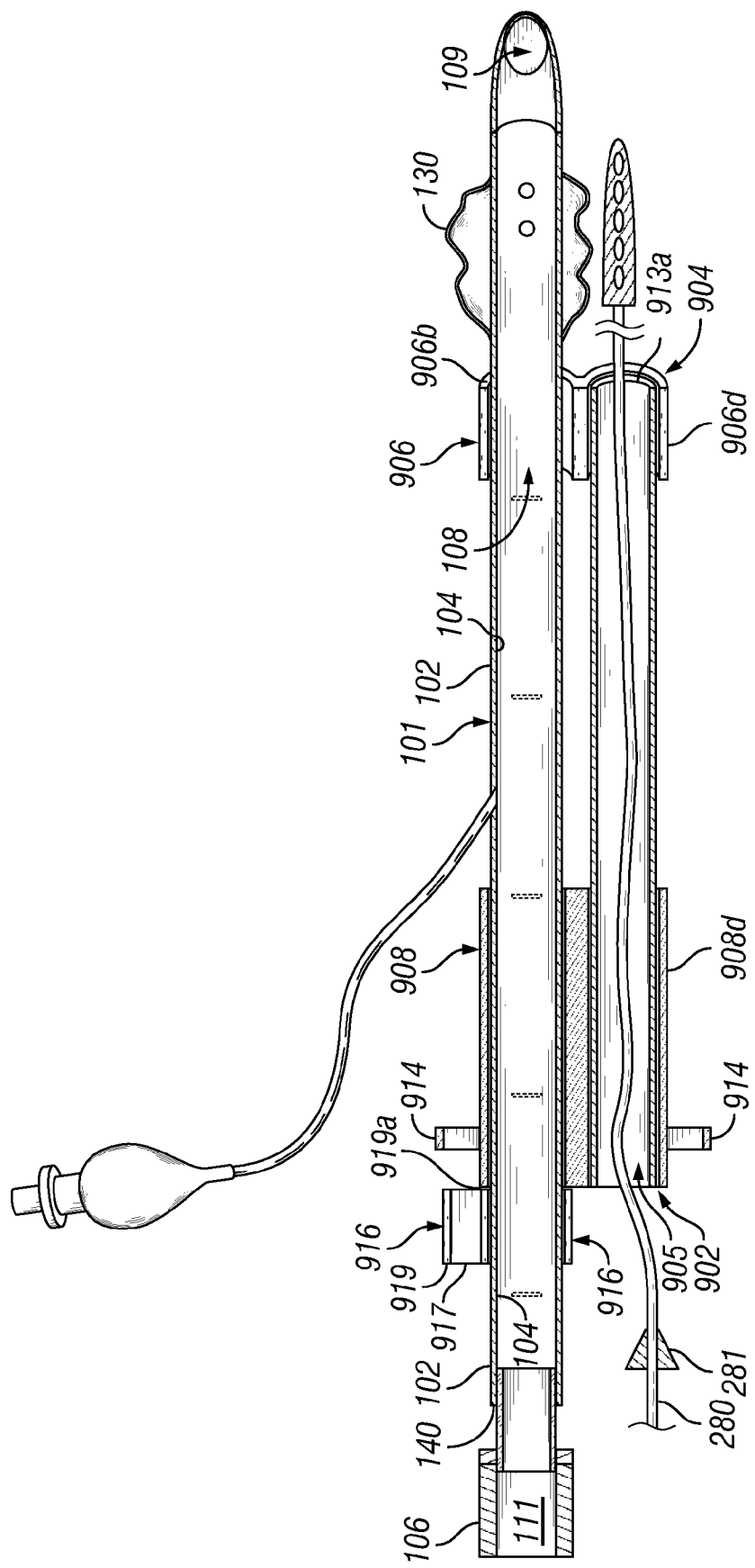
FIG. 15 illustrates a cross-sectional top side view of the catheter shown in FIG. 14, housing an endotracheal tube (not shown to scale) where the locking ratchet connector used to secure the endotracheal tube in place is not in the engaged position.
Figure 16A:
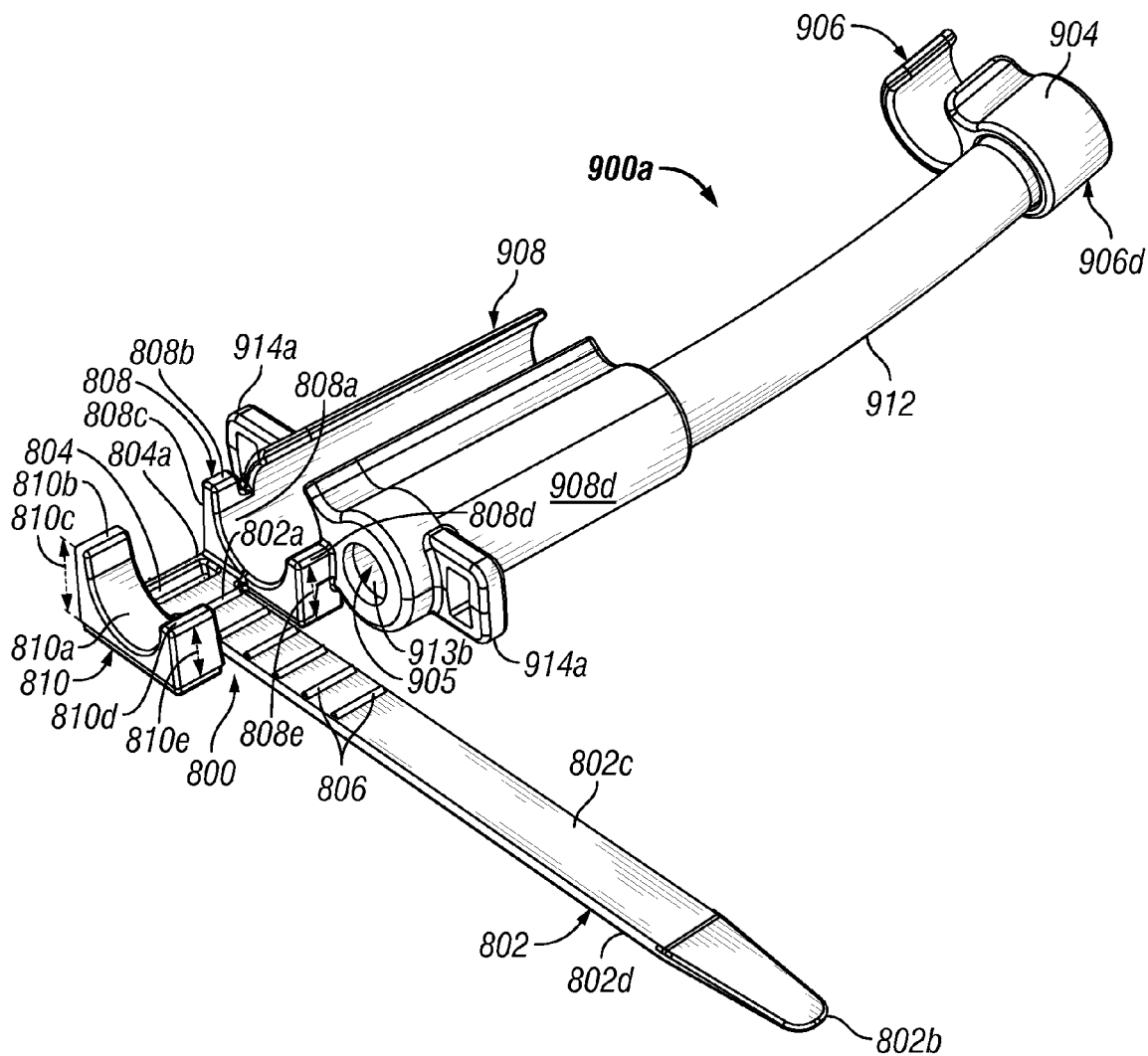
FIG. 16A illustrates a perspective top side (anterior) view of a catheter attachable to an endotracheal tube (not shown) according to another preferred embodiment of the present invention.
Figure 16B:
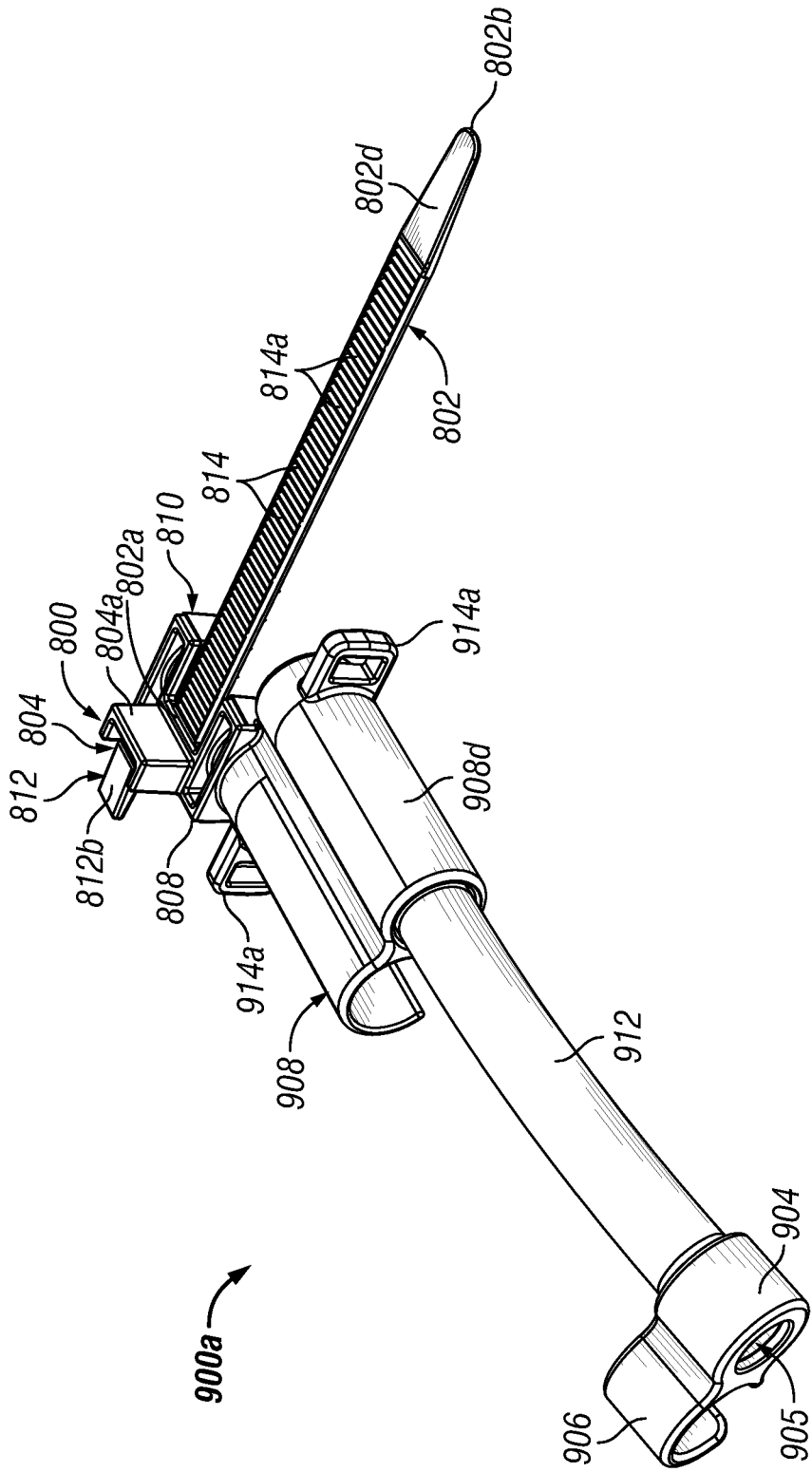
FIG. 16B illustrates a perspective bottom side (posterior) view of the catheter shown in FIG. 16A.

Once the endotracheal tube 101 is placed into the catheter device 900, its position can be secured by tightening the adjustable locking ratchet clamp 916. Pinching the opposed finger tabs (pawl tab/finger grip 922 and gear finger tab 924) of the ratchet clamp toward each other permits the ratchet clamp to securely tighten around the outer diameter of the endotracheal tube 101 as the teeth of the semicircular gear section 920 engage the surface of the ratchet pawl 918. After use, the ratchet clamp can be returned to a released position (as shown in FIGS. 12-13) by releasing the ratchet pawl 918 to disengage the ratchet gear 920 to permit removal of the endotracheal tube 100 from the catheter device 900 (the adjustable ratchet clamp 916 shown in FIG. 14 is depicted in a disengaged position).

Much like as described in connection with FIGS. 5a-c, the proximal and distal c-shaped clips/fasteners 906, 908 and the locking ratchet connector/clamp 916 of the present embodiment serve as closeable and reopenable closures to permit the removable attachment of the catheter 912 to the lumen 101.

As described above with respect to the embodiments of the invention pertaining to FIGS. 2-8, the length of the catheter conduit 912 preferably extends along only a portion of the length of the endotracheal lumen 101 (the endotracheal tube 101 is not drawn to scale). The distal end 904 of the catheter conduit 912 is positioned to facilitate the introduction of the enteral tube 280 into the esophagus of the patient. The catheter conduit 912 can preferably be constructed of a flexible, generally transparent material. The flexible material used for the catheter conduit could be any plastic/polymeric material having suitable ductility and fitness for use in the oral cavity of a patient, such as the materials used in conventional endotracheal tubes and other materials known to those of ordinary skill in the art. The catheter conduit 912 is designed to permit entry of any variety of enteral tubes 280, such as, an orogastric tube. The distal end 904 of the catheter conduit 912 is preferably positioned to direct the path of the enteral tube 280 posteriorly toward the esophagus 450 of the patient 400. The distal end 904 of the catheter conduit 912 can also be preferably positioned to direct the path of the enteral tube 280 into the gastrointestinal tract of the patient (not shown). The positioning of the catheter conduit 912 relative to the endotracheal lumen 101 is in a substantially parallel or side-by-side configuration. For example, much like that depicted in FIGS. 2a-2d, the proximal end 902 of the catheter conduit 912 is positioned generally outside of the first or saggital plane in the second or coronal plane and the distal end 904 of the catheter conduit 912 is positioned generally within the first or saggital plane.

Figure 9A:
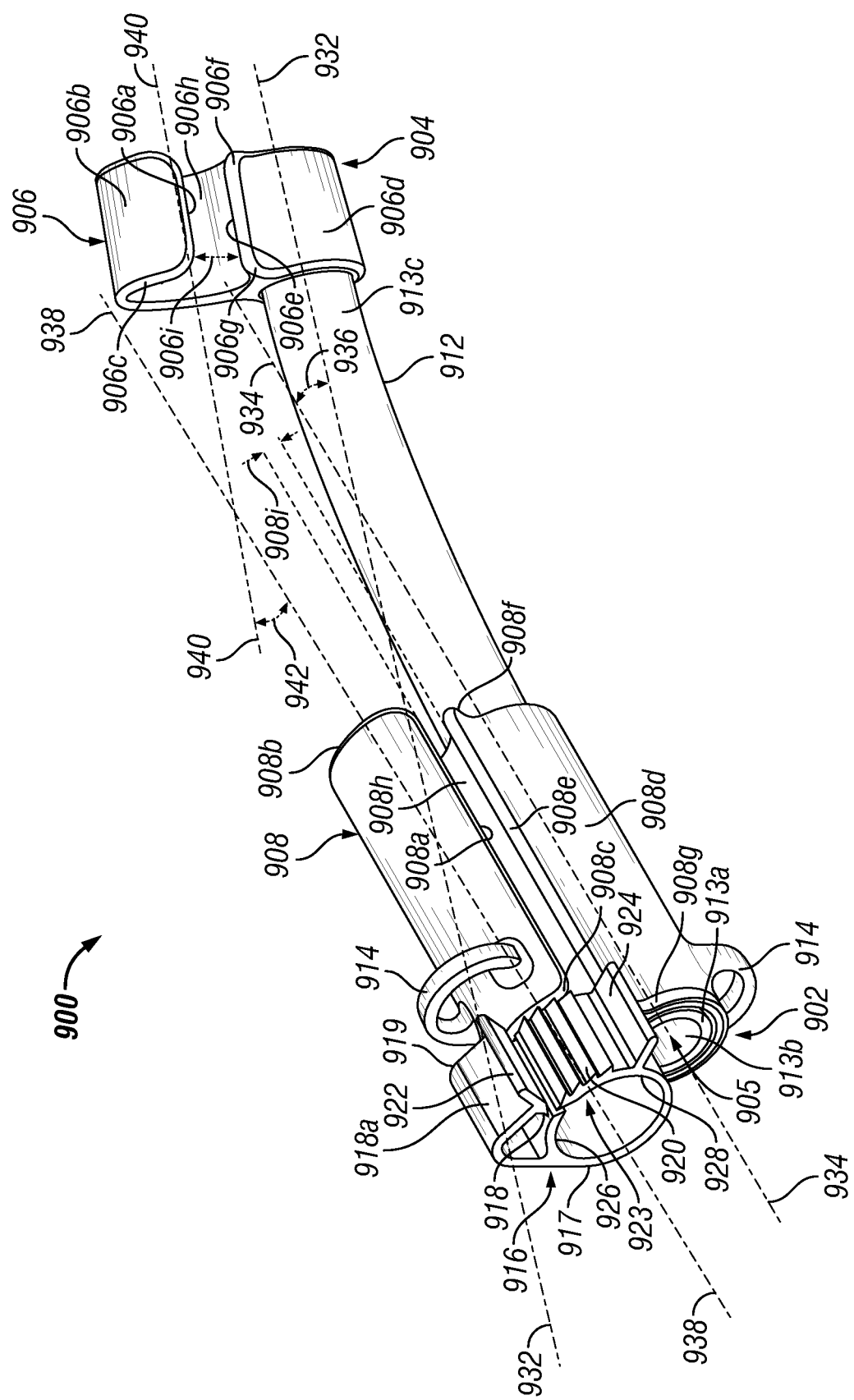
FIG. 9A illustrates a perspective top side (anterior) view of a catheter attachable to an endotracheal tube (not shown) according to another preferred embodiment of the present invention.

Referring to the attachable catheter device 900 shown in FIG. 9A, also in reference to FIG. 7, the catheter conduit 912 has a catheter conduit proximal end axis 934 located in the proximal portion of the catheter conduit 912, and a catheter conduit distal end axis 932 located in the distal portion of the catheter conduit 912 wherein the catheter conduit distal end axis 932 diverges from the catheter conduit proximal end axis 934. This deviation of the axis 932 from axis 934, or curvature of the catheter conduit 912, assists in directing the path of the enteral tube (280 not shown) posteriorly toward the esophagus of the patient. In one embodiment, the catheter conduit distal axis 932 diverges from the catheter conduit proximal axis 934 to form a conduit angle 936 between both axes (932, 934) to optimally align the distal end 904 of the catheter conduit 912 for directing the path of the enteral tube posteriorly toward the esophagus of the patient. The conduit angle 936 can be between about 0 degrees and 30 degrees. In one embodiment, the conduit angle 936 is about 10 degrees.

The conduit angle 936 can be fixed or adjustable to create an arcuate path through the catheter conduit internal space 905. For example, the catheter conduit 912 could employ a malleable stylet (not shown) for use in shaping the catheter conduit (and its arcuate path), the stylet having a distal end and a proximal end. The stylet can employ fiber optics capable of transmitting an optical image signal from the distal end of the stylet to a display device connected to the proximal end of the stylet. The stylet could be integrated into the catheter conduit 912, such as by being built into the wall of the catheter conduit 912. Alternatively, the stylet is insertable into and removable from the inside diameter 905 of the catheter conduit 912. Additionally, the attachable catheter device 900 could be attached to an endotracheal lumen 101, and such curvature or conduit angle 936 could be achieved by then bending or otherwise shaping the endotracheal tube lumen 101 with use of, e.g., a stylet or manual curvature adjustment ring 160.

Although the distal end clip axis 940 is generally shown as being parallel to that of the catheter conduit distal end axis 932, and the proximal end clip axis 938 is generally shown as being parallel to that of the catheter conduit proximal end axis 934, other orientations could be achieved by adjusting the distal end clip axis 940 and/or the proximal end clip axis 938. The distal end clip 906 is preferably attached to the catheter conduit 912 proximate the distal end 904 of the catheter conduit 912 for receiving and removably attaching a portion of the endotracheal tube 101 located toward the distal end 120 of the endotracheal tube 101, the distal end clip 906 having a first distal clip end 906c oriented toward the catheter conduit proximal end 902 and a second distal clip end 906b oriented toward the catheter conduit distal end 904, The distal end clip 906 has a distal end clip axis 940 which extends axially through the distal end clip 906 from the distal end clip first end 906c toward the distal end clip second end 906b. The proximal end clip 908 is preferably attached to the catheter conduit 912 proximate the proximal end 902 of the catheter conduit 912 for receiving and removably attaching a portion of the endotracheal tube 101 near the proximal end 110 of the endotracheal tube 101, the proximal end clip 908 having a first proximal clip end 908c oriented toward the catheter conduit proximal end 902 and a second proximal clip end 908b oriented toward the catheter conduit distal end 904. The proximal end clip 908 has a proximal end clip axis 938 which extends axially through the proximal end clip 908 from the proximal end clip first end 908c toward the proximal end clip second end 908b. One such adjustment includes bending the catheter conduit in a desired direction. Another adjustment includes twisting the catheter conduit about its axes 394, 392.

Yet another adjustment includes rotating the position of the distal end clip 906 relative to the catheter conduit distal end axis 932.

Referring again to the attachable catheter device 900 shown in FIG. 9A, the proximal end clip axis 938 is depicted as diverging from the distal end clip axis 940. This deviation of the axis 938 from axis 940, or curvature of the catheter conduit 912, assists in directing the path of the enteral tube (280 not shown) posteriorly toward the esophagus of the patient. In one embodiment, the distal end clip axis 940 diverges from the proximal end clip axis 938 to form a clip angle 942 between both axes (938, 940) to optimally align the distal end 904 of the catheter conduit 912 for directing the path of the enteral tube posteriorly toward the esophagus of the patient. The clip angle 942 can be between about 0 degrees and 30 degrees. In one embodiment, the clip angle 942 is about 10 degrees.

Figure 9B:
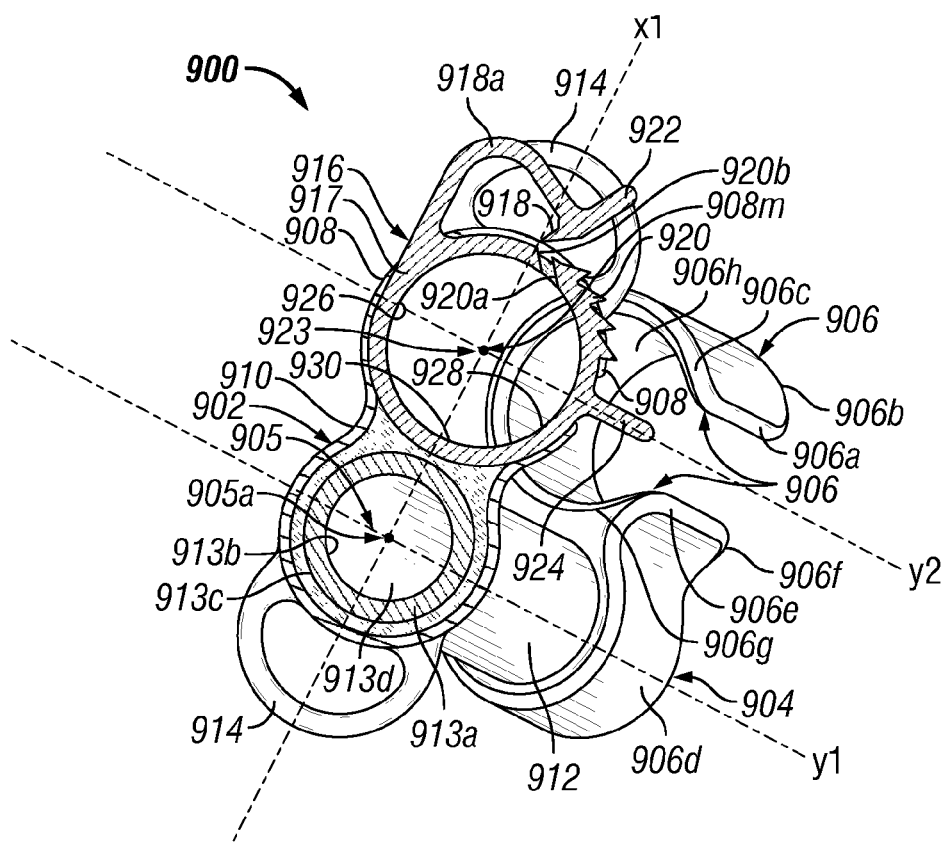
FIG. 9B illustrates a proximal end view of the catheter shown in FIG. 9A.
Figure 10A:
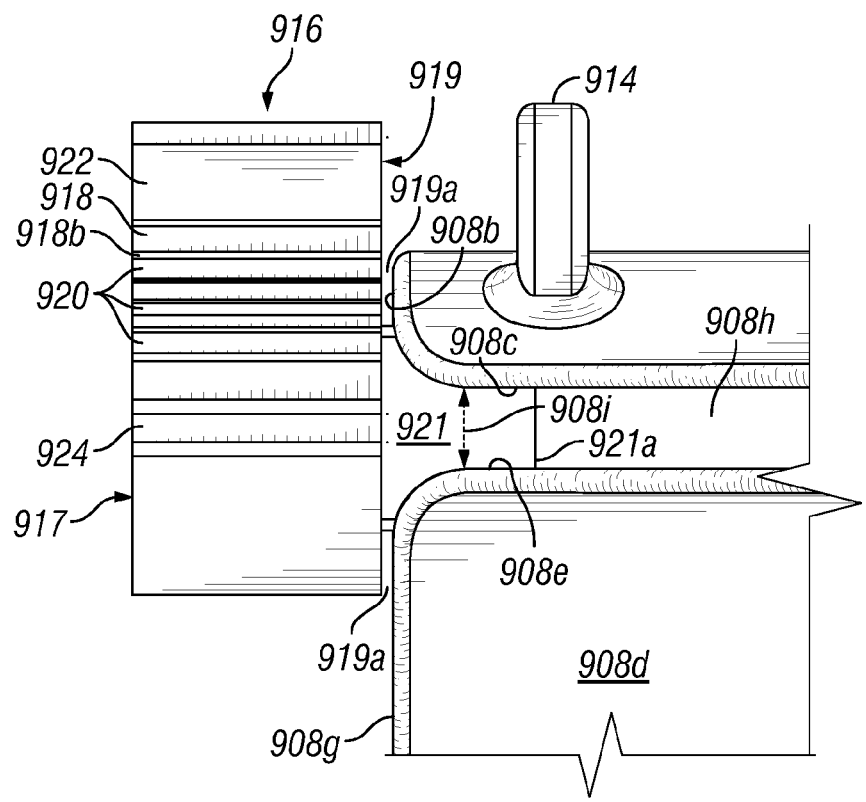
FIG. 10A illustrates a right side close-up view of the proximal end of the catheter shown in FIG. 10B.
Figure 10B:
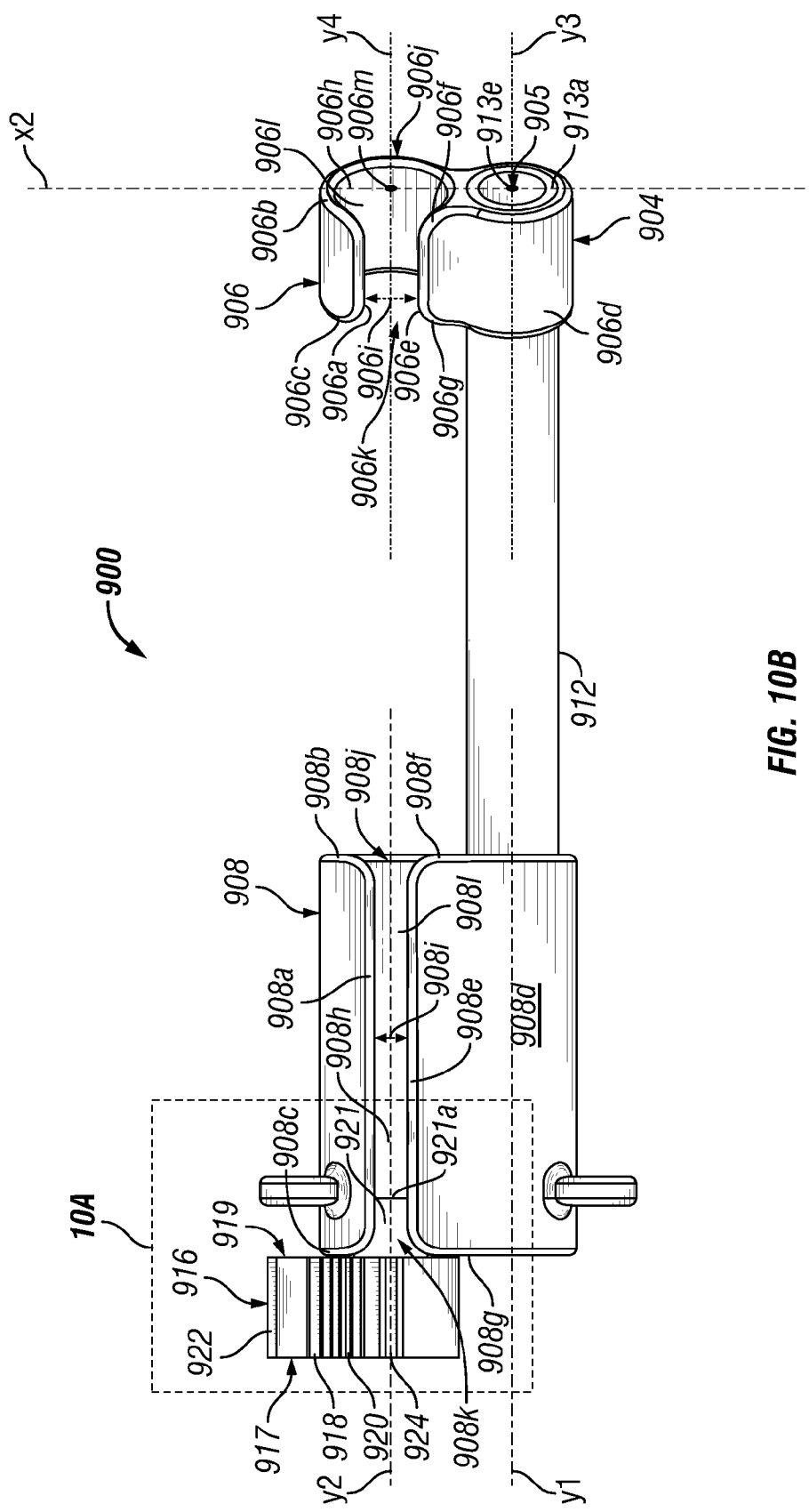
FIG. 10B illustrates a right side view of the catheter shown in FIG. 9A.
Figure 11:
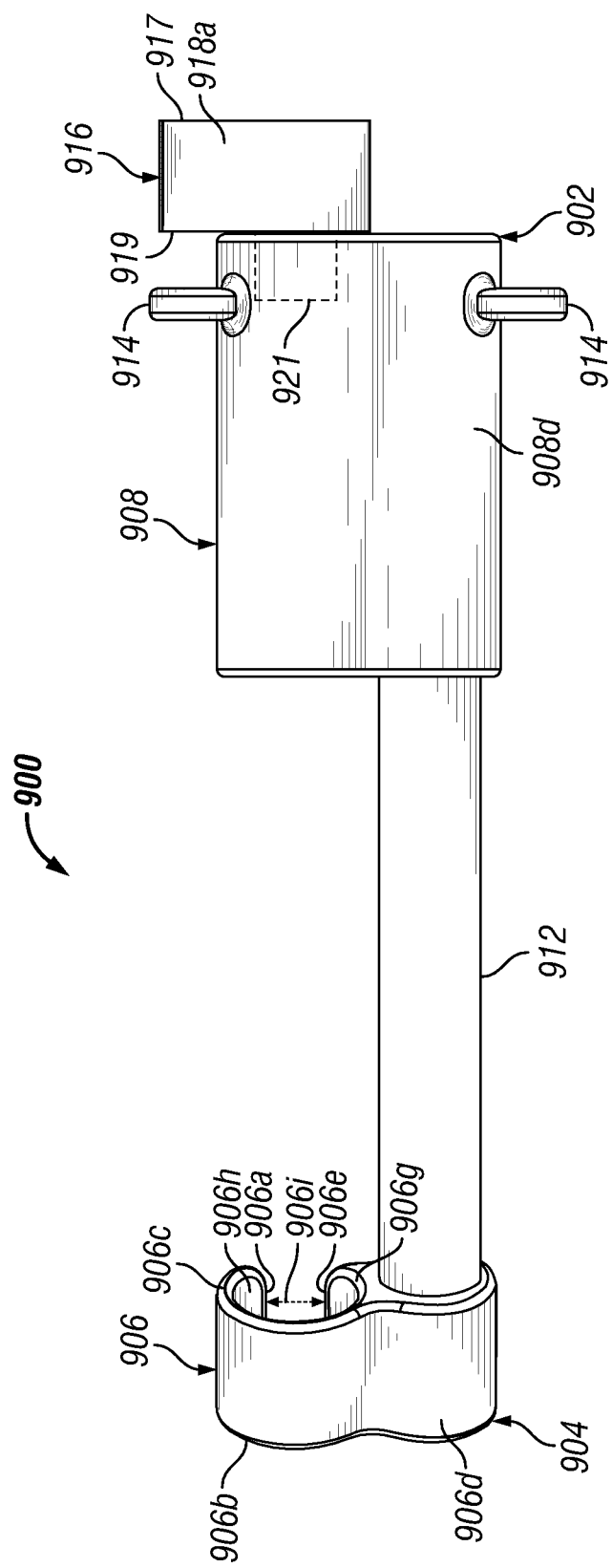
FIG. 11 illustrates a left side view of the catheter shown in FIG. 9A.

Referring to FIGS. 9B and 10B, there is illustrated a first reference x-coordinate plane (x1) generally transecting vertically through the midpoint 905a of the proximal end of the catheter inside space 905 and the midpoint 908m of the proximal end of the proximal clip interior space 908l. A first reference y-coordinate plane (y1) generally transects perpendicularly the first x-coordinate plane (x1) through proximal midpoint 905a. A second reference y-coordinate plane (y2) generally transects perpendicularly the first x-coordinate plane (x1) through proximal midpoint 908m. As shown in the embodiment illustrated in FIG. 9B, the proximal end clip tube 908 and ratchet connector 916 are generally vertically bisected by the first reference x-coordinate plane (x1) along their respective lengths, and the proximal end clip tube 908 and ratchet connector 916 are generally horizontally bisected by the first reference y-coordinate plane (y1) along their respective lengths. The proximal end 902 of catheter conduit 912 is generally vertically bisected by the first reference x-coordinate plane (x1) and generally horizontally bisected by the second reference y-coordinate plane (y2).

Also referring to FIGS. 9B and 10B, there is illustrated a second reference x-coordinate plane (x2) generally transecting vertically through the midpoint 905b of the distal end of the catheter inside space 905 and the midpoint 906m of the distal end of the distal clip interior space 906l. A third reference y-coordinate plane (y3) generally transects perpendicularly the second x-coordinate plane (x2) through distal midpoint 905b. A fourth reference y-coordinate plane (y4) generally transects perpendicularly the second x-coordinate plane (x2) through distal midpoint 906m. As shown in the embodiment illustrated in FIG. 10, the distal end clip tube 906 is generally vertically bisected by the second reference x-coordinate plane (x2) along the length of the distal end clip tube 906 and the distal end clip tube 906 is generally horizontally bisected by the fourth reference y-coordinate plane (y4) along the length of the distal end clip tube 906. The distal end 904 of catheter conduit 912 is generally vertically bisected by the second reference x-coordinate plane (x2) and generally horizontally bisected by the third reference y-coordinate plane (y3).

In one embodiment, the catheter conduit 912 is straight (where the proximal clip axis 938 is axial with the distal clip axis 940, where the first reference x-coordinate plane (x1) lies in the same plane as the second reference x-coordinate plane (x2) and where the first reference y-coordinate plane (y1) lies in the same plane as the third reference y-coordinate plane (y3)).

In another embodiment, the catheter conduit 912 is curved. The curvature could occur where, e.g., the proximal end clip axis 938 is not axial with the distal end clip axis 940, where the first reference x-coordinate plane (x1) deviates from the second reference x-coordinate plane (x2), the first reference y-coordinate plane (y1) deviates from the third reference y-coordinate plane (y3), and/or some combination of vertical and horizontal deviation along the length of the catheter conduit 912.

The catheter conduit 912 can also comprise one or more strands of a flexible, memory retaining material capable of being manipulated to facilitate the defining of the arcuate path or otherwise to facilitate the shaping of the catheter conduit.

Referring now to FIGS. 16A through 27A there is depicted another catheter device 900a. In this preferred embodiment, the catheter device can be similar to that of the catheter device 900 depicted in, e.g., FIG. 9A except that in this embodiment, the locking ratchet connector 916 is replaced with a locking strap mechanism 800 for securing a portion of the proximal end of an endotracheal tube 101 to the catheter device 900a. Referring still to FIGS. 16A through 27A, the locking strap mechanism 800 is fixably attached to or otherwise an integral part of the proximal end of the proximal end flexible c-shaped clip 908.

The locking strap mechanism 800 comprises a shoulder section (808 and 810) for receiving a portion of the endotracheal tube 101, a strap section 802 for wrapping over the endotracheal tube 101, and a strap locking section for receiving the end 802b of the strap 802 into strap locking slot 804. In this embodiment, the shoulder section is depicted as two separate shoulders or receiving channels: the distal receiving channel 808 and the proximal receiving channel 810. The distal receiving channel surface 808a and proximal receiving channel surface 810a are shown generally semicircular in shape, axially aligned with the proximal end flexible c-shaped clip 908 and would be sized to receive the outer diameter of a desired endotracheal tube 101. Although a semicircular shape is shown here, other shapes could be used so long as the receiving channel or channels could serve to receive the endotracheal tube. Also, the size of the semicircular surfaces could be large enough to accommodate the largest diameter endotracheal tube (such as adult sizes) while also being capable of receiving smaller endotracheal tube diameters (such as pediatric sizes). If an undersized endotracheal tube is placed in the receiving channels, as will be discussed below, the locking strap 802 can still serve to lock the endotracheal tube in place. The receiving channel surfaces 810a and 808a can also be contain a gripping material to assist in maintaining the endotracheal tube in place.

As depicted, the distal receiving channel 808 and the proximal receiving channel 810 appear as inverted arches or semicircular channels that are connected by the strap lock housing 804a. In the embodiment shown, each receiving channel has left and right shoulders. The distal receiving channel left side shoulder 808b has a distal receiving channel left side shoulder height 808c. The distal receiving channel right side shoulder 808d has a distal receiving channel right side shoulder height 808e. The proximal receiving channel left side shoulder 810b has a proximal receiving channel left side shoulder height 810c. The proximal receiving channel right side shoulder 810d has a proximal receiving channel right side shoulder height 810e. In the embodiment shown, it is preferred, but not required that the distal receiving channel left side shoulder height 808c is greater than the distal receiving channel right side shoulder 808e. Likewise, in the embodiment shown, it is preferred, but not required that the proximal receiving channel left side shoulder height 810c is greater than the proximal receiving channel right side shoulder height 810e. In the embodiment shown, it is preferred, but not required that the distal receiving channel left side shoulder height 808c is approximately equal to the proximal receiving channel left side shoulder height 810c and that the distal receiving channel right side shoulder height 808e is approximately equal to the proximal receiving channel right side shoulder height 810e.

The distal receiving channel 808 and proximal receiving channel 810 are axially aligned together and axially aligned with the proximal clip axis 938. In one embodiment, the distal receiving channel 808 comprises an extension of (or one and the same as) the proximal end flexible c-shaped clip 908 and the distal receiving channel surface 808a is an extension of (or one and the same as) the proximal end flexible c-shaped clip interior wall gripping surface 908h. The strap lock housing 804a connects the lower left sections of the distal receiving channel left side 808c and the proximal receiving channel left side. The strap 802 has a first or fixed end 802a connected to the strap housing between the distal receiving channel 808 and the proximal receiving channel 810. The strap 802 has a second or free end 802b opposite the fixed end 802a. The strap 802 has a top surface 802c and a bottom surface 802d. Preferably the strap free end 802b is tapered (as shown) to facilitate entry of the strap free end 802b into the strap locking slot 804 but it could be a square end, v-shaped end, or rounded end. The strap lock slot 804 is contained in the strap lock housing 804a and is sized to permit the strap 802 to pass therethrough.

The top side of the strap 802c can further comprise one or more strap ridges 806 or other gripping surfaces proximate the strap fixed end 802a so that can such strap ridges or other gripping surfaces can engage the endotracheal tube to assist in locking it in place. As shown in the preferred embodiment, a plurality of strap ridges are placed in spaced-apart relationship on the strap top side 802c starting from the strap fixed end 802a and continuing over a length of the strap underside corresponding to the outer circumference of the endotracheal tube 101.

The bottom side of the strap 802d contains a plurality of spaced-apart strap locking teeth 814, the space between adjacent teeth comprising a strap lock groove 814a. The teeth 814 are preferably of a saw-tooth configuration with the sloped edge of the tooth facing toward the strap locking slot 804, and the straight edge side of the tooth is perpendicular to the strap. It is preferred to have a sufficient number of strap locking teeth 814 located on the strap bottom side 802d so that when the strap 802 is fed through the strap lock slot 804 and pulled taught over the surface of an endotracheal tube 101, there will be sufficient strap lock teeth 814 present to engage the strap lock locking mechanism.

In this embodiment, the strap locking mechanism comprises a strap lock pawl 812 pivotally connected to the strap lock housing 804a adjacent to the underside of the strap lock slot opening 804. The strap lock pawl 812 further comprises a strap lock pawl tab pivot connection 812c and a strap lock pawl finger tab 812b for use in using one's fingers to pivot the pawl tab about its pivot. The strap lock pawl has a first section extending from the pivot 812c generally parallel to the slot opening 804. The pivot 812c maintains itself in a first position, and can be pivoted outward by the user's fingers. At the end of this first pawl section, and protruding inward into the slot space is a strap lock pawl tooth 812a sized and configured with a slope (sloping downward relative to the slot opening 804) designed to permit the strap locking teeth sloped edges to pass by undeterred when the strap is being introduced into and down through the locking slot (i.e., as the strap is being tightened around the outside of the endotracheal tube 101). The underside of the pawl tooth 812a is a flat face, generally perpendicular to the first section of the pawl tab 812. When the desired tension is pulled on the strap 802, so that the strap secures the endotracheal tube into the receiving channels (808, 810), the strap locking tooth's non-sloped (perpendicular) flat tooth edge engages against the flat underside face of the pawl tooth 812a to lock the strap 802 in place. The strap 802 may be loosened from the strap lock pawl tooth by pivoting the pawl tab 812 outward so that the pawl tooth 812a moves out of engagement with the strap lock grooves 814a. The bottom surface of the strap 802d is outfitted with a plurality of spaced apart strap locking teeth 814 positioned such that sufficient number of teeth will be present adjacent the strap pawl tooth to permit locking engagement for a variety of endotracheal tube sizes.

In one embodiment, the plurality of spaced-apart strap locking teeth 814 begins adjacent to the strap fixed end 802a and continues for a substantial length of the strap to permit greater bending flexibility of the strap as it is placed over the outside of the endotracheal tube, and to permit a wide range of endotracheal tube diameters.

The adjustable locking strap mechanism 800 is preferably attached to, and in axial alignment, with the proximal end clip 908 and capable of receiving the endotracheal tube 101 and comprises: one or more receiving channels 808, 810 capable of receiving the outer surface of the endotracheal tube, a strap 802 having a fixed end 802a connected to the one or more receiving channels and extending outwardly in an orientation substantially perpendicular to the proximal end clip axis 938 from a first side of the one or more receiving channels, and a loose end 802b opposite the fixed end, the strap 802 having a top surface 802c for engaging the outer surface of the endotracheal tube and a bottom surface 802d opposite the top surface, a strap housing 804a located on a second side of the one or more receiving channels opposite the first side of the one or more receiving channels, the housing containing a strap locking slot 804 capable of receiving into the slot in a first direction the loose end 802b of the strap and locking the strap in place, the strap having a length sufficient to extend from the strap fixed end 802a, over the top of the outer surface of the received endotracheal tube 101, and into the strap locking slot 804, the strap locking slot 804 also capable of releasing its lock on the strap. The strap bottom side 802d contains a plurality of spaced apart locking teeth 814, the space between the teeth defining a series of grooves 814a, and wherein the strap locking slot 804a contains a biased strap lock pawl tooth 812a capable of engaging one of the strap grooves 814a to prevent the strap 802, when the groove 814a is engaged by the pawl tooth 812a, from exiting out of the strap locking slot 804 in a second direction opposite the first direction. The biased strap lock pawl tooth 812a is mounted on a strap lock pawl 812, the strap lock pawl 812 being pivotally mounted within the strap lock housing 804a, the strap lock pawl 812 containing a pawl finger tab 812b so that the strap lock pawl tooth 812a may be manually unbiased from the strap groove 814a to permit the strap 802 to be removed from the locking slot 804 in the second direction.

The length of the strap 802b can vary, but it is preferred to have sufficient length to permit medical personnel using the device to easily feed the strap through the slot 804 and to pull it tight and lock it with the strap lock pawl tooth 812a.

Many other strap lock configurations are possible. For example, and without limitation, although the catheter conduit device embodiment 900a shown in, e.g., FIG. 17 contains two receiving channels 810, 808 in the locking mechanism 800 for receiving the endotracheal tube 101, a single channel could be employed in which the single channel was equipped with a mechanism for securing the endotracheal tube, such as the strap and strap lock described above. More specifically for example, the locking strap mechanism 800 could be modified to connect together in axial fashion the proximal and distal channel surfaces 810a, 808a while also maintaining a strap and strap lock mechanism of the sort shown in FIG. 17, or the like. Also, reclosable tie wrap technology, such as the hook and loop reclosable cable tie wraps offered and sold by Leviton (levitonproducts.com) could be used in the design of the strap lock mechanism. Also, although not as preferred as a strap lock mechanism 800 that is integral with the catheter conduit device 900a, individual reclosable or single use cable tie wraps could be used to secure the endotracheal tube to the catheter conduit device.

The strap lock mechanism 800 and the locking ratchet connector 916 are but two examples of how one can removably secure or lock a portion of the endotracheal tube 101 to the catheter device. Other suitable mechanisms for creating a reclosable locking fastener of this type for removably securing an endotracheal tube to a catheter conduit device such as those described herein will be apparent to one of ordinary skill in the art having the benefit of this disclosure.

Much like shown in, e.g., FIG. 9A and described above in connection with loops 914, the catheter conduit device 900a can also contain one or more loops 914a for securing the ends of an adjustable strap (not shown), the loops 914a shown here in somewhat square configuration (as compared with the somewhat circular configuration of loop 914).

Figure 17:
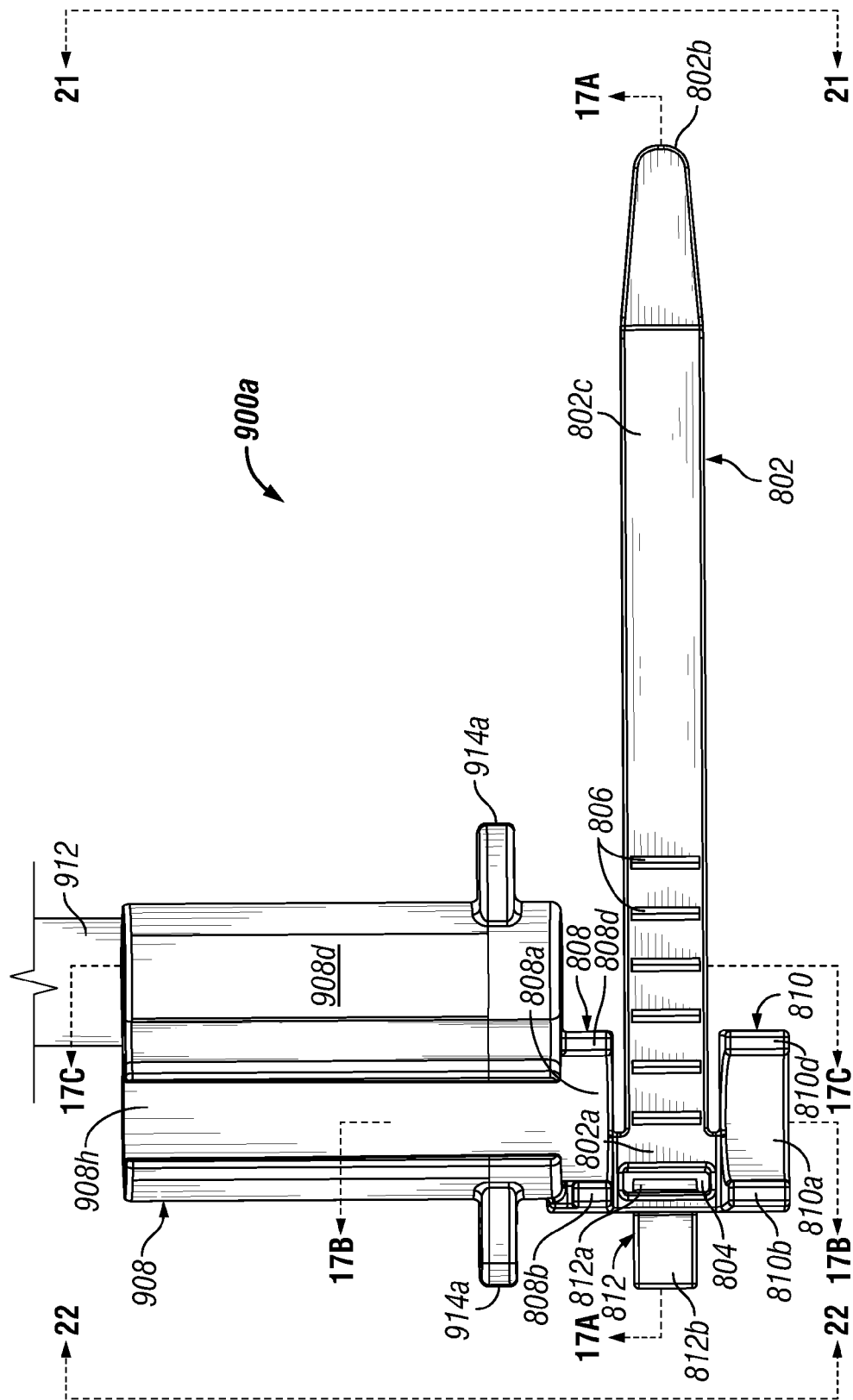
FIG. 17 illustrates an enlarged top side view of the proximal end of the catheter shown in FIG. 16A.
Figure 17A:
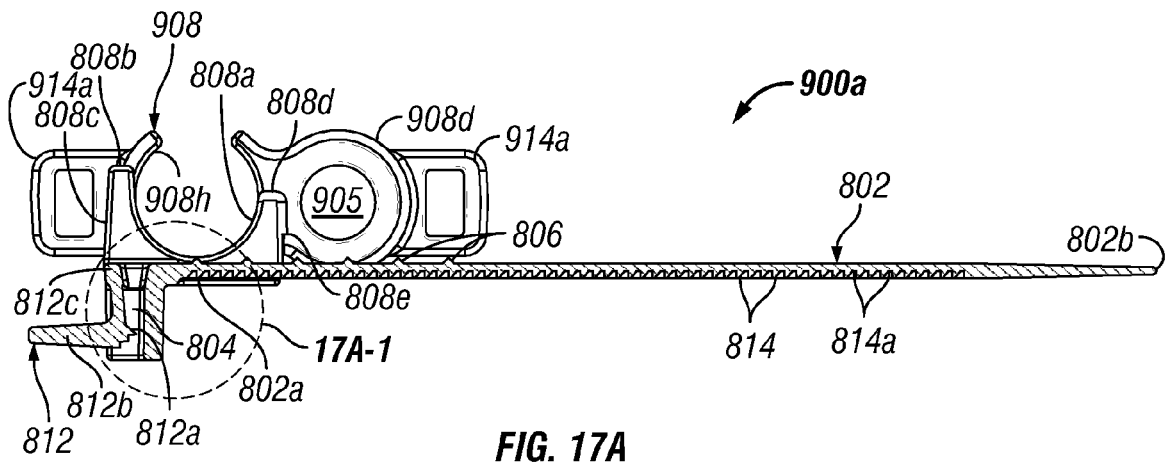
FIG. 17A illustrates a cross-sectional proximal end view of the catheter shown in FIG. 17 taken along line 17A-17A of FIG. 17.
Figures 1, 17A:
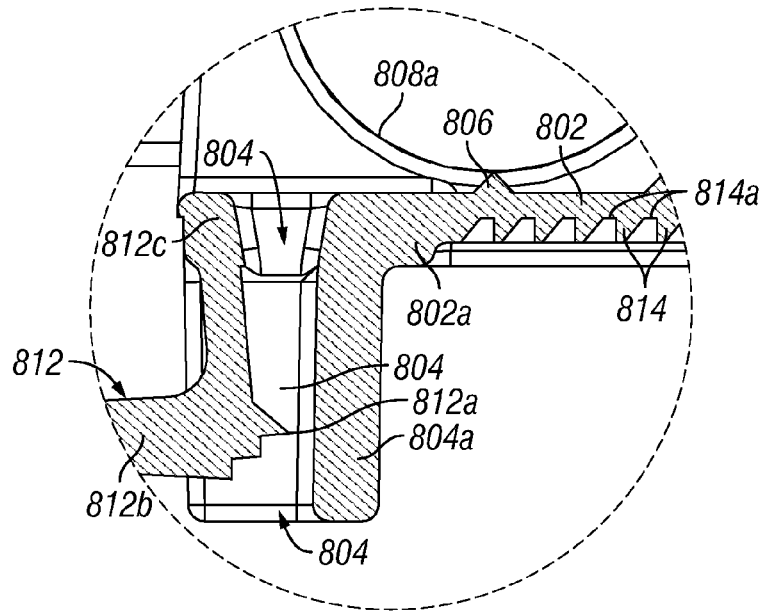
Figure 17B:
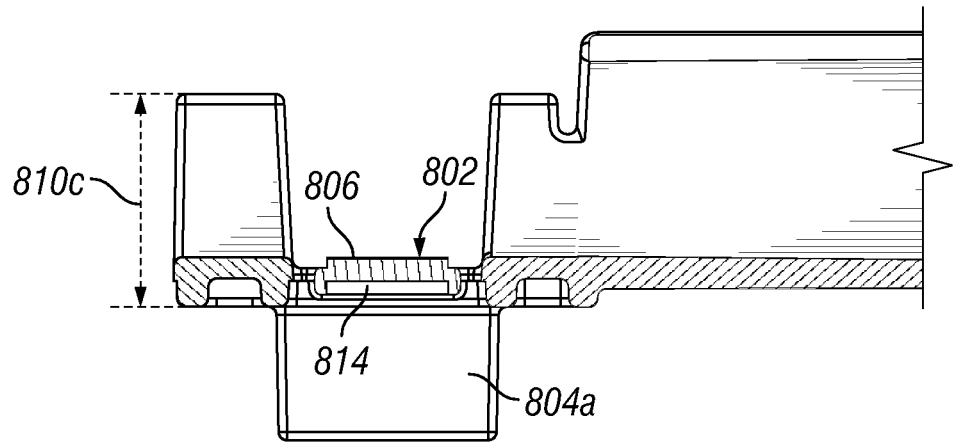
FIG. 17B illustrates a cross-sectional view of the catheter shown in FIG. 17 taken along line 17B-17B of FIG. 17.
Figure 17C:
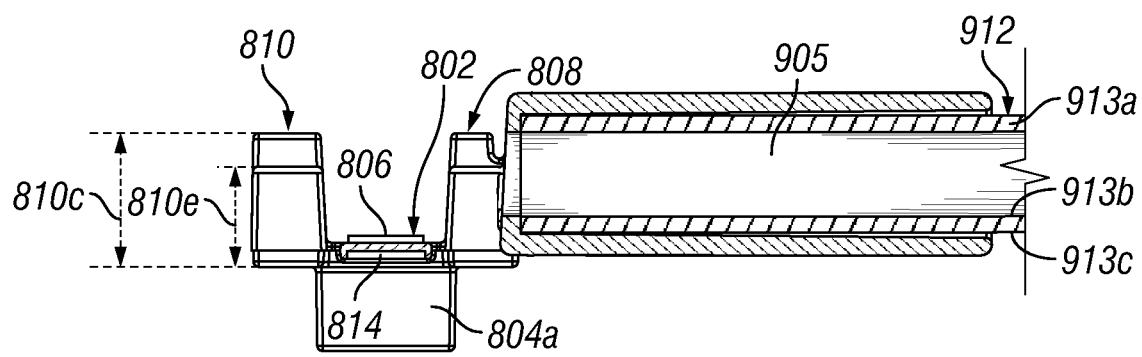
FIG. 17C illustrates a cross-sectional view of the catheter shown in FIG. 17 taken along line 17C-17C of FIG. 17.
Figure 18:
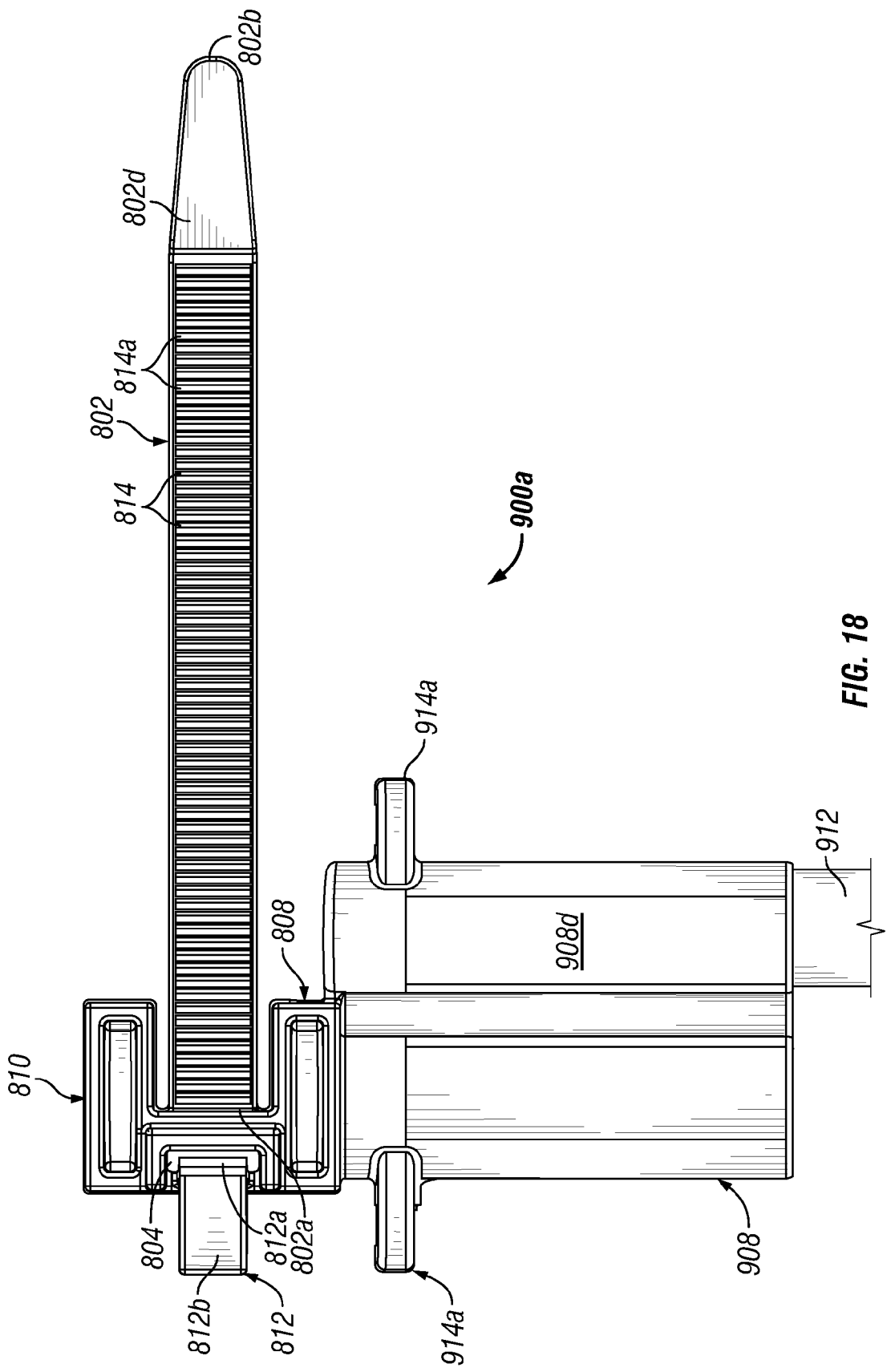
FIG. 18 illustrates an enlarged bottom side view of the proximal end of the catheter shown in FIG. 16B.
Figure 21:
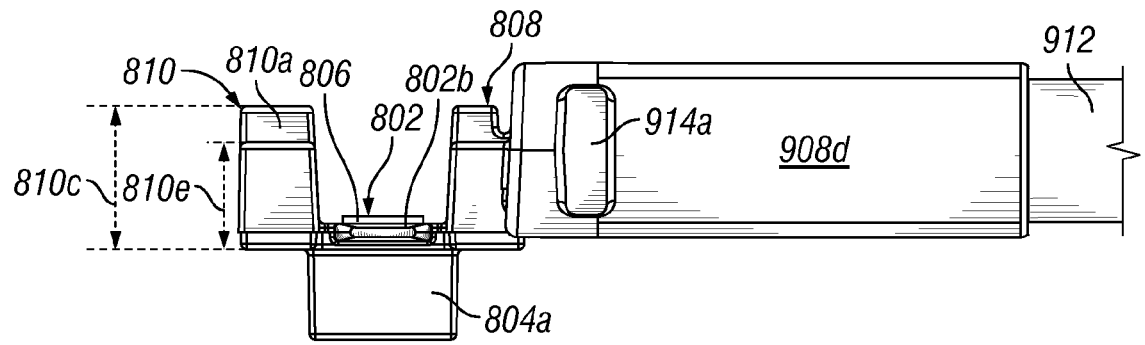
FIG. 21 illustrates a right side view of the catheter shown in FIG. 17.
Figure 22:
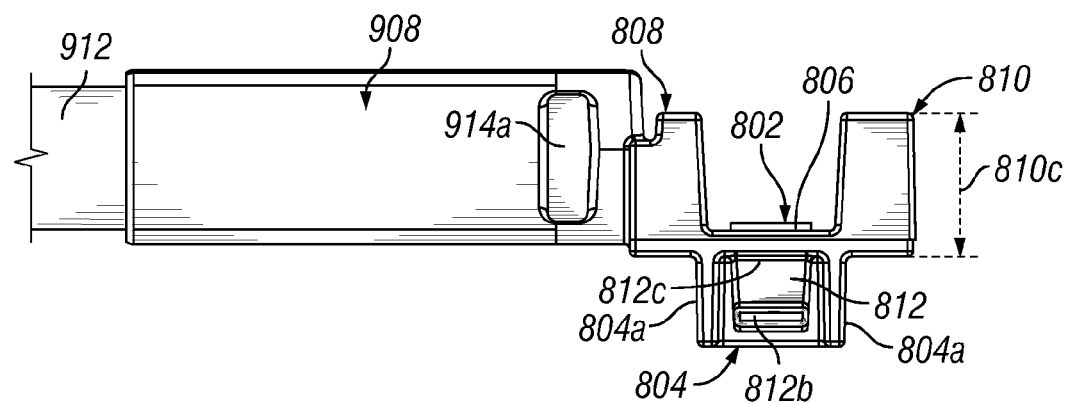
FIG. 22 illustrates a left side view of the catheter shown in FIG. 17.
Figure 23A:
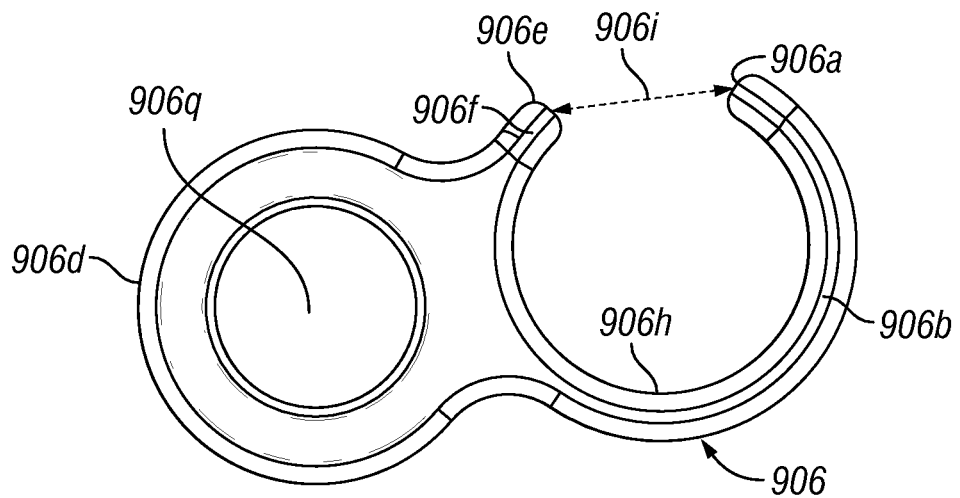
FIG. 23A illustrates a distal end view of the catheter c-shaped clip seen in, e.g., FIGS. 16A and 16B used for housing a portion of an endotracheal tube (not shown).
Figure 23B:
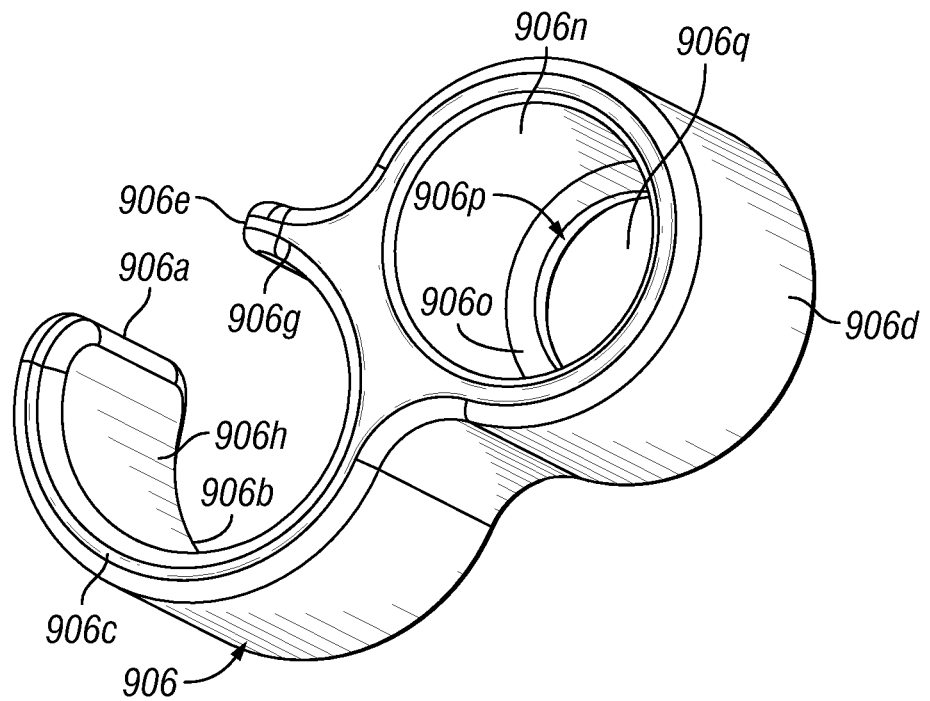
FIG. 23B illustrates a proximal end perspective view of the catheter c-shaped clip seen in, e.g., FIGS. 16A, 16B and 23A used for housing a portion of an endotracheal tube (not shown).
Figure 24:
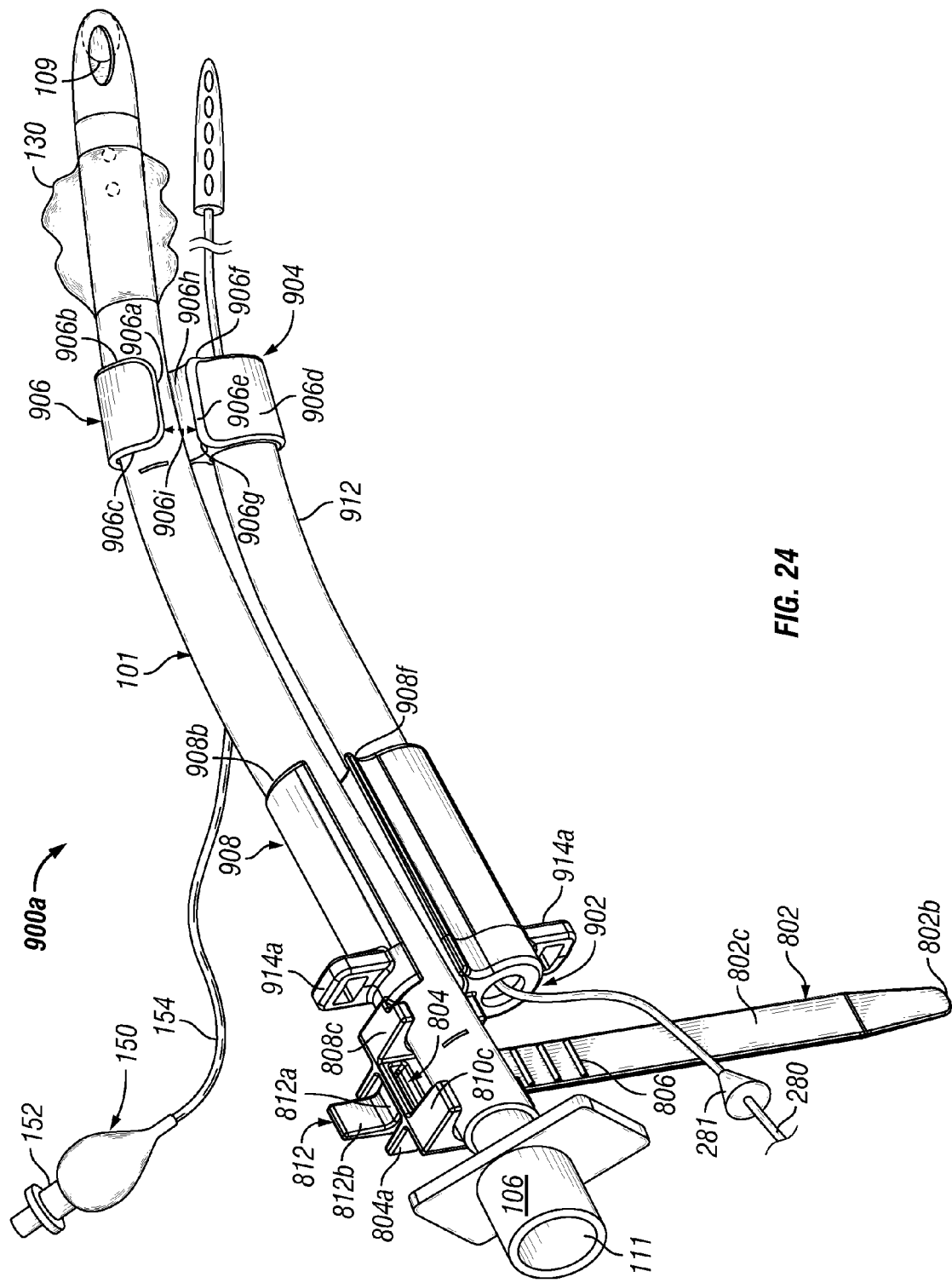
FIG. 24 illustrates a perspective top side (anterior) view of the catheter shown in FIG. 16A, housing an endotracheal tube (not shown to scale) shown with the locking strap used for securing the endotracheal tube in a disengaged position.
Figure 25:
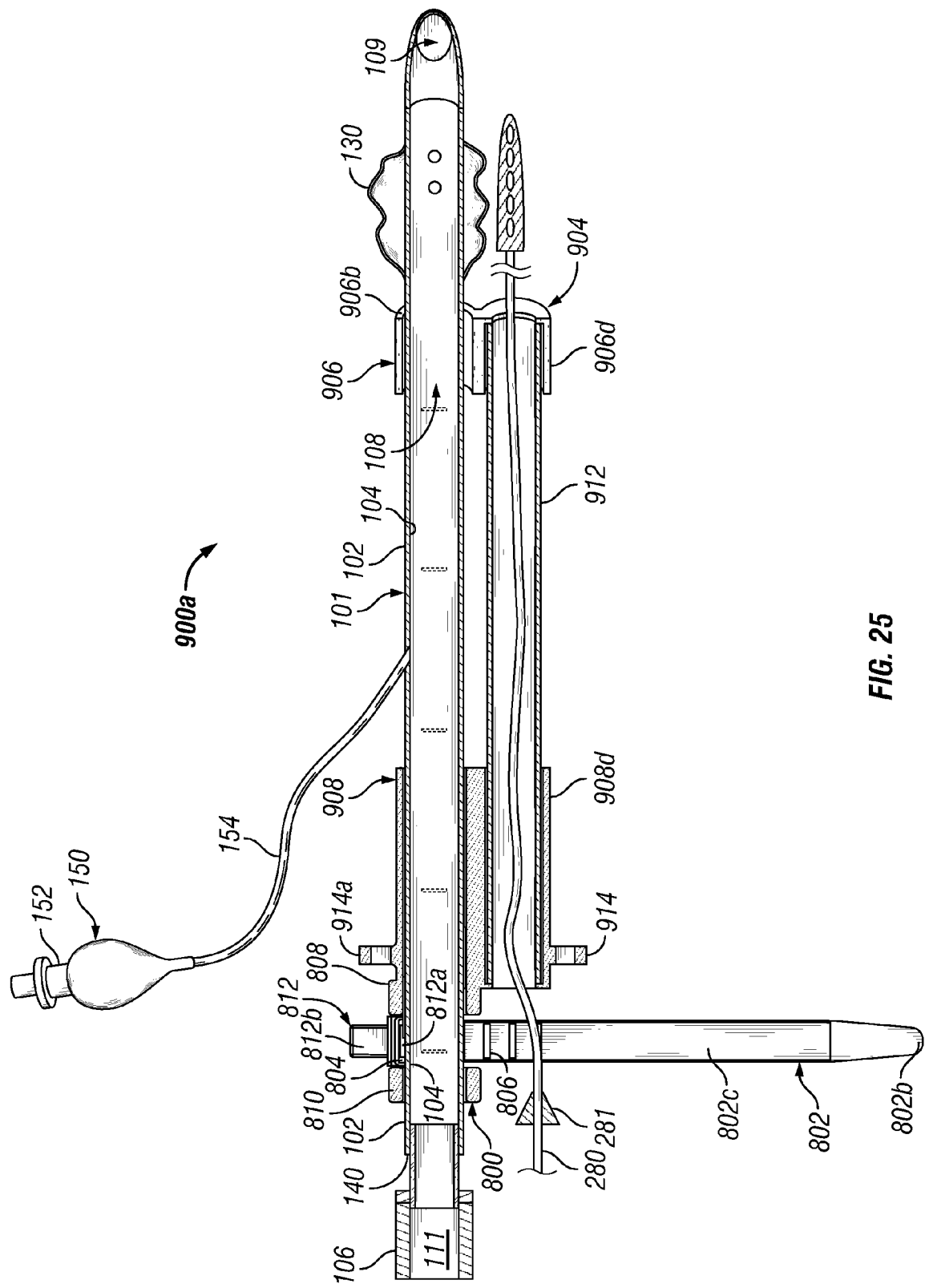
FIG. 25 illustrates a cross-sectional top side view of the catheter shown in FIG. 24, housing an endotracheal tube (not shown to scale) shown with the locking strap used for securing the endotracheal tube in a disengaged position.
Figure 26:
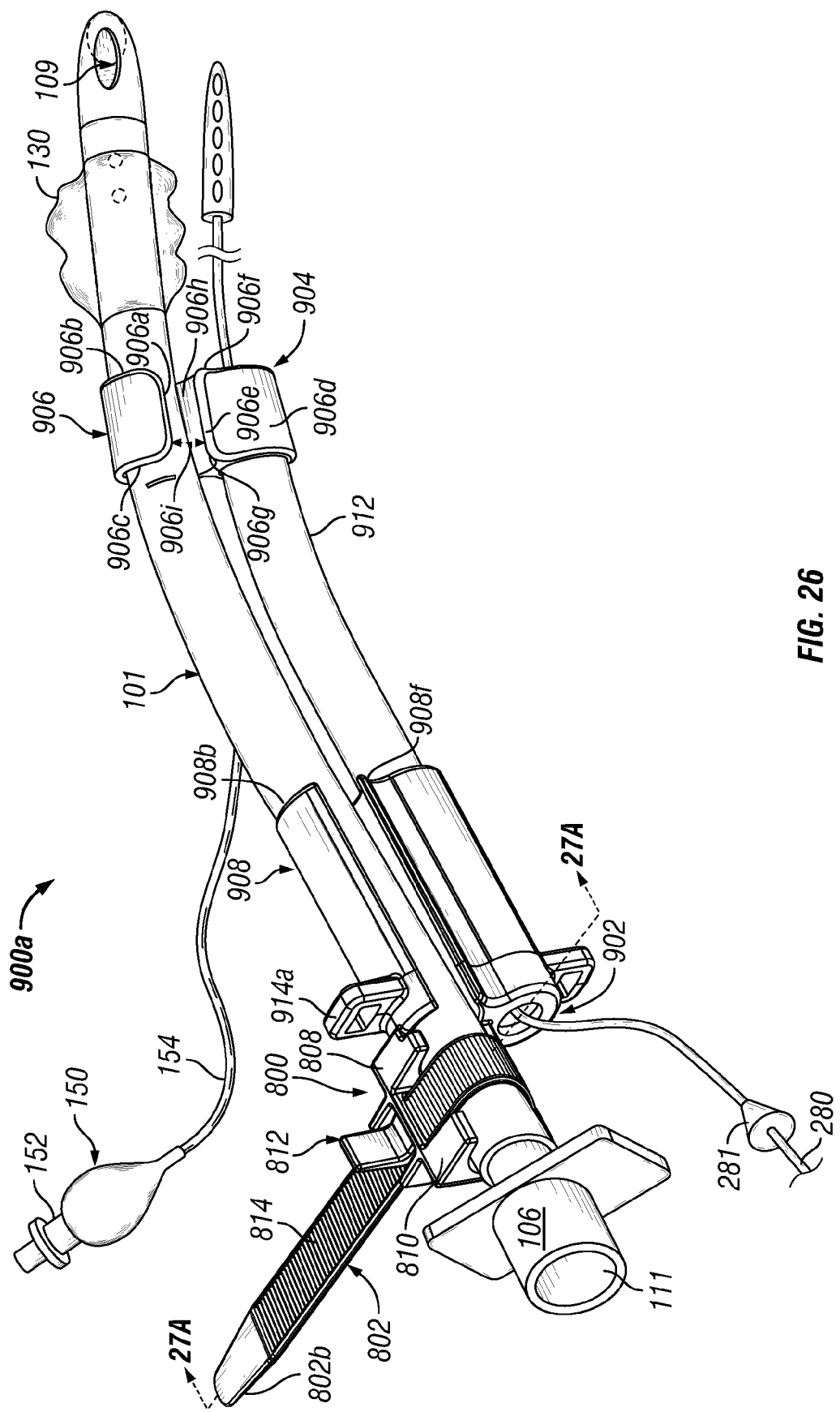
FIG. 26 illustrates a perspective top side (anterior) view of the catheter shown in FIG. 16A, housing an endotracheal tube (not shown to scale) shown with the locking strap used for securing the endotracheal tube in an engaged position.
Figure 27:
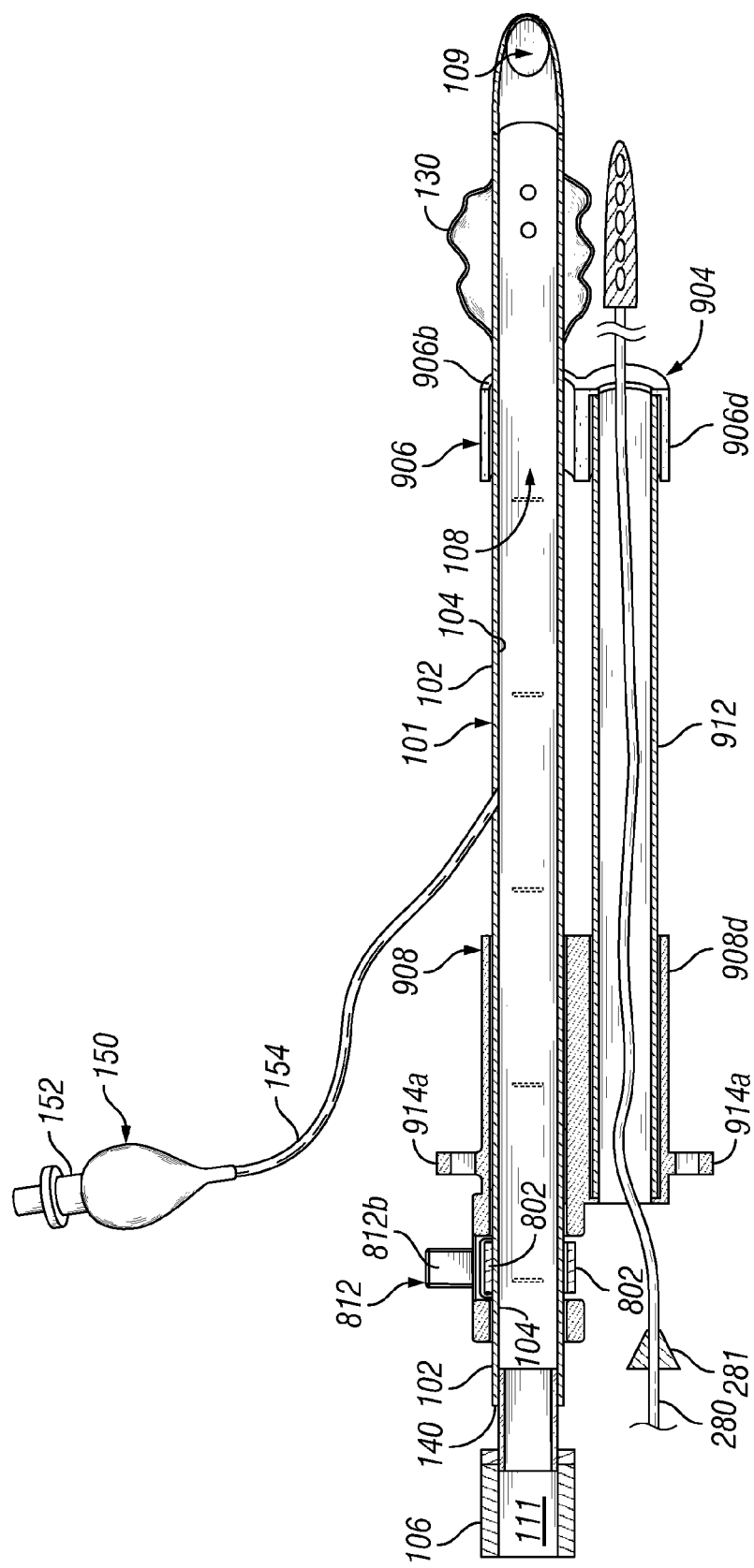
FIG. 27 illustrates a cross-sectional view of the catheter shown in FIG. 26, housing an endotracheal tube (not shown to scale) shown with the locking strap used for securing the endotracheal tube in an engaged position.
Figure 27A:
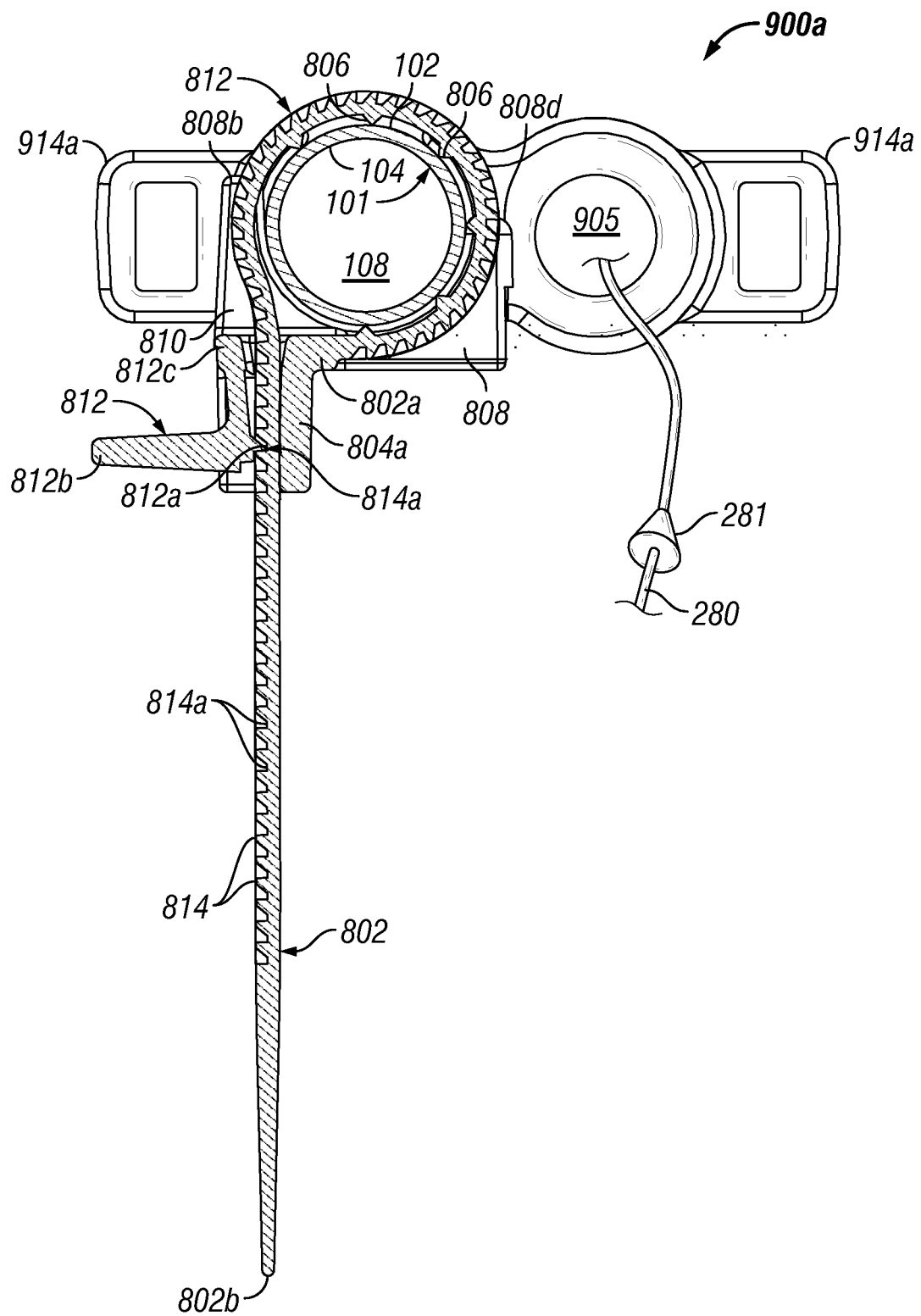
FIG. 27A illustrates a cross-sectional proximal view taken along line 27A-27A of FIG. 27 showing the locking strap used for securing the endotracheal tube in an engaged position (with FIG. 17A, showing a similar cross-sectional view except to show the locking strap in a disengaged position).

Also referring to FIGS. 23A and 23B, another embodiment of the distal end flexible c-shaped clip 906 is shown detached from the conduit 912. The distal end of the catheter conduit 912 would be placed into the distal end flexible c-shaped clip mount 906d and secured with glue or other suitable material to secure it to the interior surface 906n of the distal end flexible c-shaped clip mount 906d. The distal end flexible c-shaped clip mount 906d has a lip 906o of width 906p that serves as a stop when placing the catheter conduit 912 into the distal end flexible c-shaped clip mount 906d. The distal end flexible c-shaped clip mount 906d has an opening 906q that is preferably equal in diameter to the diameter of the catheter conduit distal end opening 913d so that an orogastric or enteral tube 280 passing through the catheter conduit does not snag an edge of the distal end flexible c-shaped clip mount opening 906q. This distal end flexible c-shaped clip mount embodiment is also depicted in, e.g., FIGS. 16B, 25 and 27. Similarly, the catheter conduit attachment sleeve/proximal end flexible c-shaped clip mount 908d can be configured with a lip such as is generally shown in, e.g., FIG. 17C to facilitate construction of the catheter conduit device 900a. In the embodiment of the catheter conduit 900 shown in, e.g., FIG. 15, no lips are employed on the distal end flexible c-shaped clip mount 906d or on the proximal end flexible c-shaped clip mount 908d. These two embodiments illustrate two exemplary ways in which the proximal and distal end clip structures can be secured to the catheter conduit, but other suitable mechanisms are possible as will be understood by one skilled in the art having the benefit of this disclosure.

Additionally, the attachable catheter devices 900, 900a could be of a unitary construction.

Also, although the catheter device 900, 900a has been described as being a separate structure from the endotracheal tube 101, another embodiment of this invention includes a combination device where the catheter device 900, 900a is already attached to the endotracheal tube either in a fixed positional relationship, or where the catheter device is slidably attached to the outside of the endotracheal tube 101 so that the relative positioning of the catheter device can be adjusted along the outside of the endotracheal tube, and if desired, a clamp (such as the adjustable ratchet clamp 916 or locking strap mechanism 800) can be employed to lock such positioning in place.

The following represents an exemplary list of references.

U.S. PATENT REFERENCES

1. Angel—US 2004/0000314 A1
2. Fortuna—US 2004/0020491 A1
3. Ranzinger—US 2003/0183234 A1
4. Snidach—US 2003/0062039 A1
5. Alfery—U.S. Pat. No. 6,729,325
6. Klepper—U.S. Pat. No. 6,460,540
7. Bowden et al.—U.S. Pat. No. 6,374,827
8. Frass et al.—U.S. Pat. No. 5,499,625
9. Insler et al.—U.S. Pat. No. 5,588,424
10. Price—U.S. Pat. No. 5,353,787
11. Price—U.S. Pat. No. 5,253,643
12. Peckham—U.S. Pat. No. 5,143,062
13. White et al.—U.S. Pat. No. 4,774,945
14. McGrail—U.S. Pat. No. 4,584,998
15. Scarberry—U.S. Pat. No. 4,351,330
16. Dryden—U.S. Pat. No. 4,256,099
17. Scarberry—U.S. Pat. No. 4,231,365
18. Elam—U.S. Pat. No. 4,090,518
19. Sheridan—U.S. Pat. No. 3,625,793
20. Gadberry et al.—U.S. Pat. No. 6,461,363

NON-U.S. PATENT REFERENCES

21. Ranzinger—JPO abstract 2002-315832
22. Frankel—EPO 0 230 790
23. Skoljarev—DE19533615—English language abstract.
24. Webpage regarding the adjustable nylon ratchet clamps available from ElectricalBasics.com.
25. Webpage showing hook and loop reclosable cable tie wraps offered and sold by Leviton (levitonproducts.com).

All references referred to herein are incorporated herein by reference. While the apparatus and methods of this invention have been described in terms of preferred embodiments, it will be apparent to those of skill in the art that variations may be applied to the process and system described herein without departing from the concept and scope of the invention. All such similar substitutes and modifications apparent to those skilled in the art are deemed to be within the scope and concept of the invention. Those skilled in the art will recognize that the method and apparatus of the present invention has many applications, and that the present invention is not limited to the representative examples disclosed herein. Moreover, the scope of the present invention covers conventionally known variations and modifications to the system components described herein, as would be known by those skilled in the art. While the apparatus and methods of this invention have been described in terms of preferred or illustrative embodiments, it will be apparent to those of skill in the art that variations may be applied to the process described herein without departing from the concept and scope of the invention. All such similar substitutes and modifications apparent to those skilled in the art are deemed to be within the scope and concept of the invention as it is set out in the following claims.

I claim:

1. A medical catheter device, attachable to an endotracheal tube having a proximal end and a distal end, for guiding the path of an enteral tube into the esophagus of a patient, comprising:

(a) a catheter conduit comprising a proximal end with a proximal end opening for receiving the enteral tube, and a distal end opposite the proximal end having a distal end opening opposite the proximal end opening, the distal end opening permitting the enteral tube to enter the esophagus of the patient; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit;

(b) a proximal end clip attached to the catheter conduit proximate the proximal end of the catheter conduit for receiving and removably attaching a portion of the endotracheal tube near the proximal end of the endotracheal tube, the proximal end clip having a first proximal clip end oriented toward the catheter conduit proximal end and a second proximal clip end oriented toward the catheter conduit distal end; wherein the proximal end clip has a proximal end clip axis which extends axially through the proximal end clip from the proximal end clip first end toward the proximal end clip second end; and (c) a distal end clip attached to the catheter conduit proximate the distal end of the catheter conduit for receiving and removably attaching another portion of the endotracheal tube located toward the distal end of the endotracheal tube, the distal end clip having a first distal clip end oriented toward the catheter conduit proximal end and a second distal clip end oriented toward the catheter conduit distal end; wherein the distal end clip has a distal end clip axis which extends axially through the distal end clip from the distal end clip first end toward the distal end clip second end;

said distal end of said catheter being positioned proximate the opening of the patient's esophagus when the distal end of said endotracheal tube is inserted into the patient's trachea and the catheter is attached to the endotracheal tube.

2. The catheter device of claim 1 further comprising a locking mechanism to lock the catheter conduit into a desired position relative to the endotracheal tube.

3. The catheter device of claim 2, wherein the locking mechanism comprises an adjustable locking strap mechanism attached to, and in axial alignment, with the proximal end clip and capable of receiving the endotracheal tube, said locking strap mechanism comprising:

(a) one or more receiving channels capable of receiving the outer surface of the endotracheal tube, (b) a strap having a fixed end connected to the one or more receiving channels and extending outwardly in an orientation substantially perpendicular to the proximal end clip axis from a first side of the one or more receiving channels, and a loose end opposite the fixed end, the strap having a top surface for engaging the outer surface of the endotracheal tube and a bottom surface opposite the top surface, (c) a strap housing located on a second side of the one or more receiving channels opposite the first side of the one or more receiving channels, the housing containing a strap locking slot capable of receiving into the slot in a first direction the loose end of the strap and locking the strap in place, the strap having a length sufficient to extend from the strap fixed end, over the top of the outer surface of the received endotracheal tube, and into the strap locking slot, the strap locking slot also capable of releasing its lock on the strap.

4. The catheter device of claim 3, wherein the strap bottom side contains a plurality of spaced apart locking teeth, the space between the teeth defining a series of grooves, and wherein the strap locking slot contains a biased strap lock pawl tooth capable of engaging one of the strap grooves to prevent the strap, when the groove is engaged by the pawl tooth, from exiting out of the strap locking slot in a second direction opposite the first direction.

5. The catheter device of claim 4, wherein the biased strap lock pawl tooth is mounted on a strap lock pawl, the strap lock pawl being pivotally mounted within the strap lock housing, the strap lock pawl containing a pawl finger tab so that the strap lock pawl tooth may be manually unbiased from the strap groove to permit the strap to be removed from the locking slot in the second direction.

6. The catheter device of claim 5 further comprising an endotracheal tube having a portion of its distal end attached to the catheter distal end clip and having a portion of its proximal end attached to the catheter proximal end clip.

7. The catheter device of claim 2, wherein the locking mechanism comprises an adjustable locking ratchet pawl type clamp in axial alignment with the first end of the proximal end clip and capable of receiving the endotracheal tube so that the ratchet clamp can lock the catheter device into the desired position relative to the endotracheal tube.

8. The catheter device of claim 1 wherein the catheter device further comprises a malleable stylet for use in shaping the catheter conduit, the stylet having a distal end and a proximal end.

9. The catheter device of claim 8 wherein the stylet employs fiber optics capable of transmitting an optical image signal from the distal end of the stylet to a display device connected to the proximal end of the stylet.

10. The catheter device of claim 9 wherein the stylet is integrated into the catheter conduit.

11. The catheter device of claim 9 wherein the stylet is built into the wall of the catheter conduit.

12. The catheter device of claim 9 wherein the stylet is insertable into and removable from the interior space of the catheter conduit.

13. The catheter device of claim 1, wherein the conduit proximal end axis intersects with the conduit distal end axis to form a conduit angle.

14. The catheter device of claim 13, wherein the conduit angle ranges between about 0 degrees and about 30 degrees.

15. The catheter device of claim 13, wherein the conduit angle is about 10 degrees.

16. The catheter device of claim 1, wherein the proximal end clip axis intersects with the distal clip axis to form a clip angle.

17. The catheter device of claim 16, wherein the clip angle ranges between about 0 degrees and about 30 degrees.

18. The catheter device of claim 16, wherein the clip angle is about 10 degrees.

19. The catheter device of claim 1, wherein the catheter conduit is substantially tubular in shape.

20. The catheter device of claim 1, wherein the catheter conduit is linear along its length.

21. The catheter device of claim 1, wherein the catheter conduit is curved along its length.

22. The catheter device of claim 1, wherein the catheter conduit is a flexible.

23. The catheter device of claim 1, wherein the conduit proximal end axis is aligned with the conduit distal end axis.

24. The catheter device of claim 1, wherein the proximal end clip comprises a c-shaped hollow proximal clip tube capable of clipping over and gripping the outside surface of the portion of the endotracheal tube near the proximal end of the endotracheal tube; wherein the distal end clip comprises a c-shaped hollow distal clip tube capable of clipping over and gripping the outside surface of the portion of the endotracheal tube near the distal end of the endotracheal tube.

25. The catheter device of claim 1, wherein the proximal end clip axis is aligned with the distal clip axis.

26. The catheter device of claim 1, wherein the proximal end clip axis is substantially parallel with the conduit proximal end axis.

27. The catheter device of claim 1, wherein the distal end clip axis is substantially parallel with the conduit distal end axis.

28. The catheter device of claim 1, wherein the proximal end clip axis is not substantially parallel with the conduit proximal end axis.

29. The catheter device of claim 1, wherein the distal end clip axis is not substantially parallel with the conduit distal end axis.

30. The catheter device of claim 1, wherein the proximal end clip also serves as a bite block device to inhibit the potential collapse caused by patient biting of the catheter conduit or the endotracheal tube contained therein.

31. The catheter device of claim 1 further comprising an endotracheal tube having a portion of its distal end attached to the distal end of the catheter and having a portion of its proximal end attached to the proximal end of the catheter.

32. The catheter device of claim 1 further comprising an endotracheal tube having a portion of its distal end attached to the catheter distal end clip and having a portion of its proximal end attached to the catheter proximal end clip.

33. The catheter device of claim 1 wherein the catheter conduit further comprises one or more strands of a flexible, memory retaining material capable of being manipulated to facilitate shaping of the catheter conduit.

34. A combination medical device comprising:
 (a) an endotracheal tube for use in ventilating a patient's lungs, said endotracheal tube having an outside diameter, an inside diameter defining an endotracheal ventilation lumen, a proximal end and a distal end, the endotracheal tube capable of defining an arcuate path in a first plane between its proximal end and its distal end to facilitate introduction of the endotracheal tube into the trachea of the patient, the endotracheal tube also having an inflatable cuff for achieving a seal, when inflated, with said endotracheal tube outside diameter and an inner wall of the trachea of the patient when the distal end of said endotracheal tube is inserted into the patient's trachea, said cuff being positioned generally toward the distal end of the endotracheal tube, the inflatable cuff being in fluid communication with an inflation port positioned generally toward the proximal end of the endotracheal tube, and
 (b) a catheter device, attachable to the endotracheal tube having a proximal end and a distal end, for guiding the path of an enteral tube into the esophagus of the patient, the catheter device comprising:
  i. a catheter conduit comprising a proximal end with a proximal end opening for receiving the enteral tube, and a distal end opposite the proximal end having a distal end opening opposite the proximal end opening, the distal end opening permitting the enteral tube to enter the esophagus of the patient; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit;
  ii. a proximal end clip attached to the catheter conduit proximate the proximal end of the catheter conduit for receiving and removably attaching a portion of the endotracheal tube near the proximal end of the endotracheal tube, the proximal end clip having a first proximal clip end oriented toward the catheter conduit proximal end and a second proximal clip end oriented toward the catheter conduit distal end; wherein the proximal end clip has a proximal end clip axis which extends axially through the proximal end clip from the proximal end clip first end toward the proximal end clip second end; and
  iii. a distal end clip attached to the catheter conduit proximate the distal end of the catheter conduit for receiving and removably attaching another portion of the endotracheal tube located toward the distal end of the endotracheal tube, the distal end clip having a first distal clip end oriented toward the catheter conduit proximal end and a second distal clip end oriented toward the catheter conduit distal end; wherein the distal end clip has a distal end clip axis which extends axially through the distal end clip from the distal end clip first end toward the distal end clip second end;
 said distal end of said catheter being positioned proximate the opening of the patient's esophagus when the distal end of said endotracheal tube is inserted into the patient's trachea and the catheter is attached to the endotracheal tube.

35. A method of intubating a patient comprising the steps of:
 (a) providing a combination intubation device, the intubation device comprising,
  i. an endotracheal tube for use in ventilating the patient's lungs, said endotracheal tube having an outside diameter, an inside diameter defining an endotracheal ventilation lumen, a proximal end and a distal end, the endotracheal tube capable of defining an arcuate path in a first plane between its proximal end and its distal end to facilitate introduction of the endotracheal tube into the trachea of the patient, the endotracheal tube also having an inflatable cuff for achieving a seal, when inflated, with said endotracheal tube outside diameter and an inner wall of the trachea of the patient when the distal end of said endotracheal tube is inserted into the patient's trachea, said cuff being positioned generally toward the distal end of the endotracheal tube, the inflatable cuff being in fluid communication with an inflation port positioned generally toward the proximal end of the endotracheal tube, and ii. a catheter device, attachable to the endotracheal tube having a proximal end and a distal end, for guiding the path of an enteral tube into the esophagus of the patient, the catheter device comprising:

a catheter conduit comprising a proximal end with a proximal end opening for receiving the enteral tube, and a distal end opposite the proximal end having a distal end opening opposite the proximal end opening, the distal end opening permitting the enteral tube to enter the esophagus of the patient; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit;

a proximal end clip attached to the catheter conduit proximate the proximal end of the catheter conduit for receiving and removably attaching a portion of the endotracheal tube near the proximal end of the endotracheal tube, the proximal end clip having a first proximal clip end oriented toward the catheter conduit proximal end and a second proximal clip end oriented toward the catheter conduit distal end; wherein the proximal end clip has a proximal end clip axis which extends axially through the proximal end clip from the proximal end clip first end toward the proximal end clip second end; and a distal end clip attached to the catheter conduit proximate the distal end of the catheter conduit for receiving and removably attaching another portion of the endotracheal tube located toward the distal end of the endotracheal tube, the distal end clip having a first distal clip end oriented toward the catheter conduit proximal end and a second distal clip end oriented toward the catheter conduit distal end; wherein the distal end clip has a distal end clip axis which extends axially through the distal end clip from the distal end clip first end toward the distal end clip second end;

said distal end of said catheter being positioned proximate the opening of the patient's esophagus when the distal end of said endotracheal tube is inserted into the patient's trachea and the catheter is attached to the endotracheal tube;

(b) inserting into the oral cavity of the patient the intubation device oriented such that the distal end of the endotracheal tube enters first;

(c) orienting the distal end of the endotracheal tube with the patient's trachea;

(d) inserting the distal end of the endotracheal tube into the patient's trachea;

(e) inflating the inflatable cuff by administering a source of air into the inflation port; and (f) ventilating the patient through the endotracheal tube.

36. The method of claim 35 comprising the additional step of:

(g) directing a desired enteral tube into the proximal end of the catheter, through the catheter, out the distal end of the catheter and into the desired location of the patient.

37. A medical catheter device, attachable to an endotracheal tube having a proximal end and a distal end, for guiding the path of an enteral tube into the esophagus of a patient, comprising:

(a) a catheter conduit comprising a proximal end with a proximal end opening for receiving the enteral tube, and a distal end opposite the proximal end having a distal end opening opposite the proximal end opening, the distal end opening permitting the enteral tube to enter the esophagus of the patient; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit; and (b) a proximal end clip attached to the catheter conduit proximate the proximal end of the catheter conduit for receiving and removably attaching a portion of the endotracheal tube near the proximal end of the endotracheal tube; said distal end of said catheter being positioned proximate the opening of the patient's esophagus when the distal end of said endotracheal tube is inserted into the patient's trachea and the catheter is attached to the endotracheal tube.

38. The medical catheter device of claim 37 further comprising a distal end clip attached to the catheter conduit proximate the distal end of the catheter conduit for receiving and removably attaching another portion of the endotracheal tube located toward the distal end of the endotracheal tube.

39. A combination medical device comprising:

(a) an endotracheal tube for use in ventilating a patient's lungs, said endotracheal tube having an inside diameter defining an endotracheal ventilation lumen, a proximal end and a distal end, the endotracheal tube capable of defining an arcuate path in a first plane between its proximal end and its distal end to facilitate introduction of the endotracheal tube into the trachea of the patient, the endotracheal tube also having an inflatable cuff for achieving a seal, when inflated, with said endotracheal tube outside diameter and an inner wall of the trachea of the patient when the distal end of said endotracheal tube is inserted into the patient's trachea, said cuff being positioned generally toward the distal end of the endotracheal tube, the inflatable cuff being in fluid communication with an inflation port positioned generally toward the proximal end of the endotracheal tube, and (b) a catheter device, attachable to the endotracheal tube having a proximal end and a distal end, for guiding the path of an enteral tube into the esophagus of a patient, the catheter device comprising:

i. a catheter conduit comprising a proximal end with a proximal end opening for receiving the enteral tube, and a distal end opposite the proximal end having a distal end opening opposite the proximal end opening, the distal end opening permitting the enteral tube to enter the esophagus of the patient; a length defined as the distance between the proximal end and the distal end; an outer wall surface; an inner wall surface defining a catheter conduit interior space suitably sized to permit the passage of the enteral tube therethrough; a catheter conduit wall thickness defined as the space between the outer wall surface and the inner wall surface; the catheter conduit interior space further defined as the space between the proximal conduit opening, the distal conduit opening and the conduit inner wall surface; wherein the catheter conduit has a conduit proximal end axis which extends axially from and into the proximal end of the catheter conduit; wherein the catheter conduit has a conduit distal end axis which extends axially from and into the distal end of the catheter conduit; and ii. a proximal end clip attached to the catheter conduit proximate the proximal end of the catheter conduit for receiving and removably attaching a portion of the endotracheal tube near the proximal end of the endotracheal tube;

said distal end of said catheter being positioned proximate the opening of the patient's esophagus when the distal end of said endotracheal tube is inserted into the patient's trachea and the catheter is attached to the endotracheal tube.

40. The combination medical device of claim 39 further comprising a distal end clip attached to the catheter conduit proximate the distal end of the catheter conduit for receiving and removably attaching another portion of the endotracheal tube located toward the distal end of the endotracheal tube.

41. A combination intubation device comprising:
an endotracheal tube for ventilation of a patient's lungs, said endotracheal tube having an outside diameter, an inside diameter defining an endotracheal ventilation lumen, a proximal end and a distal end,
said endotracheal tube capable of defining an arcuate path in a first geometric plane between its proximal end and its distal end to facilitate introduction of said endotracheal tube into the trachea of the patient,
said endotracheal tube having a wall thickness defined as the space between said outside diameter and said inside diameter,
said arcuate path, when so defined, having a concave side and a convex side substantially opposite said concave side,
said endotracheal tube, when so defined in said arcuate path, having a concave side and a convex side substantially opposite said concave side,
said outside diameter of said endotracheal tube having a first edge along the concave side of said defined arcuate path and a second edge along the convex side of said defined arcuate path,
an inflatable cuff for achieving a seal, when inflated, with said endotracheal tube outside diameter and an inner wall of the trachea of the patient when the distal end of said endotracheal tube is inserted into the patient's trachea, said cuff being positioned generally toward the distal end of said endotracheal tube,
said inflatable cuff being in fluid communication with an inflation port positioned generally toward the proximal end of said endotracheal tube,
a catheter capable of receiving an enteral tube therethrough and guiding the path of the enteral tube, said catheter comprising:
a length defined by a proximal end and a distal end,
a catheter first side capable of being attached to said endotracheal tube along the length of said catheter, the length of said catheter extending along only a portion of the length of said endotracheal tube,
a catheter second side substantially opposite said catheter first side,
an outside diameter,
an inside diameter suitable to facilitate the movement of the enteral tube therethrough, said inside diameter defining an internal catheter conduit space between said catheter proximal and distal ends, the enteral tube having an outside diameter of sufficient size to permit movement of the enteral tube through said internal catheter conduit space,
a catheter proximal end opening at said catheter proximal end for receiving the enteral tube into said internal catheter conduit space,
a catheter distal end opening at said distal end to permit the enteral tube to enter the esophagus of the patient, and
a catheter wall thickness defined as the space between said outside diameter and said inside diameter,
said distal end of said catheter being positioned proximate the opening of the patient's esophagus when the distal end of said endotracheal tube is inserted into the patient's trachea, and
a proximal end clip attached to said catheter proximate said proximal end of the catheter conduit for receiving and removably attaching a portion of said endotracheal tube near said proximal end of said endotracheal tube.

42. The combination intubation device of claim 41 further comprising:
a distal end clip attached to said catheter conduit proximate said distal end of said catheter conduit for receiving and removably attaching another portion of said endotracheal tube located toward said distal end of said endotracheal tube.

* * * * *